(12) United States Patent
Li et al.

(10) Patent No.: US 10,137,118 B2
(45) Date of Patent: Nov. 27, 2018

(54) CRYSTALLINE POLYMORPHS OF THE FREE BASE OF 2-HYDROXY-6-((2-(1-ISOPROPYL-1H-PYRAZOL-5-YL)PYRIDIN-3-YL)METHOXY)BENZALDEHYDE

(71) Applicant: Global Blood Therapeutics, Inc., South San Francisco, CA (US)

(72) Inventors: Zhe Li, South San Francisco, CA (US); Stephan D. Parent, South San Francisco, CA (US); Travis Houston, South San Francisco, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 15/801,152

(22) Filed: Nov. 1, 2017

(65) Prior Publication Data

US 2018/0289686 A1    Oct. 11, 2018

Related U.S. Application Data

(63) Continuation of application No. 15/236,283, filed on Aug. 12, 2016, which is a continuation of application No. 14/616,548, filed on Feb. 6, 2015, now Pat. No. 9,447,071.

(60) Provisional application No. 61/937,404, filed on Feb. 7, 2014, provisional application No. 61/937,393, filed on Feb. 7, 2014.

(51) Int. Cl.
C07D 401/04    (2006.01)
A61K 31/4439   (2006.01)

(52) U.S. Cl.
CPC ........ A61K 31/4439 (2013.01); C07D 401/04 (2013.01)

(58) Field of Classification Search
CPC .................................................. C07D 401/04
USPC ...................................... 546/275.4; 514/341
See application file for complete search history.

(56) References Cited

U.S. PATENT DOCUMENTS

| | | |
|---|---|---|
| 3,236,893 A | 2/1966 | Blout et al. |
| 4,062,858 A | 12/1977 | Hoehn et al. |
| 4,410,537 A | 10/1983 | Kneen |
| 4,478,834 A | 10/1984 | Shroff et al. |
| 4,535,183 A | 8/1985 | Kneen |
| 5,185,251 A | 2/1993 | Chen et al. |
| 5,202,243 A | 4/1993 | Balani |
| 5,266,582 A | 11/1993 | De Nanteuil et al. |
| 5,290,941 A | 3/1994 | Volante et al. |
| 5,403,816 A | 4/1995 | Takabe et al. |
| 5,521,202 A | 5/1996 | Yano et al. |
| 5,679,678 A | 10/1997 | Binder et al. |
| 5,681,567 A | 10/1997 | Martinez et al. |
| 5,760,232 A | 6/1998 | Chen et al. |
| 5,840,900 A | 11/1998 | Greenwald et al. |
| 5,880,131 A | 3/1999 | Greenwald et al. |
| 5,965,566 A | 10/1999 | Greenwald et al. |
| 5,994,353 A | 11/1999 | Breault |
| 6,011,042 A | 1/2000 | Greenwald et al. |
| 6,111,107 A | 8/2000 | Greenwald et al. |
| 6,127,355 A | 10/2000 | Greenwald et al. |
| 6,153,655 A | 10/2000 | Martinez et al. |
| 6,194,580 B1 | 2/2001 | Greenwald et al. |
| 6,214,817 B1 | 4/2001 | Riley et al. |
| 6,232,320 B1 | 5/2001 | Stewart et al. |
| 6,239,176 B1 | 5/2001 | Nudelman et al. |
| 6,242,644 B1 | 6/2001 | Ackermann et al. |
| 6,355,661 B1 | 3/2002 | Lai et al. |
| 6,395,266 B1 | 5/2002 | Martinez et al. |
| 6,472,349 B1 | 10/2002 | Hamprecht et al. |
| 6,593,472 B2 | 7/2003 | Hoffman et al. |
| 6,608,076 B1 | 8/2003 | Greenwald et al. |
| 6,627,646 B2 | 9/2003 | Bakale |
| 6,630,496 B1 | 10/2003 | Seehra et al. |
| 7,160,910 B2 | 1/2007 | Safo et al. |
| 7,411,083 B2 | 8/2008 | Gopalsamy et al. |
| 8,846,694 B2 | 9/2014 | Heinrich et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,248,199 B2 | 2/2016 | Metcalf et al. |
| 9,422,279 B2 | 8/2016 | Metcalf et al. |
| 9,447,071 B2 | 9/2016 | Li et al. |
| 9,458,139 B2 | 10/2016 | Xu et al. |
| 9,604,999 B2 | 3/2017 | Harris et al. |
| 9,776,960 B2 | 10/2017 | Xu et al. |
| 9,802,900 B2 | 10/2017 | Li et al. |
| 2001/0046997 A1 | 11/2001 | Abraham et al. |
| 2002/0095035 A1 | 7/2002 | Warshawsky et al. |
| 2002/0142995 A1 | 10/2002 | Nicolau et al. |

(Continued)

FOREIGN PATENT DOCUMENTS

| CA | 2720096 | 10/2009 |
|---|---|---|
| CN | 101113148 | 1/2008 |

(Continued)

OTHER PUBLICATIONS

U.S. Appl. No. 61/581,053, filed Dec. 28, 2011, Metcalf et al.
U.S. Appl. No. 61/661,320, filed Jun. 18, 2012, Metcalf et al.
Abdulmalik et al., "Crystallographic analysis of human hemoglobin elucidates the structural basis of the potent and dual antisickling activity of pyridyl derivatives of vanillin", Acta Cryst. 2011, D67, 920-928.
Abdulmalik et al., Sickle cell disease: current therapeutic approaches, Expert Opinion Ther. Patents, 2005, vol. 15(11), pp. 1497-1506.

(Continued)

Primary Examiner — Patricia L Morris
(74) Attorney, Agent, or Firm — Sheppard Mullin Richter & Hampton LLP

(57) ABSTRACT

Disclosed are crystalline free base ansolvate forms of 2-hydroxy-6-((2-(1-isopropyl-1H-pyrazol-5-yl)pyridin-3-yl)methoxy)benzaldehyde (or Compound 1), such as the free base Form I, Form II and Material N. Also disclosed are crystalline free base solvates of 2-hydroxy-6-((2-(1-isopropyl-1H-pyrazol-5-yl)pyridin-3-yl)methoxy)benzaldehyde (or Compound 1).

6 Claims, 25 Drawing Sheets

(56) References Cited

U.S. PATENT DOCUMENTS

| | | | |
|---|---|---|---|
| 2002/0147138 A1 | 10/2002 | Firestone et al. |
| 2003/0022923 A1 | 1/2003 | Lai et al. |
| 2003/0060425 A1 | 3/2003 | Ahlem et al. |
| 2003/0073712 A1 | 4/2003 | Wang et al. |
| 2003/0165714 A1 | 9/2003 | Lee et al. |
| 2003/0187026 A1 | 10/2003 | Li et al. |
| 2003/0190333 A1 | 10/2003 | Mossman et al. |
| 2003/0199511 A1 | 10/2003 | Li et al. |
| 2004/0072796 A1 | 4/2004 | Embury et al. |
| 2004/0186077 A1 | 9/2004 | Diakur et al. |
| 2004/0209921 A1 | 10/2004 | Bridger et al. |
| 2005/0085484 A1 | 4/2005 | Mitchell et al. |
| 2005/0096337 A1 | 5/2005 | Ackermann et al. |
| 2005/0143420 A1 | 6/2005 | Moutouh-De Parseval et al. |
| 2005/0159605 A1 | 7/2005 | Tarur et al. |
| 2006/0094761 A1 | 5/2006 | Haque et al. |
| 2007/0213323 A1 | 9/2007 | Imogai et al. |
| 2007/0293698 A1 | 12/2007 | Quick et al. |
| 2008/0114167 A1 | 5/2008 | Castro et al. |
| 2009/0023709 A1 | 1/2009 | Gillespie et al. |
| 2009/0143371 A1 | 6/2009 | Buettelmann |
| 2009/0163512 A1 | 6/2009 | Chen et al. |
| 2009/0312315 A1 | 12/2009 | Yamaguchi et al. |
| 2010/0204235 A1 | 8/2010 | Lizos et al. |
| 2010/0210651 A1 | 8/2010 | Hernandez et al. |
| 2010/0311748 A1 | 12/2010 | Dakin et al. |
| 2012/0220569 A1 | 8/2012 | Ohashi et al. |
| 2012/0245344 A1 | 9/2012 | Endo et al. |
| 2013/0045251 A1 | 2/2013 | Cen et al. |
| 2013/0072472 A1 | 3/2013 | Gless et al. |
| 2013/0190315 A1 | 7/2013 | Metcalf et al. |
| 2013/0190316 A1 | 7/2013 | Metcalf et al. |
| 2013/0190375 A1 | 7/2013 | Dunkel et al. |
| 2014/0271591 A1 | 9/2014 | Sinha et al. |
| 2014/0274961 A1 | 9/2014 | Metcalf et al. |
| 2014/0275152 A1 | 9/2014 | Metcalf et al. |
| 2014/0275176 A1 | 9/2014 | Xu et al. |
| 2014/0275181 A1 | 9/2014 | Harris et al. |
| 2015/0057251 A1 | 2/2015 | Harris |
| 2015/0133430 A1 | 5/2015 | Xu et al. |
| 2015/0141465 A1 | 5/2015 | Yee et al. |
| 2015/0259296 A1 | 9/2015 | Li et al. |
| 2015/0336908 A1 | 11/2015 | Shioda et al. |
| 2015/0344472 A1 | 12/2015 | Metcalf et al. |
| 2015/0344483 A1 | 12/2015 | Metcalf et al. |
| 2016/0024127 A1 | 1/2016 | Harris et al. |
| 2016/0031865 A1 | 2/2016 | Li et al. |
| 2016/0031904 A1 | 2/2016 | Li et al. |
| 2016/0038474 A1 | 2/2016 | Sinha et al. |
| 2016/0039801 A1 | 2/2016 | Metcalf et al. |
| 2016/0046613 A1 | 2/2016 | Metcalf et al. |
| 2016/0083343 A1 | 3/2016 | Xu et al. |
| 2016/0303099 A1 | 3/2016 | Dufu et al. |
| 2016/0152602 A1 | 6/2016 | Xu et al. |
| 2016/0206604 A1 | 7/2016 | Metcalf et al. |
| 2016/0206614 A1 | 7/2016 | Metcalf et al. |
| 2016/0207904 A1 | 7/2016 | Li et al. |
| 2016/0332984 A1 | 11/2016 | Metcalf et al. |
| 2016/0346263 A1 | 12/2016 | Li et al. |
| 2017/0107199 A1 | 4/2017 | Metcalf et al. |
| 2017/0157101 A1 | 6/2017 | Ramos et al. |
| 2017/0174654 A1 | 6/2017 | Metcalf et al. |
| 2017/0327484 A1 | 11/2017 | Li et al. |

FOREIGN PATENT DOCUMENTS

| | | |
|---|---|---|
| CN | 102116772 | 7/2011 |
| DE | 2238734 | 2/1973 |
| DE | 2238628 | 3/1973 |
| DE | 2853765 | 6/1980 |
| DE | 2904829 | 8/1980 |
| DE | 226590 | 8/1985 |
| DE | 3503435 | 8/1985 |
| DE | 3431004 | 3/1986 |
| DE | 3704223 | 8/1987 |
| DE | 258226 | 7/1988 |
| DE | 276479 | 2/1990 |
| DE | 276480 | 2/1990 |
| DE | 3931954 | 3/1990 |
| DE | 4318550 | 12/1994 |
| DE | 4442050 | 5/1996 |
| EP | 010063 | 4/1980 |
| EP | 0054924 | 6/1982 |
| EP | 236140 | 9/1987 |
| EP | 0268989 | 6/1988 |
| EP | 0278686 | 8/1988 |
| EP | 0291916 | 11/1988 |
| EP | 0303465 | 2/1989 |
| EP | 0336369 | 10/1989 |
| EP | 0348155 | 12/1989 |
| EP | 0365328 | 4/1990 |
| EP | 0401517 | 12/1990 |
| EP | 0453210 | 10/1991 |
| EP | 0462800 | 12/1991 |
| EP | 0481802 | 4/1992 |
| EP | 0498380 | 8/1992 |
| EP | 0528337 | 2/1993 |
| EP | 0542372 | 5/1993 |
| EP | 0567133 | 10/1993 |
| EP | 0632036 | 1/1995 |
| EP | 0637586 | 2/1995 |
| EP | 0640609 | 3/1995 |
| EP | 0747393 | 12/1996 |
| EP | 2123637 | 11/2009 |
| EP | 2149545 | 3/2010 |
| EP | 2305625 | 6/2011 |
| FR | 2217016 | 1/1900 |
| FR | 2909379 | 6/2008 |
| GB | 1409865 | 10/1975 |
| GB | 1593417 | 7/1981 |
| IL | 64573 | 4/1985 |
| JP | 57-145844 | 6/1905 |
| JP | 59029667 | 2/1984 |
| JP | 61-040236 | 2/1986 |
| JP | 63230687 | 9/1988 |
| JP | S-63258463 | 10/1988 |
| JP | 01190688 | 7/1989 |
| JP | 06-041118 | 2/1994 |
| JP | 07-025882 | 1/1995 |
| JP | 2002-523469 | 7/2002 |
| JP | 2002-528537 | 9/2002 |
| JP | 2003-075970 | 3/2003 |
| JP | 2003-513060 | 4/2003 |
| JP | 2006-342115 | 12/2006 |
| JP | 2009-203230 | 9/2009 |
| WO | WO-91/19697 | 12/1991 |
| WO | WO-92/02503 | 2/1992 |
| WO | WO-93/17013 | 9/1993 |
| WO | WO-94/01406 | 1/1994 |
| WO | WO-95/14015 | 5/1995 |
| WO | WO-95/21854 | 8/1995 |
| WO | WO-96/11902 | 4/1996 |
| WO | WO-97/41120 | 11/1997 |
| WO | WO-97/44306 | 11/1997 |
| WO | WO-98/08818 | 3/1998 |
| WO | WO-98/21199 | 5/1998 |
| WO | WO-99/29694 | 6/1999 |
| WO | WO-99/43672 | 9/1999 |
| WO | WO-99/47529 | 9/1999 |
| WO | WO-99/48490 | 9/1999 |
| WO | WO-99/59978 | 11/1999 |
| WO | WO-99/62908 | 12/1999 |
| WO | WO-00/12121 | 3/2000 |
| WO | WO-00/26202 | 5/2000 |
| WO | WO-00/35858 | 6/2000 |
| WO | WO-00/40564 | 7/2000 |
| WO | WO-00/71123 A1 | 11/2000 |
| WO | WO-00/75145 | 12/2000 |
| WO | WO-00/78746 | 12/2000 |
| WO | WO-01/00612 | 1/2001 |
| WO | WO-01/19823 | 3/2001 |
| WO | WO-01/23383 | 4/2001 |
| WO | WO-01/32596 | 5/2001 |
| WO | WO-01/36375 | 5/2001 |

(56) References Cited

FOREIGN PATENT DOCUMENTS

| | | |
|---|---|---|
| WO | WO-01/57006 | 8/2001 |
| WO | WO-01/57044 | 8/2001 |
| WO | WO-01/62705 | 8/2001 |
| WO | WO-01/70663 | 9/2001 |
| WO | WO-02/00622 | 1/2002 |
| WO | WO-02/12235 | 2/2002 |
| WO | WO-02/24635 | 3/2002 |
| WO | WO-02/24679 | 3/2002 |
| WO | WO-02/051849 | 7/2002 |
| WO | WO-02/053547 | 7/2002 |
| WO | WO-03/051366 | 6/2003 |
| WO | WO-03/053368 | 7/2003 |
| WO | WO-03/101959 | 12/2003 |
| WO | WO-2004/014899 | 2/2004 |
| WO | WO-2004/018430 | 3/2004 |
| WO | WO-2004/024705 | 3/2004 |
| WO | WO-2004/050030 | 6/2004 |
| WO | WO-2004/056727 | 7/2004 |
| WO | WO-2004/058790 | 7/2004 |
| WO | WO-2004/087075 | 10/2004 |
| WO | WO-2004/111031 | 12/2004 |
| WO | WO-2005/047249 | 5/2005 |
| WO | WO-2005/074513 | 8/2005 |
| WO | WO-2005/077932 | 8/2005 |
| WO | WO-2005/086951 | 9/2005 |
| WO | WO-2005/087766 | 9/2005 |
| WO | WO-2005/096337 | 10/2005 |
| WO | WO-2006/011469 | 2/2006 |
| WO | WO-2006/065204 | 6/2006 |
| WO | WO-2006/088173 | 8/2006 |
| WO | WO-2006/103463 | 10/2006 |
| WO | WO-2006/106711 | 10/2006 |
| WO | WO-2006/116764 | 11/2006 |
| WO | WO-2006/003923 | 12/2006 |
| WO | WO-2007/003962 | 1/2007 |
| WO | WO-2007/009389 | 1/2007 |
| WO | WO-2007/017267 | 2/2007 |
| WO | WO-2007/047204 | 4/2007 |
| WO | WO-2007/049675 | 5/2007 |
| WO | WO-2007/061923 | 5/2007 |
| WO | WO-2007/084914 | 7/2007 |
| WO | WO-2007/117180 | 10/2007 |
| WO | WO-2008/013414 | 1/2008 |
| WO | WO-2008/016132 | 2/2008 |
| WO | WO-2008/029200 | 3/2008 |
| WO | WO-2008/041118 | 4/2008 |
| WO | WO-2008/051532 | 5/2008 |
| WO | WO-2008/060391 | 5/2008 |
| WO | WO-2008/066145 | 6/2008 |
| WO | WO-2008/081096 | 7/2008 |
| WO | WO-2008/101682 | 8/2008 |
| WO | WO-2008/116620 | 10/2008 |
| WO | WO-2009/001214 | 12/2008 |
| WO | WO-2009/011850 | 1/2009 |
| WO | WO-2009/050183 | 4/2009 |
| WO | WO-2009/125606 | 10/2009 |
| WO | WO-2009/128537 | 10/2009 |
| WO | WO-2009/130560 | 10/2009 |
| WO | WO-2009/136889 | 11/2009 |
| WO | WO-2009/146555 | 12/2009 |
| WO | WO-2010/031589 | 3/2010 |
| WO | WO-2010/056631 | 5/2010 |
| WO | WO-2010/129055 | 11/2010 |
| WO | WO-2011/033045 | 3/2011 |
| WO | WO-2011/088201 | 7/2011 |
| WO | WO-2011/136459 | 11/2011 |
| WO | WO-2012/020060 | 2/2012 |
| WO | WO-2012/138981 | 10/2012 |
| WO | WO-2012/141228 | 10/2012 |
| WO | WO-2013/052803 | 4/2013 |
| WO | WO-2013/102142 | 7/2013 |
| WO | WO-2013/102145 | 7/2013 |
| WO | WO-2014/104384 | 7/2014 |
| WO | WO-2014/150256 | 9/2014 |
| WO | WO-2014/150258 | 9/2014 |
| WO | WO-2014/150261 | 9/2014 |
| WO | WO-2014/150268 | 9/2014 |
| WO | WO-2014/150276 | 9/2014 |
| WO | WO-2014/150289 | 9/2014 |
| WO | WO-2015/031284 | 3/2015 |
| WO | WO-2015/031285 | 3/2015 |

OTHER PUBLICATIONS

Abraham et al., Vanillin, a Potential Agent for the Treatment of Sickle Cell Anemia, Blood, Mar. 1991, vol. 77 (6), pp. 1334-1341.
Adhikary, P.K., et al., "A new antisickling agent: in vitro studies of its effect on S/S erythrocytes and on hemoglobin S", Experientia. 1978, vol. 34, No. 6, pp. 804-806.
Appendix A provided with Israel office action dated Aug. 11, 2016 for IL 233329.
Arya R, et al. "Tucaresol increases oxygen affinity and reduces haemolysis in subjects with sickle cell anaemia," Br. J. Haematol., 93(4):817-21 (1996).
Australian Examination Report dated Nov. 7, 2016 for AU 2016203755.
Babu, et al. Regioselective synthesis and structural elucidation of 1,4-disubstituted 1,2,3-triazole derivatives using 1D and 2D NMR spectral techniques. Magn. Reson. Chem., 2011; 49: 824-829. doi:10.1002/mrc.2820.
Bacsa et al., "Novel products from Baylis-Hillman reactions of salicylaldehydes", South African Journal of Chemistry (1998), 51(1), 47-54 CODEN: SAJCDG; ISSN: 0379-4350.
Ballerini et al., High pressure Diels-Alder approach to hydroxy-substituted 6a-cyano-tetrahydro-6H-benzo[c]chromen-6-ones: A route to Δ6-Cis-Cannabidiol. J.Org.Chem., 74(11):4311-4317, 2009.
Ballet et al., Novel selective human melanocortin-3 receptor ligands: Use of the 4-amino-1,2,4,5-tetrahydro-2-benzazepin-3-one (Aba) scaffold, Bioorganic & Medicinal Chemistry Letters (2007), 17(9), 2492-2498 CODEN: BMCLES; ISSN: 0960-894X.
Barnes, et al., "Prospects for new drugs for chronic obstructive pulmonary disease." The Lancet, 2004, 364, 985-996.
Barnes. "COPD: is there light at the end of the tunnel?" Current Opinion in Pharmacology, 2004, 4:263-272.
Baxter et al., "Reductive aminations of carbonyl compounds with borohydride and borane reducing agents", Organic Reactions (Hoboken, NJ, United States) (2002), 59, No pp. given bin/mrwhome/107610747/HOME.
Beaumont et al., Design of ester prodrugs to enhance oral absorption of poorly permeable compounds: challenges to the discovery scientist. Curr. Drug Metab. 2003, 4:461-85.
Beddell, Substituted benzaldehydes designed to increase the oxygen affinity of human haemoglobin and inhibit the sickling of sickle erythrocycles, Br. J. Pharmac., 82:397-407, 1984.
Beena et al., "Synthesis and antibacterial activity evaluation of metronidazole-triazole conjugates", Bioorganic & Medicinal Chemistry Letters, 2009, 19(5):1396-1398.
Berge et al., "Pharmaceutical Salts", Journal of Pharmaceutical Science, 1977, 66:1-19.
Bernstein. Crystals in Supramolecular Chemistry. ACA Transactions. 2004; 39:1-14.
Bernstein. Polymorphism in Molecular Crystals. Clarendon Press, Oxford. 2002. 115-118, 272.
Bode et al.,"Novel synthesis and x-ray crystal structure of a coumarin derivative", South African Journal of Chemistry (1992), 45(1), 25-7 CODEN: SAJCDG; ISSN:0379-4350.
Bonaventura, et al., "Molecular Controls of the Oxygenation and Redox Reactions of Hemoglobin." Antioxidants & Redox Signaling, 18(17), 2013, 2298-2313.
Bottino, et al. Study on the scope of tert-amino effect: new extensions of type 2 reactions to bridged biaryls. J. Phys. Org. Chem. 2012; 25(11):1033-1041.
Bradbury et al., "New nonpeptide angiotensin II receptor antagonists", Journal of Medicinal Chemistry, 1993, vol. 36, pp. 1245-1254.
Braga, et al. Making crystals from crystals: a green route to crystal engineering and polymorphism. Chem Commun (Camb). Aug. 7, 2005;(29):3635-45. Epub Jun. 15, 2005.

(56) References Cited

OTHER PUBLICATIONS

Britton et al., "Structure-activity relationships of a series of benzothlophens-derived NPY Y1 antagonists: optimization of the C-2 side chain". Bioorganic & Medicinal Chemistry Letters (1999), 9(3), 475-480 CODEN:BMCLE8;ISSN: 0960-894X.
Brown et al., "1,2-Dihydroisoquinollnes. III, Dimerization", Tetrahedron (1966), 22(8), 2437-43 CODEN: TETRAB; ISSN;0040-4020.
Caira. Crystalline Polymorphism of Organic Compounds. Topics in Current Chemistry, Springer, Berlin, DE. 1998; 198:163-208.
CAS Registry No. 1039841-20-7; entry dated Aug. 10, 2008.
CAS Registry No. 1096911-11-3; entry dated Jan. 28, 2009.
CAS Registry No. 1153166-41-6; entry dated Jun. 7, 2009.
CAS Registry No. 1153961-01-3; entry dated Jun. 8, 2009.
CAS Registry No. 1184809-65-1; entry dated Sep. 15, 2009.
CAS Registry No. 1303782-57-1; entry dated Jun. 1, 2011.
CAS Registry No. 1306264-96-9; entry dated Jun. 5, 2011.
CAS Registry No. 631858-40-7; entry dated Dec. 29, 2003.
Chemical Abstract Registry No. 1142191-55-6, indexed in the Registry File on STN CA Online May 4, 2009.
Cheng, et al. Vilsmeier formylation of tert-anilines: dibenzo[b,f][1,5]diazocines and quinazolinium salts via the 't-amino effect'. J. Chem. Soc., Perkin Trans 1. 1998; 1257-1262.
Cherian et al., "Structure-Activity Relationships of Antitubercular Nitroimidazoles 3. Exploration of the Linker and Lipophilic Tail of ((S)-2-Nitro-6,7-dihydro-5H-imidazo[2,1-b][1,3]oxazin-6-yl)-(4-trifluoromethoxybenzyl)amine (6-Amino PA-824).," J. Med. Chem., Aug. 2011, vol. 54(16), pp. 5639-5659.
Ciganek, "The catalyzed a-hydroxyalkylation and a-aminoalkylation of activated olefins (the Morita-Baylis-Hillman reaction", Organic Reactions (Hoboken, NJ, United States) (1997), 51, No pp given CODEN:ORHNBA URL:http://www3.Interscience.wiley.com/cgi-bin/mnwhome/107610747/HOME.
CMU Pharmaceutical polymorphism, internet p. 1-3 (2002) printout Apr. 3, 2008.
Concise Encyclopedia Chemistry, NY: Walter de Gruyter, 1993, 872-873.
Congreve et al. Application of Fragment Screening by X-ray Crystallography to the Discovery of Aminopyridines as Inhibitors of Beta-Secretase. J. Med. Chem. 50:1124-1132 (2007).
Cos et al., "Structure-Activity Relationship and Classification of Flavonoids as Inhibitors of Xanthine Oxidase and Superoxide Scavengers," J. Nat. Prod., (1998), 61:71-76.
Database CA Chemical Abstract Service, Li et al., "Substituted-benzoheterocycle derivatives, preparation, and application for preparation of antiviral or antineoplastic drugs," XP002726578 retrieved from STN Database accession No. 2013:366779 (abstract); RN:1427163-92-5 & CN 102 952 062 A, Mar. 6, 2013, 2 pages.
Database Pubchem Compound Dec. 4, 2011 XP 003033770 (11 pages).
Database Registry, 2011, RN 1289869-72-2, 1027970-95-1, 959671-57-9.
Database Registry, 2012, RN 1390863-18-9, 1390573-58-6, 1389652-57-6, 1387166-17-7, 1318517-26-8, 1318395-05-9, 933829-46-0, 879919-21-8.
Davidovich, et al. Detection of polymorphism by powder x-ray diffraction: interference by preferred orientation. Am. Pharm. Rev. 2004; 10, 12, 14, 16, 100.
Dean. Analytical Chemistry Handbook. University of Tennese, Knoxville. McGraw-Hill, Inc. 1995; 10.24-10.26.
Deem. "Red Blood Cells and Hemoglobin in Hypoxic Pulmonary Vasoconstriction" Advances in experimental medicine and biology, (2006) 588, 217-231.
Desai et al. Preparation of N-[ro-(4-aryl-1-piperazinyl)ethyl/propyl]-3-hydroxyphthalimidines. Indian Journal of Chemistry. 39:455-457 (2000).
Desideri et al., "Guanylhydrazones of 3-substituted 2-pyridinecarboxaldehyde and of (2-substituted 3-pyridinyloxy) acetaldehyde as prostanoid biosynthesis and platelet aggregation inhibitors", European Journal of Medicinal Chemistry, Editions Scientifique Elsevier, Paris, FR, 1991, vol. 26, No. 4, pp. 455-460.
Di Stilo, et al. New 1,4-dihydropyridines conjugated to furoxanyl moieties, endowed with both nitric oxide-like and calcium channel antagonist vasodilator activities. J. Med. Chem. 41:5393-5401 (1998).
Ding et al., "Crystal structure of bis[μ2-2-(2-formylphenoxy)acetato-O,O]-bis[μ2-2-2-formylphynoxy)acetato-O,O]-octakis(n-butyl)tetratin(IV), Sn4O2(C9H7O4)4(C4H9)8", Zeitschrift fuer Kristallographie—New Crystal Structures (2011), 226(1), 31-32 CODEN:ZKNSFT; ISSN: 1433-7266.
Doelker, English translation of S.T.P, Pratiques (1999), 9(5), 399-409.
Doelker. English translation of Ann. Pharm. Fr., 2002, 60: 161-176.
Einfalt, et al. Methods of amorphization and investigation of the amorphous state. Acta Pharm. 2013; 63:305-334.
Elwahy, "Synthesis of new benzo-substituted macrocyclic containing quinoxaline subunits" Tetrahedron (2000), 56(6), 897-907 CODEN:TETRAB; ISSN:0040-4020.
Epsztajn et al., "Application of organolithium", Tetrahedron, Elsevier Science Publishers, Amsterdam, NL, 1991, vol. 47, No. 9, pp. 1697-1706.
European Search Report and Search Opinion dated Aug. 4, 2015 for EP Application No. 12862525.8. 9 pages.
European Search Report and Search Opinion dated Jul. 21, 2016 for EP Application No. 14769616.5. 8 pages.
European Search Report and Search Opinion dated May 28, 2015 for EP Application No. 12862096.0. 13 pages.
European Search Report and Search Opinion dated Nov. 16, 2016 for EP Application No. 16194019.2. 13 pages.
European Search Report and Search Opinion dated Sep. 26, 2016 for EP Application No. 14768759.4. 6 pages.
Extended European Search Report and opinion dated Jul. 20, 2016 for EP Application No. 14768414.6. 10 pages.
Extended European Search Report and Search Opinion dated Jul. 18, 2016 for EP Application No. 14770695.6. 13 pages.
Extended European Search Report and Search Opinion dated Jul. 7, 2016 for EP Application No. 14768317.1.7 pages.
Extended European Search Report and Search Opinion dated May 17, 2017 for EP Application No. 15746995.8. 8 pages.
Extended European Search Report and Search Opinion dated Nov. 23, 2015 for EP Application No. 12862525.8. 16 pages.
Gadaginamath, et al., "Synthesis and antibacterial activity of novel 1-butyl-2-phenoxyl2-phenylthlol2-aminomethyl-5-methoxyindole derivatives", Polish Journal of Chemistry (1997), 71(7), 923-928 CODEN: PJCHDQ; ISSN:0137-5083.
Gao et al, "A novel one-pot three-step synthesis of 2-(1-benzofuran-2-yl)quinoline-3-carboxylic acid derivatives", Journal of the Brazilian Chemical Society (2010), 21(5). 806-812 CODEN:JOCSET; ISSN: 0103-5053.
Ghate et al., "Synthesis of vanillin ethers from 4-(bromomethyl) coumarins as anti-inflammatory agents,"European Journal of Medicinal Chemistry (2003), 38(3), 297-302 CODEN: EJMCAS; ISSN: 0223-5234.
Gibson et al., "Novel small molecule bradykinin B2 receptor antagonists", Journal of Medicinal Chemistry, 2009, vol. 52, pp. 4370-4379.
Glasson et al. Metal Template Synthesis of a Tripodal Tris(bipyridyl) Receptor that Encapsulates a Proton and an Iron (ii) Centre in a Pseudo Cage. Aust. J. Chem. 65:1371-1376 (2012).
Grashey, "The nitro group as a 1,3-dipole in cycloadditions" Angewandte Chemie (1962), 74, 155 CODEN: ANCEAD; ISSN: 0044-8249.
Guillaumel, et al. Synthetic routes to 2-(2-benzofuranyl)benzoic acids and their cyclization into benz[6]indeno[2,1-d]furan-10-ones. Journal of Heterocyclic Chemistry, 1990; 27: 1047-1051. doi:10.1002/jhet.5570270444.
Guillory (in Brittain ed.) Polymorphism in Pharmaceutical Solids. NY, Marcel Dekker, Inc. 1999; 1-2:183-226.
Gunter et al., "Structural control of co-receptor binding in porphyrin-bipyridinium supramolecular assemblies", Journal of the Chemical Society, Perkin Transactions 1: Organic and Bio-Organic Chemistry (1998), (12), 1945-1958 CODEN: JCPRB4; ISSN: 0300-922X.

(56) References Cited

OTHER PUBLICATIONS

Hang, Song. "Pharmaceutical Separation Engineering" East China University of Technology Press. Aug. 31, 2011; 270-272. (in Chinese with English abstract).
Hanmantgad et al., "Synthesis and pharmacological properties of some r-(2benzo[b]furanyl)coumarins" Indian Journal of Chemistry, Section B: Organic Chemistry Including Medicinal Chemistry (1986), 25B(7), 779-81 CODEN: IJSBDB; ISSN: 0376-4699.
He et al., "Prodrugs of Phosphonates, Phosphinates, and Phosphates", Prodrugs: Challenges and rewards Part 2, edited by Stella et al., 2007, pp. 223-264.
Heimbach et al., "Enzyme-mediated precipitation of patent drugs from their phosphate prodrugs", International Journal of Pharmaceutics, 261, p. 81-92, 2003.
Heimbach et al., "Prodrugs: Challenges and Rewards Part I," New York, NY, Singer:AAPS Press, (2007), 5(Chapter 2.2.1):157-215 Overcoming Poor Aqueous Solubility of Drugs for Oral Delivery.
Heimgartner et al., "Stereoselective synthesis of swainsonines from pyridines", Tetrahedron, Elsevier Science Publishers, Amsterdam, NL, 2005, vol. 61, No. 3, pp. 643-655.
Hoffman, et al. 3-Hydroxy-3-methyglutaryl-coenzyme A Reductase Inhibitors, 2. Structural Modification of 7-(Substituted aryl)-3,5-dihydroxy-6-heptenoic Acids and Their Lactone Derivatives. Journal of Medical Chemistry. 29(2):159-169 (1986).
Hong et al., "Potential Anticancer Agents VI: 5-Substituted Pyrimidine-6carboxaldehydes", Journal of Pharmaceutical Sciences, American Pharmaceutical Association, Washington, US, 1970, vol. 59, No. 11, pp. 1637-1645.
Huckauf, et al. "Oxygen Affinity of Haemoglobin and Red Cell Acid-Base Status in Patients with Severe Chronic Obstructive Lung Disease" Bull. Europe Physiopath. Resp., 1976, 12, 129-142.
International Preliminary Report on Patentability for PCT/US2014/022846 dated Sep. 15, 2015. 7 pages.
International Preliminary Report on Patentability for PCT/US2014/022742 dated Sep. 15, 2015. 7 pages.
International Preliminary Report on Patentability for PCT/US2014/022733 dated Sep. 15, 2015. 11 pages.
International Preliminary Report on Patentability for PCT/US2014/022769 dated Sep. 15, 2015. 8 pages.
International Search Report and Written Opinion dated Aug. 19, 2014 for PCT Application No. PCT/US2014/022736. 14 pages.
International Search Report and Written Opinion dated Aug. 27, 2014 for PCT Application No. PCT/US2014/022742. 11 pages.
International Search Report and Written Opinion dated Aug. 4, 2017 for PCT Application No. PCT/US2017/032104. 10 pages.
International Search Report and Written Opinion dated Dec. 8, 2014 for PCT Application No. PCT/US2014/052575. 10 pages.
International Search Report and Written Opinion dated Jul. 22, 2014 for PCT Application No. PCT/US2014/022846. 11 pages.
International Search Report and Written Opinion dated Jul. 30, 2014 for PCT Application No. PCT/US2014/029682. 16 pages.
International Search Report and Written Opinion dated Jul. 31, 2014 for PCT Application No. PCT/US2014/022789. 13 pages.
International Search Report and Written Opinion dated Jul. 4, 2014 for PCT Application No. PCT/US2014/022769. 11 pages.
International Search Report and Written Opinion dated Mar. 5, 2013 for PCT Application No. PCT/US2012/072177. 7 pages.
International Search Report and Written Opinion dated May 11, 2015 for PCT Application No. PCT/US2015/014589. 5 pages.
International Search Report and Written Opinion dated May 20, 2013 for PCT Application No. PCT/US2012/072183. 11 pages.
International Search Report and Written Opinion dated Nov. 28, 2014 for PCT Application No. PCT/US2014/052576. 10 pages.
International Search Report and Written Opinion dated Oct. 31, 2014 for PCT Application No. PCT/US2014/013575. 10 pages.
Israel office action dated Aug. 11, 2016 for Israeli Patent Application No. 233329.
Ito et al., A medium-term rat liver bioassay for rapid in vivo detection of carcinogenic potential of chemicals,01D Cancer Science, Jan. 2003, 94, pp. 3-8.
Ivanisevic, et al. Uses of x-ray powder diffraction in the pharmaceutical industry. Pharm. Sci. Encycl. 2010; 1-42.
Jain, et al., "Polymorphism in Pharmacy", Indian Drugs, 1986, 23(6) 315-329.
Jarvest et al., "Discovery and optimisation of potent, selective, ethanolamine Inhibitors of bacterial phenylalanyl tRNA synthetase", Bioorganic & Medicinal Chemistry Letter (2005), 15(9), 2305-2309 CODEN: BMCLES; ISSN: 0960-894X.
Karche et al., "Electronic Effects in Migratory Groups [1,4]- versus [1,2]-Rearrangement in Rhodium Carbenoid Generated Bicyclic Oxonium Ylides", Journal of Organic Chemistry (2001), 66(19), 6323-6332 CODEN: JOCEAH; ISSN: 0022-3263.
Katritzky et al., "Syntheses of 3-hydroxymethyl-2-3-dihydrobenzofurans and 3-hydroxymethylbenzofurans", ARKIVOC (Gainesville, FL, United States) (2003), (6), 49-61 CODEN: AGFUAR URL: http://www.arkat-usa.org/ark/journa1/2003/Vargoglis/AV-622A/6ss.pdf.
Kaye et al., "DABCO-catalyzed reactions of salicylaldehydes with acrylate derivatives", Synthetic Communications (1996), 26(11), 2085-97 CODEN: SYNCAV; ISSN: 0039-7911.
Kaye et al., "Does the DABCO-catalyzed reaction of 2-hydroxybenzaldehydes with methyl acrylate follow a Baylis-Hillman pathway?", Organic & Biomolecular Chemistry (2003), 1(7), 1133-1138 CODEN: OBCRAK; ISSN: 1477-0520.
Keidan, et al. Effect of BW12C on oxygen affinity of hemoglobin in sickle-cell disease. The Lancet. 1986; 327(8485):831-834.
Kessar et al., "Synthesis of Isoindolobenzazepines via photocyclisation of N-(2-formylphenethyl)phthalimide derivatives", Indian Journal of Chemistry, Section B: Organic Chemistry Including Medicinal Chemistry (1991), 30B(11), 999-1005 CODEN: JSBDB; ISSN:3076-4699.
Kessar et al., An Interesting Application of Photocyclisation in Apophdeadane Alkaloid Synthesis. Tetrahedron Letters (1987), 28(44), 5323-5326. CODEN: TELEAY; ISSN: 0040-4039.
Kirk-Othmer Encyclopedia of Chemical Technology. 2002; 8:95-147.
Kise et al., "Electroreductive Intramolecular Coupling of Phthalimides with Aromatic Aldehydes: Application to the Synthesis of Lennoxamine". Journal of Organic Chemistry (2011), 76(23), 9856-9880 CODEN:JOCEAH; ISSN: 0022-3263.
Klis, et al. Halogen-lithium exchange versus deprotonation: synthesis of diboronic acids derived from aryl-benzyl ethers. Tetrahedron Letters, 48(7):1169-1173 (2007).
Kratochvil. Chapter 8 Solid Forms of Pharmaceutical Molecules. J. Sestak et al. (eds.), Glassy, Amorphous and Nano-Crystalline Materials. Hot Topics in Thermal Analysis and Calorimetry 8, 2011, pp. 129-140.
Krow,"The Baeyer-Villiger oxidation of ketones and aldehydes", Organic Reactions (Hoboken, NJ, United States) (1993), 43, No pp. given CODEN: ORHNBA URL: http://www3.interscience.wiley.com/cgi-bin/mrwhome/107610747/HOME.
Lakkannavar et al., "4-[2'-benzylideneanlino arylownethyl] coumarins E and Z isomers". Indian Journal of Heterocyclic Chemistry (1995), 4(4), 303-4 CODEN: IJCHEI; ISSN: 0971-1627.
Lin et al. Synthesis and anticancer activity of benzyloxybenzaldehyde derivatives against HL-60 cells. Bioorganic & Medicinal Chemistry. 13(5), 1537-1544 (2005).
Lin et al., "Potential Antitumor Agents.8. Derivatives of 3- and 5-Benzyloxy-2-formylpyridine Thiosemicarbazone", Journal of Medicinal Chemistry, American Chemical Society, US, 1972, vol. 15, No. 6, pp. 615-618.
Liu et al., "Synthesis of Double-Armed Benzo-15-crown-5 and Their Complexation Thermodynamics with Alkali Cations", Journal of Inclusion Phenomena and Macrocyclic Chemistry (2005), 52(3-4), 229-235 CODEN: JIPCF5; ISSN: 1388-3127.
Luan, et al. TOPS-MODE model of multiplexing neuroprotective effects of drugs and experimental-theoretic study of new 1,3-rasagiline derivatives potentially useful in neurodegenerative diseases. Bioorganic & Medicinal Chemistry. 2013; 21:1870-1879.
Mahoney et al., "Functionalization of Csp3-H bond-Sc(OTf)3-catalyzed domino 1,5-hydride shift/cyclization/Friedel-Crafts acylation reaction of benzylidene Meldrum's acids", Tetrahedron Letters (2009), 50(33), 4706-4709 CODEN: TELEAY; ISSN: 0040-4039.

(56) References Cited

OTHER PUBLICATIONS

Majhi et al., "An efficient synthesis of novel dibenzo-fused nine-membered oxacycles using a sequential Baylis-Hillman reaction and radical cyclization", Synthesis (2008), (1), 94-100 CODEN: SYNTBF; ISSN: 0039-7881.

Manna et al., Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, IL FARMACO, 1996, vol . 51, No. 8, 9, pp. 579-587.

Mantyla et al., Synthesis, in vitro evaluation, and antileishmanial activity of water-soluble prodrugs of buparvaquone. J. Med. Chem. 2004, 47:188-195.

Marchetti et al., "Synthesis and biological evaluation of 5-substituted O4-alkylpyrimidines as CDK2 inhibitors," Org. Biomol. Chem, 2010, vol. 8, pp. 2397-2407.

"Master of Engineering Education Chemical Engineering Development Report" National Engineering Education Master in Chemical Engineering Cooperation Group, Zhejiang University Press. Mar. 31, 2011; 241-245. (in Chinese with English abstract).

McKay et al., 7,11,15,28-Tetrakis[(2-formylphenoxy)methyl]-1,21,23,25-tetramethylresorcin[4]arene cavitand ethyl acetate clathrate at 173 K, Acta Crystallographica, Section E: Structure Reports Online (2009), E65(4), 692-693 CODEN: ACSEBH; ISSN: 1600-5368 URL: http://journals.lucrorg/e/issues/2009/04/00f122 33/fl2233. pdf.

McKay et al., "Microwave-assisted synthesis of a new series of resorcin[4]arene cavitand-capped porphyrin capsules", Organic & Biomolecular Chemistry (2009), 7(19), 3958-3968 CODEN: OBCRAK; ISSN: 1477-0520.

Merlino et al., "Development of second generation amidinohydrazones, thio- and semicarbazones as Trypanosoma cruzi-inhibitors bearing benzofuroxan and benzimidazole 1,3-dioxide core scaffolds" , MedChemComm (2010), 1(3), 216-228 CODEN: MCCEAY; ISSN: 2040-2503.

Mesguiche et al.,"4-Alkoxy-2,6-diaminopyrimidine Derivatives: Inhibitors of Cyclin Dependent Kinases 1 and 2," Bioorganic & Medicinal Chemistry Letters, Jan. 2003, vol. 13, pp. 217-222.

Metcalf, et al., "Discovery of GBT440, an Orally Bioavailable R-State Stabilizer of Sickle Cell Hemoglobin," ACS Med. Chem. Lett., 2017, 8, 321-326.

Mitra et al., Synthesis and biological evaluation of dibenz[b,f][1,5]oxazocine derivatives for agonist activity at x-opioid receptor, European Journal of Medicinal Chemistry (2011), 46(5), 1713-1720 CODEN: EJMCAS; ISSN: 0223-5234.

Mulwad et al., "Synthesis and antimicrobial activity of [6'-methyl-4'-methoxy-2-oxo-2H-[1]-benzopyran)-2",4" dihydro-[1",2",4"}-triazol-3'-one and 3'phenylthiazolidin-4'-one-phenoxymethyl derivatives of dipyranoquinoline", Pharmaceutical Chemistry Journal Ahead of Print CODEN: PCJOAU; ISSN: 0091-150, 2011; pp. 427-432.

Muzaffar, et al., "Polymorphism and Drug Availability: a Review" J of Pharm. (Lahore), 1979, 1(1), 59-66.

Nagy et al., Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling. Proc. Natl. Acad. Sci. USA 1993, 90:6373-6376.

Neelima et al., "A novel annelation reaction: synthesis of 6H-[1]benzopyrano[4,3-b]quinolines"Chemistry & Industry (London, United Kingdom) (1986), (4), 141-2 CODEN: CHINAG; ISSN: 00093068.

Nnamani, et al., "Pyridyl derivatives of benzaldehyde as potential antisickling agents," Chem. Biodivers., (2008), 5(9):1762-1769.

Nogrady, Medicinal Chemistry A Biochemical Approach, Oxford University Press, New York, pp. 388-393 (1985).

Nonoyama et al.,"Cyclometallation of 2-(2-pyridyl)benzo[b]furen and 1-(2-pyridyl and 2-pyrimidyl)indole with palladium(II) and rhodium(III). Structures of unexpectedly formed nitro palladium(II) complexes", Polyhedron 1999, 533-543 CODEN: PLYHDE; ISSN: 0277-5387.

Notice of Allowance dated Dec. 19, 2014 for U.S. Appl. No. 13/730,730. 11 pages.

Nyerges et al, "Synthesis of Indazole N-oxides via the 1,7-electrocyclization of azomethine ylides", Tetrahedron Letters (2001), 42(30), 5081-5083 CODEN: TELEAY; ISSN:0040-4039.

Nyerges et al, "Synthesis of Indazole N-oxides via the 1,7-electrocyclization of azomethine ylides", Tetrahedron Letters (2004), 60(44), 9937-9944 CODEN: TETRAB; ISSN:0040-4020.

OECD SIDS "SIDS Initial Assessment Report for 13th SIAM," Nov. 2001, pp. 1-95.

Office Action dated Aug. 29, 2014 for U.S. Appl. No. 13/730,730. 17 pages.

Office Action dated Dec. 3, 2013 for U.S. Appl. No. 13/730,674. 8 pages.

Office Action dated Jul. 6, 2015 for U.S. Appl. No. 13/815,874. 14 pages.

Office Action dated Jun. 12, 2015 for CN Application No. 201280070743.5. 13 pages.

Office Action dated Jun. 29, 2015 for U.S. Appl. No. 13/815,810. 19 pages.

Office Action dated Jun. 30, 2014 for U.S. Appl. No. 13/730,674. 9 pages.

Office Action dated Sep. 18, 2013 for U.S. Appl. No. 13/730,674. 10 pages.

Oh, et al. Solid-phase synthesis of 1,3-oxazolidine derivatives. Tetrahedron Letters. 2000; 41:5069-5072.

O'Reilly, "Metal-phenoxyalkanoic acid interactions, XXV. The crystal structures of (2-formyl-6-methoxyphenoxy)acetic acid and its zinc(II)complex and the lithium, zinc(II) and cadmium(II) complexes of (2-chlorophenoxy)acetic acid", Australian Journal of Chemistry (1987), 40(7)m 1146-59 CODEN; AJCHAS; ISSN:0004-9425.

Otsuka, et al., "Effect of Polymorphic Forms of Bulk Powders on Pharmaceutical Properties of Carbamazepine Granules." Chem. Pharm. Bull., 47(6) 852-856 (1999).

Patani, et al. Bioisosterism: A Rational Approach in Drug Design. J. Chem Rev. 1996, 96(8), pp. 3147-3176.

Perez et al., "Preparation of new 1,2-disubstituted ferrocenyl ammonium salt", Polyhedron (2009), 28(14), 3115-3119 CODEN: PLYHE; ISSN:0277-5387.

Perkins et al., "Manganese(II), Iron(II), cobalt(II), and cooper(II)complexes of an extended inherently chiral tris-bipyridyl cage", Proceedings of the National Academy of Sciences of the United States of America (2006), 103(3), 532-537 CODEN: PNASA6; ISSN: 0027-8424.

Potapov, et al. A convenient synthesis of heterocyclic compounds containing 11-oxo-6,11,12,13-tetrahydrodibenzo[b,g][1,5]oxazonine fragment. Mendeleev Communications. 2009; 19:287-289.

Prohens, et al. Polymorphism in pharmaceutical industry. The Pharmacist. Apr. 1, 2007; 373:58-68. (in Spanish with English abstract).

PUBCHEM CID 54009805 Create Date: Dec. 4, 2011 p. 1.

PUBCHEM CID 54883281 Create Date: Aug. 19, 2012 p. 1.

Remington's Pharmaceutical Sciences, 17th Edition, A. Gennaro editor, Easton Pennsylvania. Table of Contents. (1985).

Rodriguez-Spong, et al. General principles of pharmaceutical solid polymorphism: a supramolecular perspective. Adv Drug Deliv Rev. Feb. 23, 2004;56(3):241-74.

Rolan et al., "The pharmacokinetics, tolerability and pharmacodynamics of tucaresol (589C80); 4[2-formyl-3-hydroxyphenoxymethyl] benzoic acid), a potential anti-sickling agent, following oral administration to healthy subjects", British Journal of Clinical Pharmacology, 1993, 35(4):419-425.

Rooseboom et al., Enzyme-catalyzed activation of anticancer prodrugs. Pharmacol. Rev. 2004, 56:53-102.

Ruchirawat et al., "A novel synthesis of aporhoeadanes", Tetrahedron Letters (1984), 25(32), 3485-8 CODEN: TELEAY; ISSN: 0040-4039.

Safo, et al. Structural basis for the potent antisickling effect of a novel class of five-membered heterocyclic aldehydic compounds. J Med Chem. Sep. 9, 2004;47(19):4665-76.

(56) References Cited

OTHER PUBLICATIONS

Sahakitpichan et al., "A practical and highly efficient synthesis of lennoxamine and related isoindoloenzazepines" Tetrahedron (2004), 60(19), 4169-4172 CODEN: TETRAB; ISSN: 0040-4020.
Sahm et al., "Synthesis of 2-arylbenzofurans" Justus Liebigs Annalen der Chemie (1974), (4), 523-38 CODEN: JLACBF; ISSN: 0075-4617.
Sainsbury et al., "1,2-Dihydroisoquinolines, IV. Acylation" Tetrahedron (1966), 22(8), 2445-52 CODEN: TETRAB; ISSN: 0040-4020.
Sarodnick et al., "Quinoxalines XV, Convenient Synthesis and Structural Study of Pyrazolo[1,5-a]quinoxalines", Journal of Organic Chemistry (2009), 74(3), 1282-1287 CODEN: JOCEAH; ISSN: 0022-3263.
Schudel, et al. Uber die Chemie des Vitamins E. Helvetica Chimica Acta. 1963; 66:636-649.
Seddon. Pseudopolymorph: A Polemic. The QUILL Centre, The Queen's University of Belfast, United Kingdom. Jul. 26, 2004. 2 pages.
Shetty et al. Palladium catalyzed alpha-arylation of methyl isobutyrate and isobutyronitrile: an efficient synthesis of 2,5-disubstituted benzyl alcohol and amine intermediates. Tetrahedron Letters, 47:8021-8024 (2006).
Siddiqui et al., "The Presence of Substitutents on the Aryl Moiety of the Aryl Phosphoramidate Derivative of d4T Enhances Anti-HIV Efficacy in Cell Culture-Activity Relationship," J. Med. Chem., (1999), 42:393-399.
Silva et al., "Advances in prodrug design," Mini Rev. Med. Chem., (2005), 5(10):893-914.
Singh et al., "Reductive-Cyclization-Mediated Synthesis of Fused Polycyclic Quinolines from Baylis-Hillman Adducts of Acrylonitrile: Scope and Limitations", European Journal of Organic Chemistry (2009), (20), 3454-3466 CODEN: EJOCFK; ISSN:1434-193X.
Singhal, et al., "Drug Polymorphism and Dosage Form Design: a Practical Perspective" Advanced Drug Delivery reviews 56, p. 335-347 (2004).
Sobolev et al., Effect of acyl chain length and branching on the enantioselectivity of Candida rugosa lipase in the kinetic resolution of 4-(2-difluoromethoxyphenyl)-substituted 1,4-dihydropyridine 3,5-diesters. J. Org. Chem. 2002, 67:401-410.
Srivastava et al., "Synthesis and biological evaluation of 4-substituted tetrazolo[4,5-a]quinolines and 2,3-disubstituted quinoline derivatives", Indian Journal of Chemistry, Section B: Organic Chemistry Including Medicinal Chemistry (1989), 28B(7), 562-73 CODEN: IJSBOB; ISSN:0376-4699.
Starke et al., "Quinoxalines, Part 13: Synthesis and mass spectrometric study of aryloxymethylquinoxalines and benzo[b]furylquinoxalines" Tetrahedron (2004), 60(29), 6063-6078 CODEN: TETRAB; ISSN:0040-4020.
Stetinova, et al. Synthesis and Properties of 4-Alkylaminomethyl and 4-Alkoxymethyl Derivatives of 5-Methyl-2-Furancarboxylic Acid. Collection Czechosloval Chem. Commun. 1985; 51:2186-2192.
STN Registry Database Entry: CAS RN 1039927-57-5 (Entered STN: Aug. 20, 2008).
STN Registry Database Entry: CAS RN 1243541-58-3 (Entered STN: Sep. 29, 2010).
Strickley. Solubilizing excipients in oral and injectable formulations. Pharm Res. Feb. 2004;21(2):201-30.
Swann et al., "Rates of reductive elimination of substituted nitrophenols from the (indol-3-yl)methyl position of indolequinones", Journal of the Chemical Society, Perkin Transactions 2 (2001), (8), 1340-1345. Table of Compounds, each of which can be found either in Table 1 of U.S. Pat. No. 9,018,210 or Table 1 of U.S. Pat. No. 9,012,450.
Taday, et al., "Using Terahertz Pulse Spectroscopy to Study the Crystalline Structure of a Drug: A Case Study of the Polymorphs of Ranitidine Hydrochloride." J of Pharm. Sci., 92(4), 2003, 831-838.

Testa et al., Hydrolysis in Drug and Prodrug Metabolism, Jun. 2003, Wiley-VCH, Zurich, 419-534.
Tome et al., "Product class 13: 1,2,3-triazoles", Science of Synthesis (2004), 13, 415-601 CODEN: SSCYJ9.
Tsuge, et al. Suppressive Effect of Vitamin B6-Sugar Derivatives on the Proliferation of Feline Mammary Tumor Cell, FRM. Vitamins (Japan), 2006; 80(11):537-542. (in Japanese with English Abstract).
U.S. Pharmacopia #23, National Formulary #18, 1995, 1843-1844.
Van Halbeek, et al., "Sialic Acid in Permethylation Analysis: Prepared and Identification of Partially O-Methylated Derivatives of methyl N-Acetyl-N-Methyl-beta-D-Neurominate Methyl Glycoside", Carbohydrate Research, vol. 60, No. 1, 1978, pp. 51-62, 53, and 59.
VanRompaey et al., "A versatile synthesis of 2-substituted 4-amino-1,2,4,5-tetrahydro-2-benzazepine-3-ones", Tetrahedron (2003), 59(24), 4421-4432 CODEN: TETRAB; ISSN:0040-4020.
VanRompaey et al., "Synthesis and evaluation of the 3B2-turn properties of 4-amino-1,2,4,5-tetrahydro-2-benzazepin-3-ones and of their spirocyclic derivative", European Journal of Organic Chemistry (2006), (13), 2899-2911 CODEN: EJOCFK; ISSN: 1434-193X.
Vicente et al., "Carbopalladation of Maleate and Fumarate Esters and 1,1-Dimethylallene with Ortho-Substituted Aryl Palladium Complexes" Organometallics (2010), 29(2), 409-416.
Vichinsky. "Emerging 'A' therapies in hemoglobinopathies: agonists, antagonists, antioxidants, and arginine." Hematology 2012, 271-275.
Vippagunta, et al. Crystalline Solids. Advanced Drug Delivery Reviews. 2001; 48:3-26.
Wang et al., "Studies of Benzothiophene Template as Potent Factor IXa (FIXa) Inhibitors in Thrombosis", Journal of Medicinal Chemistry (2010), 53, 1465-1472.
Warshawsky et al., "The synthesis of aminobenzazespinones as anti-phenylalanine dipeptide mimics and their use in NEP inhibition", Bioorganic & Medicinal Chemistry Letter (1996), 6(8), 957-962 CODEN: BMCLE8; ISSN: 0960-894X.
Wendt et al., "Synthesis and SAR of 2-aryl pyrido[2,3-d]pyrimidines as potent mGlu5 receptor antagonists", Bioorganic & Medicinal Chemistry Letters, Pergamon, Amsterdam, NL, vol. 17, No. 19, Sep. 14, 2007 (Sep. 14, 2007), pp. 5396-5399.
Wermuth, Camille G., "Molecular Variations Based on Isosteric Replacements", The Practice of Medicinal Chemistry, 1996, pp. 203-232.
Yan et al., "Synthesis, crystal structure and antibacterial activity of dibutylitin carboxylate", Huaxue Tongbao (2007), 70(4), 313-316 CODEN: HHTPAU; ISSN: 0441-3776.
Yan et al., "Synthesis, crystal structure and antibacterial activity of di-n-butyltin di-2(2-formylphenoxy)acetic ester", Yingyong Huaxue (2007), 24(6), 660-664.
Yang, et al. Structural requirement of chalcones for the inhibitory activity of interleukin-5. Bioorg Med Chem. Jan. 1, 2007;15(1):104-11. Epub Oct. 10, 2006.
Yoon et al., The Chirality Conversion Reagent for Amino Acids Based on Salicyl Aldehyde. Bull. Korean Chem. Soc., (2012), 33:1715-1718.
Zhang et al., "DFT study on Rull-catalyzed cyclization of terminal alkynals to cycloalkenes", International Journal of Quantum Chemistry (2009), 109(4), 679-687 CODEN: IJQCB2; ISSN:0020-7608.
Zhang, et al. A selective fluorescent chemosensor with 1, 2, 4-triazole as subunit for Cu (II) and its application in imaging Cu (II) in living cells. Dyes and Pigments. 2012; 92(3):1370-1375.
Zhang, et al. Current prodrug strategies for improving oral absorption of nucleoside analogues. Asian Journal of Pharmaceutical Sciences. Apr. 2014; 9(2):65-74.
Zhu et al., "Isoquinoline-pyridine-based protein kinase B/Akt antagonists: SAR and in vivo antitumor activity", Bioorganic & Medicinal Chemistry Letters, Pergamon, Amsterdam, NL, 2006, vol. 16, No. 12, pp. 3150-3155.
Zwaagstra et al., "Synthesis and Structure-Activity Relationships of Carboxylated Chalcones: A Novel Series of Cys-LT1 (LTD4) Receptor Antagonists", Journal of Medicinal Chemistry (1997), 40(7), 1075-1089 CODEN: JMCMAR; ISSN: 0022-2623.

| | |
|---|---|
| Bravais Type | Primitive Monoclinic |
| a [Å] | 7.760 |
| b [Å] | 31.978 |
| c [Å] | 7.177 |
| α [deg] | 90 |
| β [deg] | 100.16 |
| γ [deg] | 90 |
| Volume [Å³/cell] | 1,753.0 |
| Chiral Contents? | Achiral |
| Extinction Symbol | P 1 2$_1$/c 1 |
| Space Group(s) | P2$_1$/c (14) |
| Source | Manual Input |

| Bravais Type | Triclinic | Triclinic |
|---|---|---|
| a [Å] | 7.966 | 7.966 |
| b [Å] | 11.726 | 11.891 |
| c [Å] | 11.891 | 12.031 |
| α [deg] | 61.25 | 121.30 |
| β [deg] | 86.34 | 99.19 |
| γ [deg] | 76.79 | 93.66 |
| Volume [Å³/cell] | 946.7 | 946.6 |
| Chiral Contents? | Achiral | Achiral |
| Extinction Symbol | P - | P - |
| Space Group(s) | P1 (1), P1̄ (2) | P1 (1), P1̄ (2) |
| Source | Manual Input | Manual Input |

| Bravais Type | Triclinic | Triclinic |
|---|---|---|
| a [Å] | 7.971 | 7.971 |
| b [Å] | 11.901 | 11.901 |
| c [Å] | 11.914 | 12.131 |
| α [deg] | 61.25 | 120.57 |
| β [deg] | 75.84 | 99.94 |
| γ [deg] | 86.05 | 93.95 |
| Volume [Å³/cell] | 959.2 | 959.2 |
| Chiral Contents? | Achiral | Achiral |
| Extinction Symbol | P - | P - |
| Space Group(s) | P1 (1), P1̄ (2) | P1 (1), P1̄ (2) |
| Source | Manual Input | Manual Input |

| Bravais Type | Triclinic | Triclinic |
|---|---|---|
| a [Å] | 8.005 | 8.005 |
| b [Å] | 11.676 | 11.812 |
| c [Å] | 11.812 | 11.974 |
| α [deg] | 61.30 | 121.21 |
| β [deg] | 85.79 | 98.35 |
| γ [deg] | 77.10 | 94.21 |
| Volume [Å³/cell] | 943.2 | 943.2 |
| Chiral Contents? | Achiral | Achiral |
| Extinction Symbol | P - | P - |
| Space Group(s) | P1 (1), P$\bar{1}$ (2) | P1 (1), P$\bar{1}$ (2) |
| Source | Manual Input | Manual Input |

| Bravais Type | Triclinic | Triclinic |
|---|---|---|
| a [Å] | 8.067 | 8.067 |
| b [Å] | 11.820 | 11.820 |
| c [Å] | 11.935 | 12.096 |
| α [deg] | 61.22 | 120.14 |
| β [deg] | 75.17 | 99.57 |
| γ [deg] | 84.93 | 95.07 |
| Volume [Å³/cell] | 963.4 | 963.4 |
| Chiral Contents? | Achiral | Achiral |
| Extinction Symbol | P - | P - |
| Space Group(s) | P1 (1), P$\bar{1}$ (2) | P1 (1), P$\bar{1}$ (2) |
| Source | Manual Input | Manual Input |

| Bravais Type | C-Centered Orthorhombic | Primitive Monoclinic |
| --- | --- | --- |
| a [Å] | 13.561 | 13.801 |
| b [Å] | 21.137 | 13.560 |
| c [Å] | 13.790 | 21.138 |
| α [deg] | 90 | 90 |
| β [deg] | 90 | 90.08 |
| γ [deg] | 90 | 90 |
| Volume [Å³/cell] | 3,952.8 | 3,955.8 |
| Chiral Contents? | Not Specified | Not Specified |
| Extinction Symbol | C c - - | P 1 $2_1$/n 1 |
| Space Group(s) | Ccm$2_1$ (36)*, Cc2m (40)*, Ccmm (63)* | P$2_1$/n (14) |
| Source | Triads Algorithm | Manual Input |

\* = Unconventional space group setting.

CRYSTALLINE POLYMORPHS OF THE FREE BASE OF 2-HYDROXY-6-((2-(1-ISOPROPYL-1H-PYRAZOL-5-YL)PYRIDIN-3-YL)METHOXY) BENZALDEHYDE

CROSS-REFERENCE TO RELATED APPLICATIONS

This application is a continuation application of U.S. patent application Ser. No. 15/236,283 filed Aug. 12, 2016, which is a continuation application of U.S. patent application Ser. No. 14/616,548, filed Feb. 6, 2015, now U.S. Pat. No. 9,447,071, issued Sep. 20, 2016, which claims priority to U.S. Provisional Application No. 61/937,393 filed Feb. 7, 2014, and U.S. Provisional Application No. 61/937,404 filed Feb. 7, 2014, the contents of each of which is incorporated herein in its entirety by reference.

BACKGROUND

2-Hydroxy-6-((2-(1-isopropyl-1H-pyrazol-5-yl)pyridin-3-yl)methoxy)benzaldehyde is a compound having the formula:

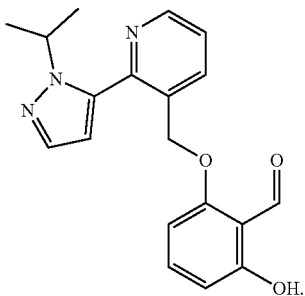 [SMILES: CC(C)n1nccc1-c1ncccc1COc1cccc(O)c1C=O]

Sickle cell disease is a disorder of the red blood cells, found particularly among those of African and Mediterranean descent. The basis for sickle cell disease is found in sickle hemoglobin (HbS), which contains a point mutation relative to the prevalent peptide sequence of hemoglobin (Hb).

Hemoglobin (Hb) transports oxygen molecules from the lungs to various tissues and organs throughout the body. Hemoglobin binds and releases oxygen through conformational changes. Sickle hemoglobin (HbS) contains a point mutation where glutamic acid is replaced with valine, allowing HbS to become susceptible to polymerization to give the HbS containing red blood cells their characteristic sickle shape. The sickled cells are also more rigid than normal red blood cells, and their lack of flexibility can lead to blockage of blood vessels. A need exists for therapeutics that can treat disorders that are mediated by Hb or by abnormal Hb such as HbS, such as 2-hydroxy-6-((2-(1-isopropyl-1H-pyrazol-5-yl)pyridin-3-yl)methoxy)benzaldehyde.

When used for treating humans, it is important that a crystalline form of a therapeutic agent, like 2-hydroxy-6-((2-(1-isopropyl-1H-pyrazol-5-yl)pyridin-3-yl)methoxy) benzaldehyde, or a salt thereof, retains its polymorphic and chemical stability, solubility, and other physicochemical properties over time and among various manufactured batches of the agent. If the physicochemical properties vary with time and among batches, the administration of a therapeutically effective dose becomes problematic and may lead to toxic side effects or to ineffective therapy, particularly if a given polymorph decomposes prior to use, to a less active, inactive, or toxic compound. Therefore, it is important to choose a form of the crystalline agent that is stable, is manufactured reproducibly, and has physicochemical properties favorable for its use as a therapeutic agent.

However, the art remains unable to predict which crystalline form of an agent will have a combination of the desired properties and will be suitable for human administration, and how to make the agent in such a crystalline form.

SUMMARY

Ansolvates

This invention arises in part out the discovery that an HCl salt of Compound 1 disproportionates or loses HCl, and a disproportionation of the HCl salt of Compound 1 in water generates the free base and disproportionation was facile upon exposure to elevated humidity, with wet milling, and in direct contact with water (e.g. slurry). The sulfate salt of Compound 1 also disproportionates from certain solvents such as dimethyl sulfoxide and methanol when precipitated with water. The volatilization of HCl was evident within hours of exposure to drying conditions. For example, partial conversion to the free base was observed within 12 hours at 30° C. Accordingly, the free base of Compound 1 provides a stabler chemical entity compared to the corresponding HCl or sulfate and such other salt.

It has now been discovered that 2-hydroxy-6-((2-(1-isopropyl-1H-pyrazol-5-yl)pyridin-3-yl)methoxy)benzaldehyde (or Compound 1) i.e., the free base of Compound 1, can be obtained as one or more crystalline ansolvate forms, several of which are referred to here as crystalline Form I, Form II and Material N. In preferred embodiments, the free base of Compound 1 is a crystalline ansolvate, such as a crystalline anhydrous form. The free base of Compound 1, can be obtained from its corresponding salt form, such as the HCl salt of Compound 1.

Three anhydrous crystalline forms of the free base were identified, termed Free Base Forms I, II, and Material N. It has been discovered that nucleation of Free Base Form I generally occurs first from a slurry. Extending the slurry time can induce the transformation of Free Base Form I to Free Base Form II, a thermodynamically more stable phase relative to Form I. It has further been discovered that Free Base Material N can be stable relative to Forms I and II, at room temperature.

Free Base Material N was found to be enantiotropically related to Form II, and will transform reversibly at a specific transition temperature (estimated herein near 40-42° C.). Above the transition temperature, Free Base Form II appears to be the most stable form, relative to Form I and Material N. Thus, under operating temperatures below 40° C., e.g., at 30° C., the free base of Compound 1 exists primarily as Material N, which may have some residual Form II. Thus, at operating temperatures above 40° C., e.g., at 50° C., the free base of Compound 1 exists primarily as Form II, which may have some residual Material N. At 40° C. little appreciable conversion is seen between Material N and Form II. This is contemplated to be true for slurries of the free base in certain solvents and in the solid state. In one embodiment, the one or more crystalline free base forms of Compound 1 do not undergo polymorphic transformation under conditions suitable for manufacturing and storing the crystalline forms.

Form I

In one embodiment, the crystalline free base of Compound 1 comprises crystalline Form I, which is characterized by an endothermic peak at (97±2) C as measured by differential scanning calorimetry. In another embodiment, the crystalline Form I of the free base of crystalline Compound 1 is characterized by the substantial absence of thermal events at temperatures below the endothermic peak at (97±2) ° C. as measured by differential scanning calorimetry. In another embodiment, the crystalline Form I of the free base of crystalline Compound 1 is characterized by an X-ray powder diffraction peak (Cu Kα radiation at one or more of 12.82°, 15.74°, 16.03°, 16.63°, 17.60°, 25.14°, 25.82° and 26.44°±0.2 °2θ. In another embodiment, the crystalline Form I of the free base of crystalline Compound 1 is characterized by an X-ray powder diffraction pattern (Cu Kα radiation) substantially similar to that of FIG. 3.

In another embodiment, the crystalline Form I of the free base of crystalline Compound 1 is characterized by at least one X-ray powder diffraction peak (Cu Kα radiation) selected from 12.82°, 15.74°, 16.03°, 16.63°, 17.60°, 25.14°, 25.82° and 26.44° (each ±0.2 °2θ). In another embodiment, the crystalline Form I of the free base of crystalline Compound 1 is characterized by at least two X-ray powder diffraction peaks (Cu Kα radiation) selected from 12.82°, 15.74°, 16.03°, 16.63°, 17.60°, 25.14°, 25.82° and 26.44° (each ±0.2 °2θ). In another embodiment, the crystalline Form I of the free base of crystalline Compound 1 is characterized by at least three X-ray powder diffraction peaks (Cu Kα radiation) selected from 12.82°, 15.74°, 16.03°, 16.63°, 17.60°, 25.14°, 25.82° and 26.44° (each ±0.2 °2θ).

In another embodiment, Form I is characterized by 1, 2, 3, 4, or more peaks as tabulated below.
Observed Peaks for Form I, XRPD File 609973.

| °2θ | d space (Å) | Intensity (%) |
| --- | --- | --- |
| 5.52 ± 0.20 | 16.021 ± 0.602 | 68 |
| 12.82 ± 0.20 | 6.906 ± 0.109 | 74 |
| 15.03 ± 0.20 | 5.897 ± 0.079 | 38 |
| 15.74 ± 0.20 | 5.629 ± 0.072 | 46 |
| 16.03 ± 0.20 | 5.530 ± 0.069 | 46 |
| 16.63 ± 0.20 | 5.331 ± 0.064 | 61 |
| 17.60 ± 0.20 | 5.040 ± 0.057 | 100 |
| 18.74 ± 0.20 | 4.736 ± 0.051 | 24 |
| 19.07 ± 0.20 | 4.654 ± 0.049 | 17 |
| 19.35 ± 0.20 | 4.587 ± 0.047 | 23 |
| 20.32 ± 0.20 | 4.370 ± 0.043 | 18 |
| 21.64 ± 0.20 | 4.106 ± 0.038 | 23 |
| 22.80 ± 0.20 | 3.901 ± 0.034 | 26 |
| 23.28 ± 0.20 | 3.821 ± 0.033 | 34 |
| 25.14 ± 0.20 | 3.543 ± 0.028 | 52 |
| 25.82 ± 0.20 | 3.451 ± 0.026 | 81 |
| 26.44 ± 0.20 | 3.371 ± 0.025 | 51 |
| 27.91 ± 0.20 | 3.197 ± 0.023 | 17 |
| 28.19 ± 0.20 | 3.165 ± 0.022 | 26 |

Form II

In another embodiment, the crystalline Compound 1 free base comprises crystalline Form II, which is characterized by an endothermic peak at (97±2) C as measured by differential scanning calorimetry. In another embodiment, the crystalline Form II of the free base of crystalline Compound 1 is characterized by the substantial absence of thermal events at temperatures below the endothermic peak at (97±2) ° C. as measured by differential scanning calorimetry. In another embodiment, the crystalline Form II of the free base of crystalline Compound 1 is characterized by an X-ray powder diffraction peak (Cu Kα radiation at one or more of 13.37°, 14.37°, 19.95° or 23.92° 2θ. In another embodiment, the crystalline Form II of the free base of crystalline Compound 1 is characterized by an X-ray powder diffraction pattern (Cu Kα radiation) substantially similar to that of FIG. 5.

In another embodiment, the crystalline Form II of the free base of crystalline Compound 1 is characterized by at least one X-ray powder diffraction peak (Cu Kα radiation) selected from 13.37°, 14.37°, 19.95° and 23.92 °2θ (each ±0.2 °2θ). In another embodiment, the crystalline Form II of the free base of crystalline Compound 1 is characterized by at least two X-ray powder diffraction peaks (Cu Kα radiation) selected from 13.37°, 14.37°, 19.95° and 23.92 °2θ (each ±0.2 °2θ). In another embodiment, the crystalline Form II of the free base of crystalline Compound 1 is characterized by at least three X-ray powder diffraction peaks (Cu Kα radiation) selected from 13.37°, 14.37°, 19.95° and 23.92 °2θ (each ±0.2 °2θ).

In another embodiment, Form II is characterized by 1, 2, 3, 4, or more peaks as tabulated below.
Observed Peaks for Form II, XRPD File 613881.

| °2θ | d space (Å) | Intensity (%) |
| --- | --- | --- |
| 5.62 ± 0.20 | 15.735 ± 0.581 | 24 |
| 12.85 ± 0.20 | 6.888 ± 0.108 | 22 |
| 12.97 ± 0.20 | 6.826 ± 0.106 | 21 |
| 13.37 ± 0.20 | 6.622 ± 0.100 | 100 |
| 14.37 ± 0.20 | 6.162 ± 0.087 | 56 |
| 15.31 ± 0.20 | 5.788 ± 0.076 | 21 |
| 16.09 ± 0.20 | 5.507 ± 0.069 | 23 |
| 16.45 ± 0.20 | 5.390 ± 0.066 | 69 |
| 16.75 ± 0.20 | 5.294 ± 0.064 | 32 |
| 16.96 ± 0.20 | 5.227 ± 0.062 | 53 |
| 19.95 ± 0.20 | 4.450 ± 0.045 | 39 |
| 20.22 ± 0.20 | 4.391 ± 0.043 | 20 |
| 23.18 ± 0.20 | 3.837 ± 0.033 | 38 |
| 23.92 ± 0.20 | 3.721 ± 0.031 | 41 |
| 24.40 ± 0.20 | 3.648 ± 0.030 | 44 |
| 24.73 ± 0.20 | 3.600 ± 0.029 | 22 |
| 24.99 ± 0.20 | 3.564 ± 0.028 | 50 |
| 25.12 ± 0.20 | 3.545 ± 0.028 | 28 |
| 25.39 ± 0.20 | 3.509 ± 0.027 | 51 |
| 25.70 ± 0.20 | 3.466 ± 0.027 | 21 |
| 26.19 ± 0.20 | 3.403 ± 0.026 | 27 |
| 26.72 ± 0.20 | 3.336 ± 0.025 | 30 |
| 27.02 ± 0.20 | 3.300 ± 0.024 | 25 |
| 27.34 ± 0.20 | 3.262 ± 0.024 | 23 |
| 28.44 ± 0.20 | 3.138 ± 0.022 | 20 |

In some embodiments, the free base of crystalline Compound 1 comprises the crystalline Form II. In some preferred embodiments, the free base of crystalline Compound 1 comprises the crystalline Form II and less than 25 mole %, 10 mole % or 5 mole % of crystalline Form I, crystalline Material N or amorphous forms of Compound 1.

In a preferred embodiment, the crystalline Form II is prepared from a slurry comprising the free base of Compound 1 in heptane, from which the crystalline Form II is formed and filtered. Thus, in some embodiments, the crystalline Form II comprises residual (1-500 ppm) heptane. In another preferred embodiment, the crystalline Form II is prepared from a slurry comprising the free base of Compound 1 in water, from which the crystalline Form II is formed and filtered.

There are several advantages of crystalline Form II relative to crystalline Form I or Material N. For example, the crystalline Form II can be prepared from a slurry comprising the free base of Compound 1 in heptane, which is suitable for good manufacturing practices (GMP) protocols. Further, in a most preferred embodiment, the crystalline Form II can be prepared from a slurry comprising the free base of Compound 1 in water or the HCl salt of Compound 1 in water, thus reducing or eliminating the need for solvent during recrystalization. Thus, in some embodiments, crystalline Form II of Compound 1 comprises less than 500 ppm, 100 ppm, less than 50 ppm or less than 10 ppm organic solvent. Also, Form II has less of a propensity than Material N to agglomerate upon size reduction, e.g., upon milling. As such, Form II has greater flowability than Material N. Certain illustrative and non-limiting advantages of Form II over Material N (i.e., Form N) are shown in the table below.

| DATA/EXPERIMENT | RESULTS/STATUS |
|---|---|
| Identify suitable solvent for scale-up | Form N:<br>Limited number of suitable solvents compared to Form II<br>MTBE identified (suitable for GMP; Class III solvent)<br>Scale-up results look good<br>Form II:<br>More solvent options than Form N, including H$_2$O<br>Current solvent is heptane (suitable for GMP; Class III solvent)<br>produced on 5 kg scale<br>Formation time faster than N (could translate to 2-3 day saving in production time)<br>Better recovery than N |
| Size/Morphology of N and II | Acicular morphology observed for form N; material composed of small and large particles<br>Agglomerates are an issue for Form N relative to Form II (less agglomeration seen with energy-reduced method) |
| PK Comparison of N and II | Oral administrations of GBT440 Forms N and II to rats resulted in comparable exposure at 100 & 500 mg/kg |

Material N

In another embodiment, the crystalline Compound 1 free base comprises crystalline Material N, which is characterized by an endothermic peak at (95±2) C as measured by differential scanning calorimetry. The terms "Material N", "form N" and "polymorphic form N" are used interchangeably herein. In another embodiment, the crystalline Material N of the free base of crystalline Compound 1 is characterized by the substantial absence of thermal events at temperatures below the endothermic peak at (95±2) ° C. as measured by differential scanning calorimetry. In another embodiment, the crystalline Material N of the free base of crystalline Compound 1 is characterized by an X-ray powder diffraction peak (Cu Kα radiation at one or more of 11.65°, 11.85°, 12.08°, 16.70°, 19.65° or 23.48 °2θ. In another embodiment, the crystalline Material N of the free base of crystalline Compound 1 is characterized by an X-ray powder diffraction pattern (Cu Kα radiation) substantially similar to that of FIG. 7.

In another embodiment, the crystalline Material N of the free base of crystalline Compound 1 is characterized by at least one X-ray powder diffraction peak (Cu Kα radiation) selected from 11.65°, 11.85°, 12.08°, 16.70°, 19.65° and 23.48 °2θ (each ±0.2 °2θ). In another embodiment, the crystalline Material N of the free base of crystalline Compound 1 is characterized by at least two X-ray powder diffraction peaks (Cu Kα radiation) selected from 11.65°, 11.85°, 12.08°, 16.70°, 19.65° and 23.48 °2θ (each ±0.2 °2θ). In another embodiment, the crystalline Material N of the free base of crystalline Compound 1 is characterized by at least three X-ray powder diffraction peaks (Cu Kα radiation) selected from 11.65°, 11.85°, 12.08°, 16.70°, 19.65° and 23.48 °2θ (each ±0.2 °2θ).

In another embodiment, Material N is characterized by 1, 2, 3, 4, or more peaks as tabulated below.

Observed Peaks for Material N, XRPD File 615765.

| °2θ | d space (Å) | Intensity (%) |
|---|---|---|
| 5.55 ± 0.20 | 15.924 ± 0.595 | 54 |
| 11.65 ± 0.20 | 7.597 ± 0.132 | 31 |
| 11.85 ± 0.20 | 7.468 ± 0.128 | 50 |
| 12.08 ± 0.20 | 7.324 ± 0.123 | 31 |
| 12.67 ± 0.20 | 6.987 ± 0.112 | 29 |
| 13.12 ± 0.20 | 6.748 ± 0.104 | 83 |
| 14.94 ± 0.20 | 5.929 ± 0.080 | 34 |
| 15.19 ± 0.20 | 5.832 ± 0.077 | 56 |
| 15.76 ± 0.20 | 5.623 ± 0.072 | 20 |
| 16.70 ± 0.20 | 5.310 ± 0.064 | 100 |
| 17.35 ± 0.20 | 5.112 ± 0.059 | 52 |
| 19.65 ± 0.20 | 4.517 ± 0.046 | 60 |
| 23.48 ± 0.20 | 3.789 ± 0.032 | 72 |
| 23.68 ± 0.20 | 3.757 ± 0.032 | 29 |
| 25.25 ± 0.20 | 3.527 ± 0.028 | 20 |
| 25.47 ± 0.20 | 3.497 ± 0.027 | 20 |
| 25.70 ± 0.20 | 3.466 ± 0.027 | 85 |
| 26.04 ± 0.20 | 3.422 ± 0.026 | 35 |
| 26.37 ± 0.20 | 3.380 ± 0.025 | 55 |

In some embodiments, the free base of crystalline Compound 1 comprises the crystalline Material N and less than 25 mole %, 10 mole % or 5 mole % of crystalline Forms I or II or amorphous forms of Compound 1.

In another embodiment, the crystalline Material N is prepared from a slurry comprising the free base of Compound 1 in methyl tertiary butyl ether (MTBE), from which the crystalline-Material N is formed and filtered. Thus, in some embodiments, the crystalline Material N comprises residual (1-500 ppm) MTBE.

There are several advantages of crystalline Material N relative to crystalline Forms I or II. For example, the crystalline Material N can be prepared from a slurry comprising the free base of Compound 1 in MTBE, which is suitable for good manufacturing practices (GMP) protocols.

In some embodiments, the crystalline ansolvate forms are stable to contact with water, heptane, iso propyl ether (IPE), MTBE, and toluene, and such other solvents.

In another of its composition embodiments, this invention provides for a pharmaceutical composition comprising a pharmaceutically acceptable excipient and a crystalline Compound 1 free base, comprising one or more of Form I, Form II or Material N.

In one of its method embodiments, this invention provides a method of preparing the solid crystalline free base of Compound 1 comprising, e.g., Form I, Form II and/or Material N.

In yet another of its method embodiments, there are provided methods for increasing oxygen affinity of hemoglobin S in a subject, the method comprising administering to a subject in need thereof a therapeutically effective amount of a crystalline free base of Compound 1, comprising, e.g., Form I, Form II and/or Material N.

In yet another of its method embodiments, there are provided methods for treating oxygen deficiency associated with sickle cell anemia in a subject, the method comprising administering to a subject in need thereof a therapeutically effective amount of a crystalline free base of Compound 1, comprising, e.g., Form I, Form II and/or Material N.

In all of such treatments, the effective amount of free base of Compound 1, comprising e.g., Form I, Form II and/or Material N to the treated patient is already disclosed in the art.

Solvates

This invention arises in part out of the discovery that ansolvate polymorphs of the free base of Compound 1 form solvate polymorphs with a variety of solvents, preferably other than certain hydrocarbon solvents, water and ethers.

Solvates of the crystalline free base of Compound 1 (e.g., from acetone, acetonitrile, dichloromethane, dioxane, ethanol, ethyl acetate, isopropyl alcohol, methyl ethyl ketone (MEK) and tetrahydrofuran) are also contemplated to be used e.g., as intermediates to regenerate the free base crystalline ansolvate of Compound 1. Such methods can include, without limitation, subjecting the solvate to vacuum conditions; and/or generating a salt and disproportionating it in water to form the ansolvate; and/or slurrying or washing the solvate with a solvent less prone to solvate formation such as heptane, di-isopropyl ether (IPE), tert-methyl butyl ether (MTBE) and toluene.

In another of its composition embodiments, this invention provides for a pharmaceutical composition comprising a pharmaceutically acceptable excipient and one or more of the solvated crystal forms provided herein.

In one of its method embodiments, this invention provides a method of preparing the solvated crystal forms provided herein.

In yet another of its method embodiments, there are provided methods for increasing oxygen affinity of hemoglobin S in a subject, the method comprising administering to a subject in need thereof a therapeutically effective amount of one or more of the solvated crystal forms provided herein.

In yet another of its method embodiments, there are provided methods for treating oxygen deficiency associated with sickle cell anemia in a subject, the method comprising administering to a subject in need thereof a therapeutically effective amount of one or more of the solvated crystal forms provided herein.

In all of such treatments, the effective amount of the free base of Compound 1, to the treated patient is already disclosed in the art.

DETAILED DESCRIPTION

Figure 1:
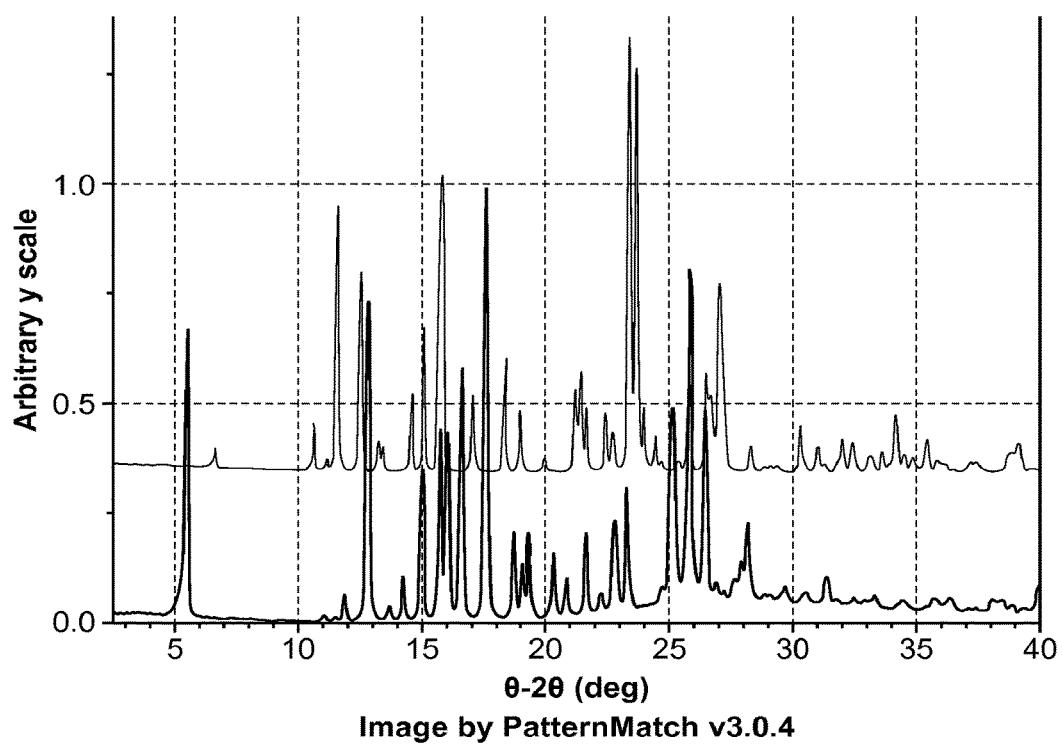
FIG. 1 is a XRPD profile of the crystalline HCl salt before (top) and after (bottom) 5 minutes slurried in water.

As noted above, this invention is directed, in part, to a stable free base of Compound 1 and, in particular, the free base Form I, Form II or Material N. However, prior to discussing this invention in further detail, the following terms will be defined.

Definitions

As used herein, the following terms have the following meanings.

The singular forms "a," "an," and "the" and the like include plural referents unless the context clearly dictates otherwise. Thus, for example, reference to "a compound" includes both a single compound and a plurality of different compounds.

The term "about" when used before a numerical designation, e.g., temperature, time, amount, and concentration, including a range, indicates approximations which may vary by ±10%, ±5% or ±1%.

"Administration" refers to introducing an agent into a patient. A therapeutic amount can be administered, which can be determined by the treating physician or the like. An oral route of administration is preferred. The related terms and phrases administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient. In any event, administration entails delivery to the patient of the drug.

The "crystalline ansolvate" of Compound 1 is a crystalline solid form of the free base of 2-hydroxy-6-((2-(1-isopropyl-1H-pyrazol-5-yl)pyridin-3-yl)methoxy)benzaldehyde, such as, e.g., crystalline Form I, Form II or Material N as disclosed herein. Each of the Form I, Form II or Material N crystal lattices is substantially free of solvents of crystallization. However, any solvent present is not included in the crystal lattice and is randomly distributed outside the crystal lattice. Therefore, Form I, Form II or Material N crystals in bulk may contain, outside the crystal lattice, small amounts of one or more solvents, such as the solvents used in its synthesis or crystallization. As used above, "substantially free of" and "small amounts," refers to the presence of solvents preferably less that 10,000 parts per million (ppm), or more preferably, less than 500 ppm.

The "crystalline solvate" of Compound 1 is a crystalline solid form of the free base of 2-hydroxy-6-((2-(1-isopropyl-1H-pyrazol-5-yl)pyridin-3-yl)methoxy)benzaldehyde, where the crystal lattices comprises one or more solvents of crystallization.

"Characterization" refers to obtaining data which may be used to identify a solid form of a compound, for example, to identify whether the solid form is amorphous or crystalline and whether it is unsolvated or solvated. The process by which solid forms are characterized involves analyzing data collected on the polymorphic forms so as to allow one of ordinary skill in the art to distinguish one solid form from other solid forms containing the same material. Chemical identity of solid forms can often be determined with solution-state techniques such as $^{13}$C NMR or $^1$H NMR. While these may help identify a material, and a solvent molecule for a solvate, such solution-state techniques themselves may not provide information about the solid state. There are, however, solid-state analytical techniques that can be used to provide information about solid-state structure and differentiate among polymorphic solid forms, such as single crystal X-ray diffraction, X-ray powder diffraction (XRPD), solid state nuclear magnetic resonance (SS-NMR), and infrared and Raman spectroscopy, and thermal techniques such as differential scanning calorimetry (DSC), Solid state $^{13}$C-NMR, thermogravimetry (TG), melting point, and hot stage microscopy.

To "characterize" a solid form of a compound, one may, for example, collect XRPD data on solid forms of the compound and compare the XRPD peaks of the forms. For example, when only three solid forms, e.g., Forms I and II and Material N, are compared and the Form I pattern shows a peak at an angle where no peaks appear in the Form II or Material N pattern, then that peak, for that compound, distinguishes Form I from Form II and Material N and further acts to characterize Form I. The collection of peaks which distinguish e.g., Form I from the other known forms is a collection of peaks which may be used to characterize Form I. Those of ordinary skill in the art will recognize that there are often multiple ways, including multiple ways using the same analytical technique, to characterize solid forms. Additional peaks could also be used, but are not necessary, to characterize the form up to and including an entire diffraction pattern. Although all the peaks within an entire XRPD pattern may be used to characterize such a form, a subset of that data may, and typically is, used to characterize the form.

An XRPD pattern is an x-y graph with diffraction angle (typically °2θ) on the x-axis and intensity on the y-axis. The peaks within this pattern may be used to characterize a crystalline solid form. As with any data measurement, there is variability in XRPD data. The data are often represented solely by the diffraction angle of the peaks rather than including the intensity of the peaks because peak intensity can be particularly sensitive to sample preparation (for example, particle size, moisture content, solvent content, and preferred orientation effects influence the sensitivity), so samples of the same material prepared under different conditions may yield slightly different patterns; this variability is usually greater than the variability in diffraction angles. Diffraction angle variability may also be sensitive to sample preparation. Other sources of variability come from instrument parameters and processing of the raw X-ray data: different X-ray instruments operate using different parameters and these may lead to slightly different XRPD patterns from the same solid form, and similarly different software packages process X-ray data differently and this also leads to variability. These and other sources of variability are known to those of ordinary skill in the pharmaceutical arts. Due to such sources of variability, it is usual to assign a variability of ±0.2 °2θ to diffraction angles in XRPD patterns.

"Comprising" or "comprises" is intended to mean that the compositions and methods include the recited elements, but not exclude others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Form II and Material N are enantiotropic at a transition temperature (of approximately 42° C.). Below this transition temperature, Material N of the free base of Compound 1 is the thermodynamically more stable form relative to Forms I and II. Above this transition temperature, Form II of the free base of Compound 1 is the thermodynamically more stable form relative to Form I and Material N.

"Room temperature" refers to (22±5) ° C.

"Therapeutically effective amount" or "therapeutic amount" refers to an amount of a drug or an agent that when administered to a patient suffering from a condition, will have the intended therapeutic effect, e.g., alleviation, amelioration, palliation or elimination of one or more manifestations of the condition in the patient. The therapeutically effective amount will vary depending upon the subject and the condition being treated, the weight and age of the subject, the severity of the condition, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of an agent, in the context of treating disorders related to hemoglobin S, refers to an amount of the agent that alleviates, ameliorates, palliates, or eliminates one or more manifestations of the disorders related to hemoglobin S in the patient.

"Treatment", "treating", and "treat" are defined as acting upon a disease, disorder, or condition with an agent to reduce or ameliorate the harmful or any other undesired effects of the disease, disorder, or condition and/or its symptoms. Treatment, as used herein, covers the treatment of a human patient, and includes: (a) reducing the risk of occurrence of the condition in a patient determined to be predisposed to the disease but not yet diagnosed as having the condition, (b) impeding the development of the condition, and/or (c) relieving the condition, i.e., causing regression of the condition and/or relieving one or more symptoms of the condition. For purposes of this invention, beneficial or desired clinical results include, but are not limited to, multilineage hematologic improvement, decrease in the number of required blood transfusions, decrease in infections, decreased bleeding, and the like.

Identifying Forms I, II and Material N

When the HCl salt of Compound 1 was subjected to various stress conditions, disproportionation of the HCl salt in water was observed to generate the free base. At least three anhydrous crystalline forms of the free base were identified, termed Free Base Forms I, II, and Material N. It was discovered that nucleation of Free Base Form I generally occurs first and that extending the slurry time induces the transformation of Free Base Form I to Free Base Form II, a more thermodynamically stable phase relative to Form I. It was further discovered that Free Base Material N appears to be most stable form, relative to Forms I and II, at room temperature. Free Base Material N was found to be enantiotropically active relative to Form II, and will transform reversibly at a specific transition temperature (estimated herein near 42° C.). Above the transition temperature, Free Base Form II appears to be the most stable form, relative to Form I and Material N.

Figure 10:
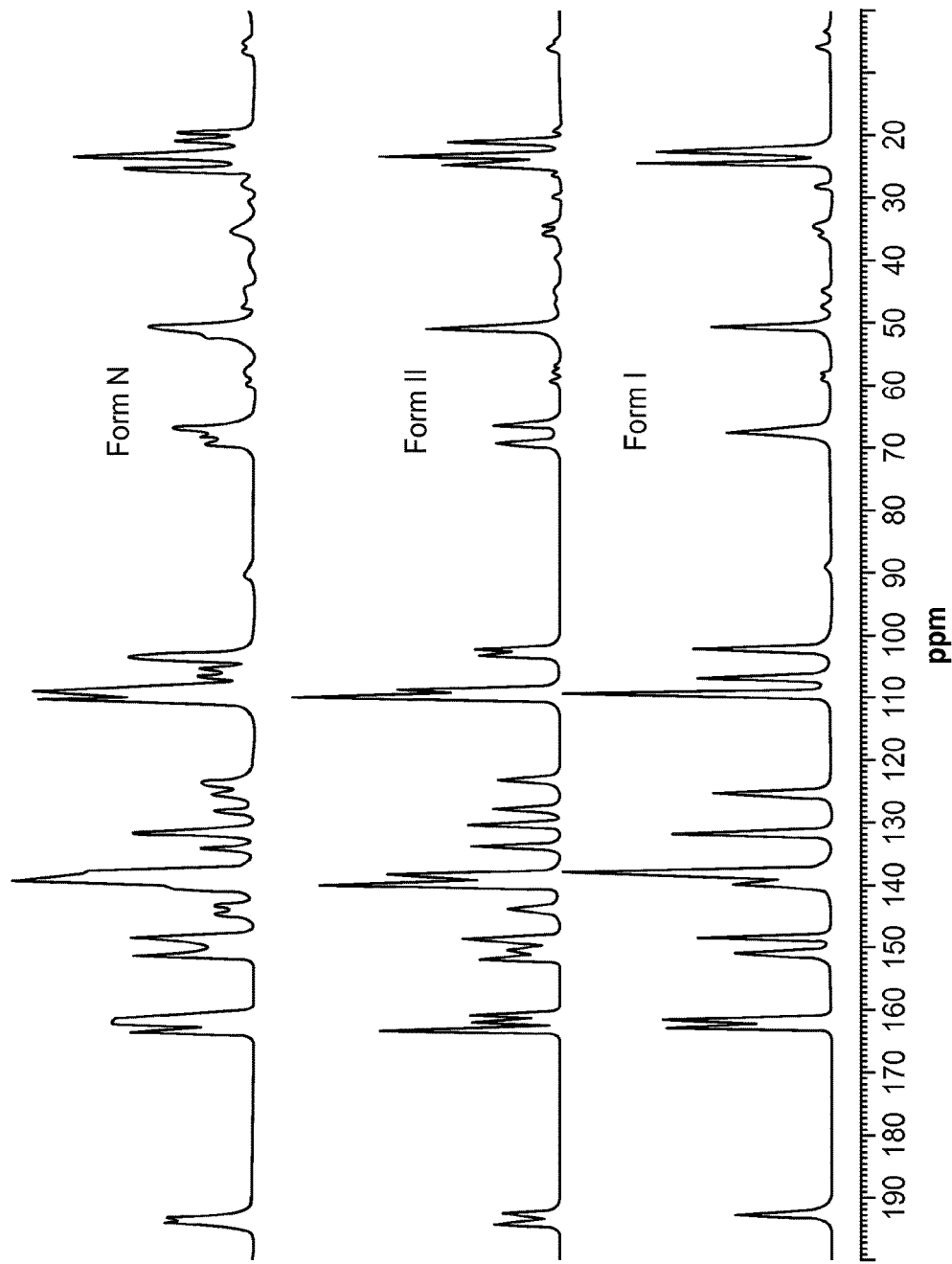
FIG. 10 depicts $^{13}$C Solid State NMR spectra for Free Base Forms I (bottom), II (middle), and Material N (top). Form I contains one molecule per asymmetric unit. Material N contains four molecules per asymmetric unit. As observed by $^{13}$C Solid State NMR spectra, Forms II and N did not undergo a transition over 250 K to 340 K. Chemical shifts change slightly with temperature (not illustrated graphically).
Figure 11:
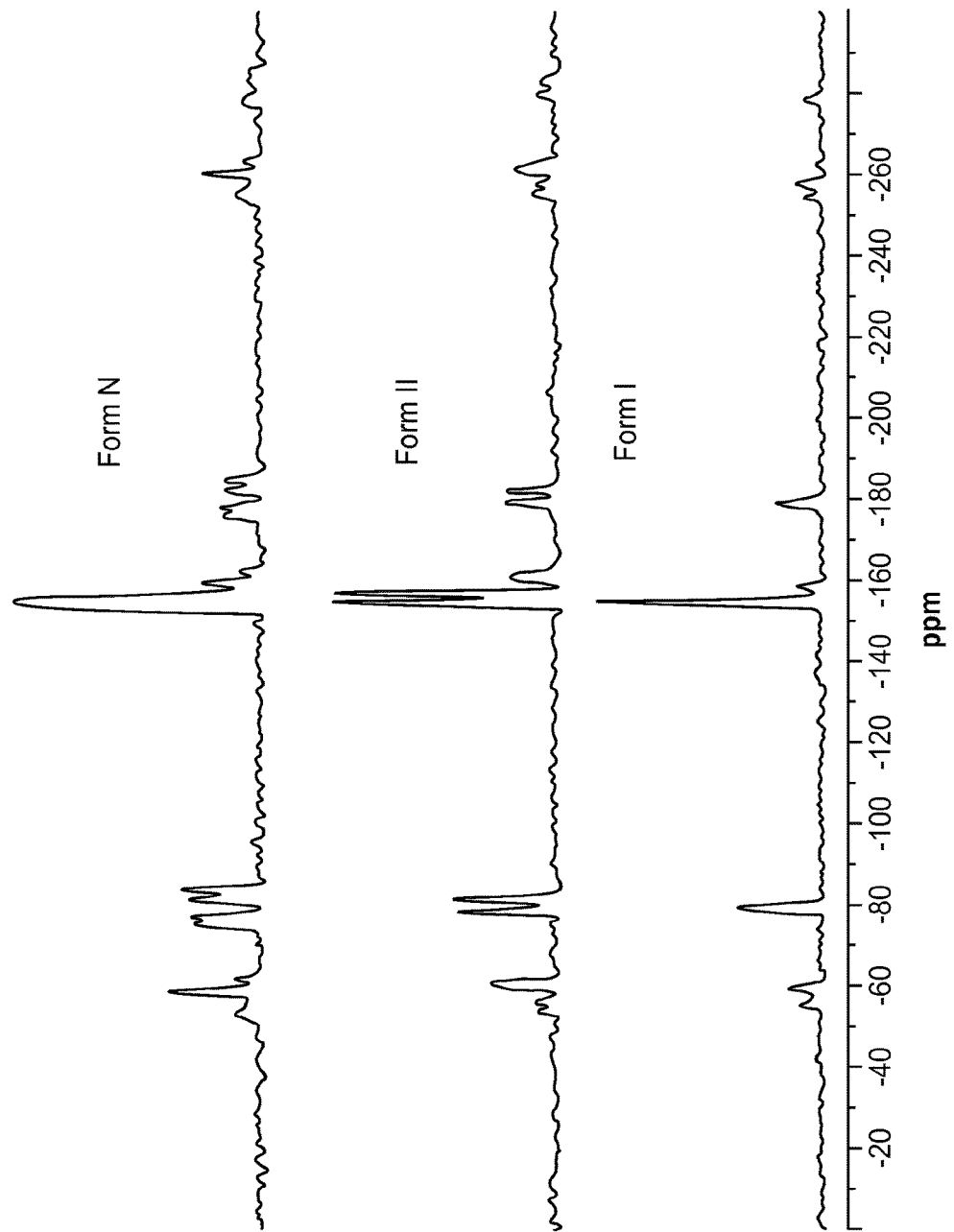
FIG. 11 depicts $^{15}$N Solid State NMR spectra for Free Base Forms I (bottom), II (middle), and Material N (top).
Figure 12:
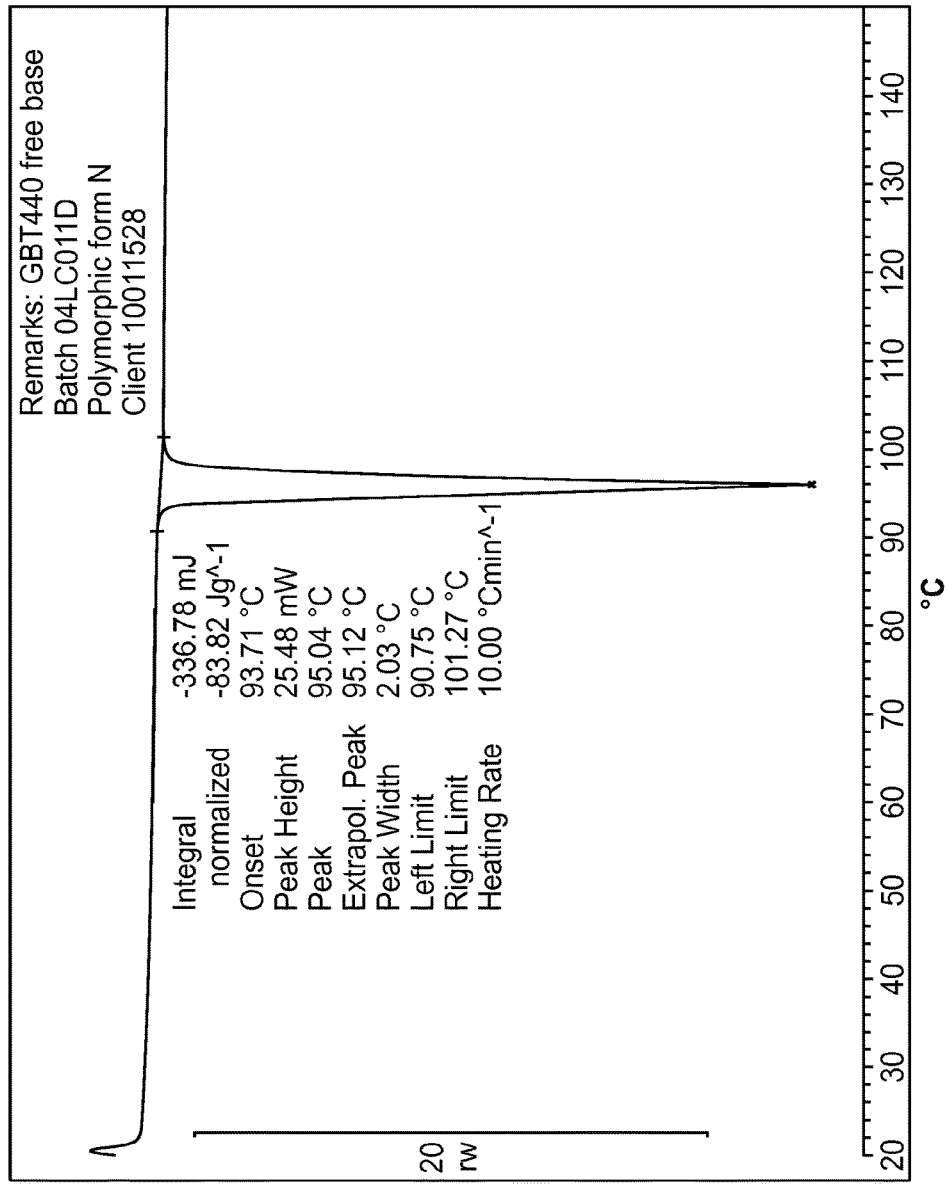
FIG. 12 depicts a differential scanning calorimetry (DSC) curve for Free Base Material N.
Figure 13:
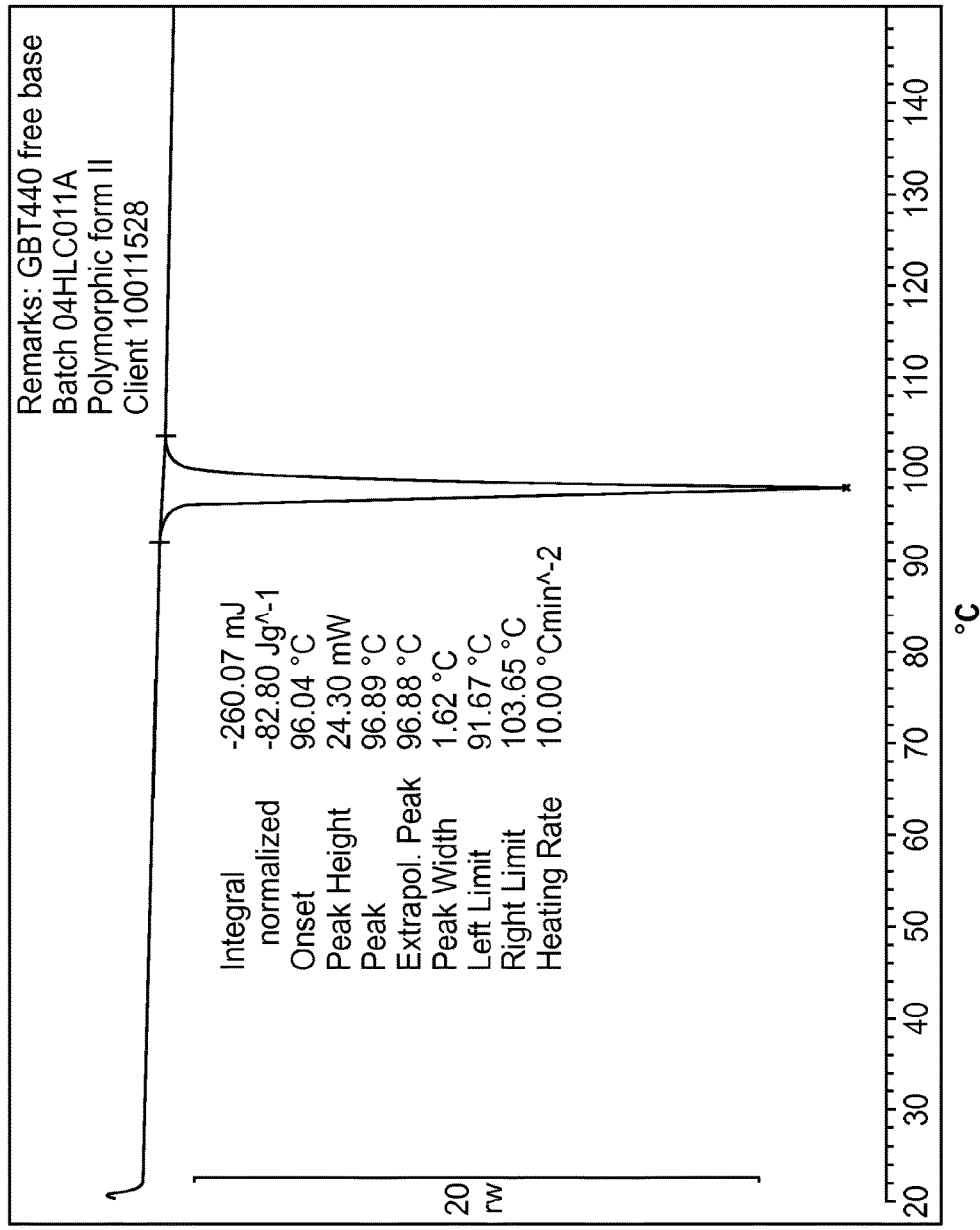
FIG. 13 depicts a DSC curve for Free Base Form II.
Figure 14:
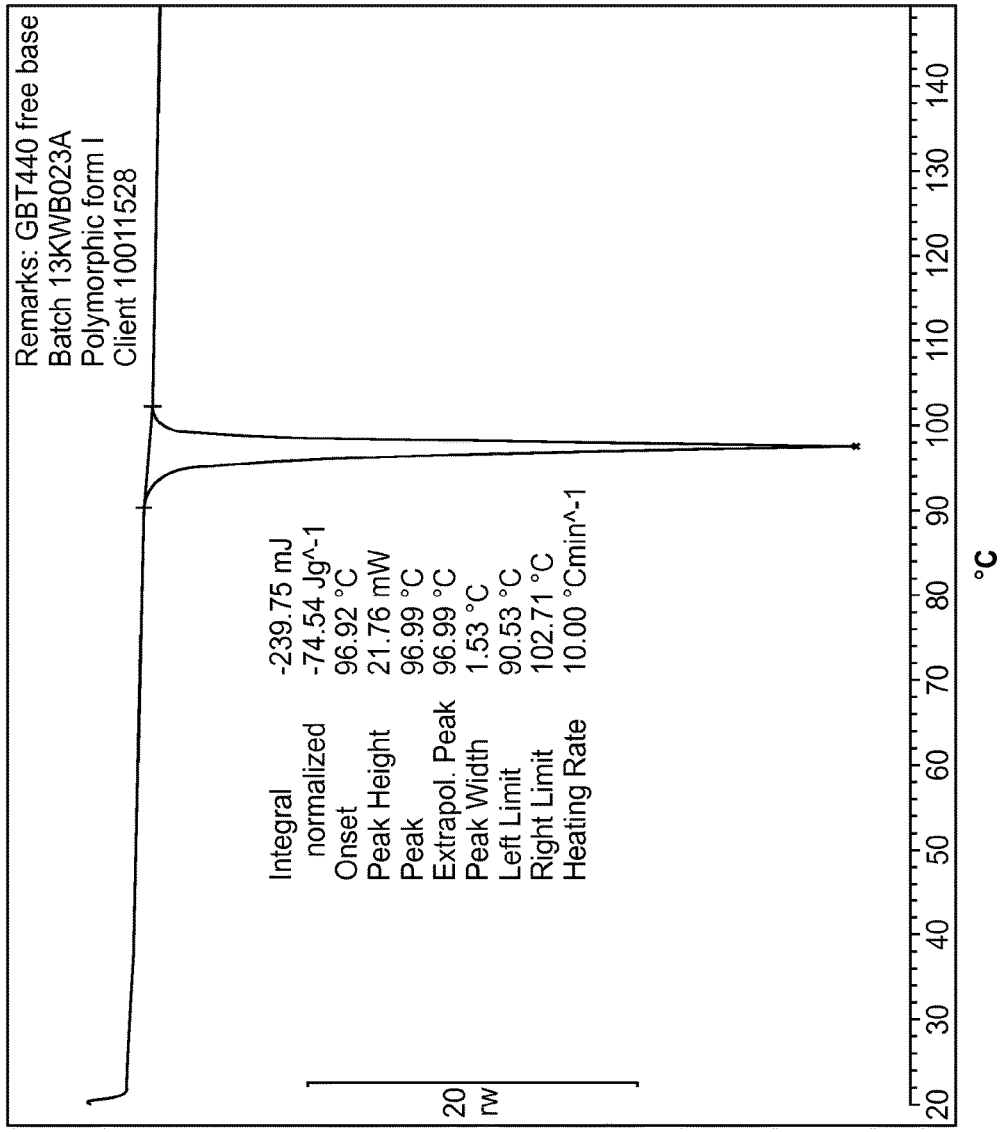
FIG. 14 depicts a DSC curve for Free Base Form I.
Figure 15:
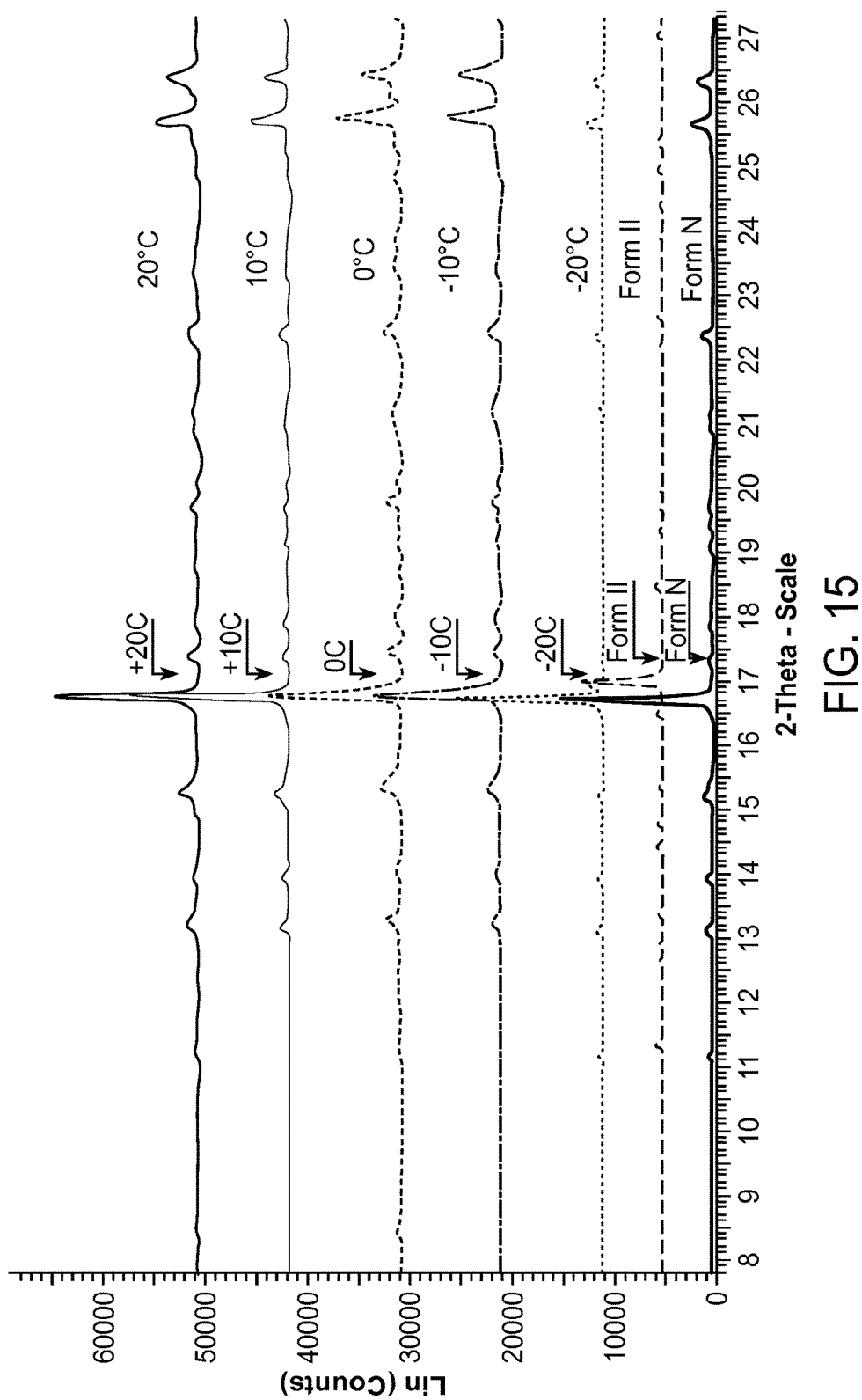
FIG. 15 depicts a XRPD profile of maturation experiments for the free base of Compound 1 at multiple temperatures.
Figure 16:
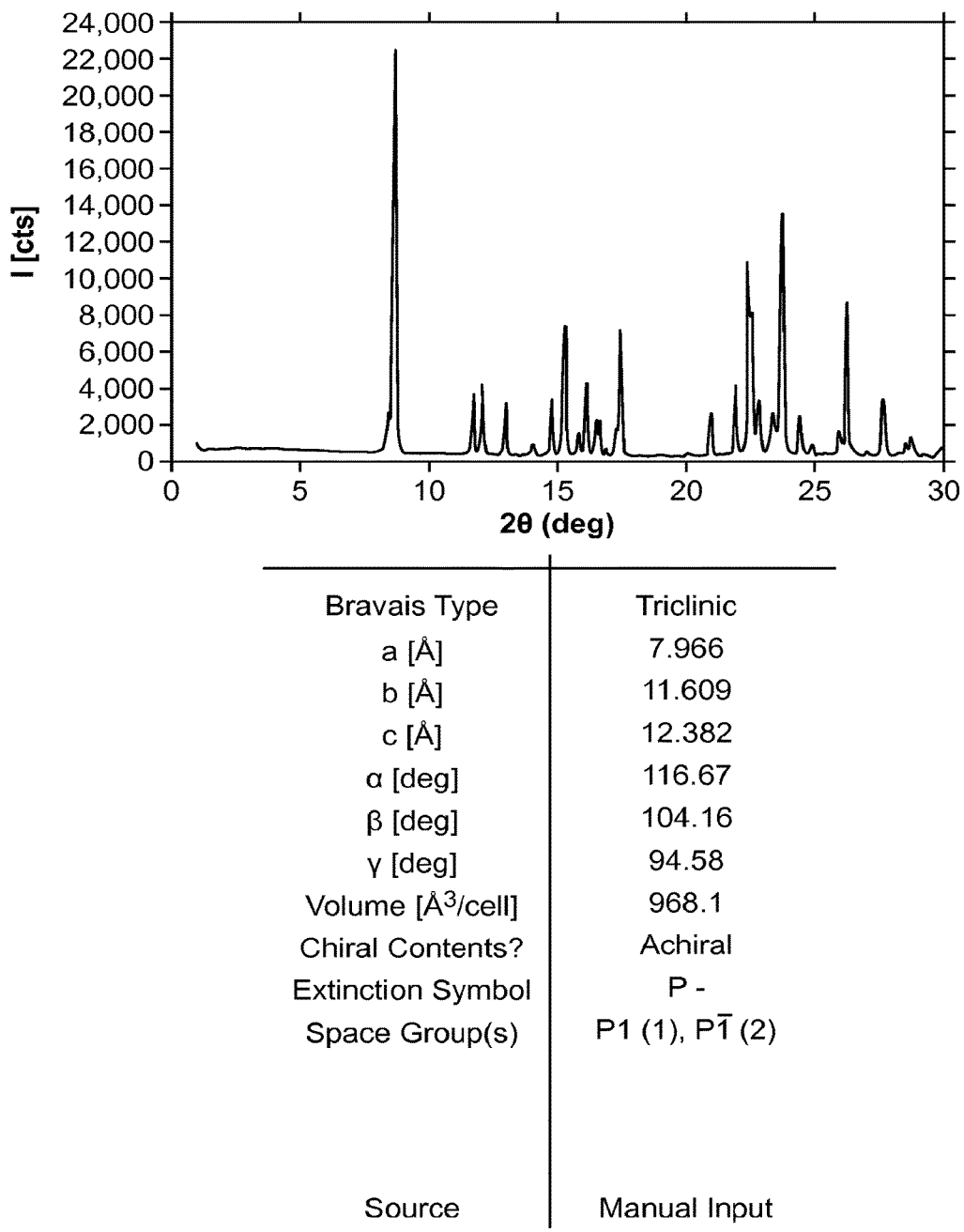
FIG. 16 depicts a contemplated XRPD profile for solvated Material E.

Based in part on solid-state nuclear magnetic resonance data, all three forms are crystalline and are distinct polymorphic forms. See FIGS. 10 and 11. Form I contains one molecule per asymmetric unit, Form II contains two molecules per asymmetric unit and Form N contains four molecules per asymmetric unit. See the $^{15}N$ spectra in FIG. 11.

Ansolvates of Forms I, II and Material N

In one embodiment, this invention provides the free base crystalline ansolvate of Compound 1. The free base crystalline ansolvate of Compound 1 may include one or more of Form I, Form II and/or Material N polymorphs. In some embodiments, the free base crystalline ansolvate of Compound 1 may include the Form II polymorph. Preferably, the free base crystalline ansolvate of Compound 1 may include Form II and/or Material N polymorphs. More preferably, the free base crystalline ansolvate of Compound 1 may include the Material N polymorph. Yet more preferably, the free base crystalline ansolvate of Compound 1 is substantially free of a solvated polymorph of Compound 1 free base. Further yet more preferably, the free base crystalline ansolvate of Compound 1 is substantially free of other ansolavte polymorphs of Compound 1 free base. "Substantially free" of a component as used herein refers to contain up to about 5%, more preferably about 3%, and still more preferably about 1% of that component. As used herein, solvate includes a hydrate form as well.

Solvates of Compound 1

In one aspect, provided is a crystalline solvate of Compound 1:

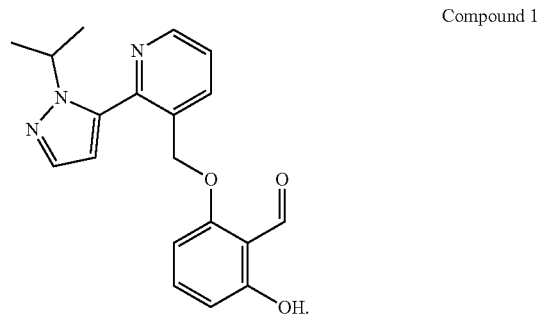 [SMILES: CC(C)n1nccc1-c1ncccc1COc1cccc(O)c1C=O]

Compound 1

In some embodiments, the crystalline solvate is substantially free of an ansolvated polymorph of Compound 1.

Many of the solubility and screen experiments with the free base of Compound 1 resulted in precipitation of solids characterized as solvate formation with some solvents. Under the conditions, solvates were not observed from the free base of Compound 1 with four solvents, including heptane, di-isopropyl ether (IPE), tert-methyl butyl ether (MTBE) and toluene. Solvates were observed from the free base of Compound 1 in nine solvents including acetone (Material E), acetonitrile (Material F), dichloromethane (Material G), dioxane (Material H), ethanol (Material J), isopropyl alcohol or a mixture of water and isopropyl alcohol (Material K), tetrahydrofuran (Material L), methyl ethyl ketone "MEK" (Material M), ethyl acetate (Material O) and dimethyl sulfoxide "DMSO" (Material P). The majority of the solvates (i.e., Materials E-H, J-M, O and P are contemplated to be isostructural. In some embodiments, the crystalline solvate includes one or more of Material E, Material F, Material G, Material H, Material J, Material K, Material L, Material M, Material O or Material P.

Material E can be characterized by at least one X-ray powder diffraction peak (Cu Kα radiation) selected from 8.69, 11.73, 12.10, 15.26, 16.11, 17.45, 22.39, 22.55 and 23.70±0.20. Material F can be characterized by at least one X-ray powder diffraction peak (Cu Kα radiation) selected from 8.47, 8.81, 12.75, 13.17, 14.92, 15.63, 17.01 23.73, and 24.07±0.20. Material G can be characterized by at least one X-ray powder diffraction peak (Cu Kα radiation) selected from 8.47, 11.45, 12.62, 14.66, 15.69, 17.01, 18.47, 20.32, 22.61, 23.08, 23.43 and 23.70±0.20. Material H can be characterized by at least one X-ray powder diffraction peak (Cu Kα radiation) selected from 8.61, 11.67, 15.33, 16.28, 17.28, 22.58, 23.51 and 25.77±0.20. Material J can be characterized by at least one X-ray powder diffraction peak (Cu Kα radiation) selected from 8.52, 8.88, 12.79, 15.04, 15.61, 17.11, 22.81, 23.87, 24.17, 24.62 and 26.44±0.20. Material K can be characterized by at least one X-ray powder diffraction peak (Cu Kα radiation) selected from 8.52; 8.83, 11.35, 15.04, 15.74, 17.11, 23.46, 23.58, 24.08 and 25.99±0.20. Material L can be characterized by at least one X-ray powder diffraction peak (Cu Kα radiation) selected from 8.61, 8.78, 11.67, 14.94, 15.28, 16.14, 17.30, 22.75, 23.71 and 26.05±0.20; and Material M can be characterized by at least one X-ray powder diffraction peak (Cu Kα radiation) selected from 7.74, 10.05, 12.82, 15.33, 16.80, 20.82, 21.14, 25.80 and 26.97±0.20.

The solvates (such as, of acetone, acetonitrile, dichloromethane, dioxane, ethanol, ethyl acetate, isopropyl alcohol, MEK, tetrahydrofuran or DMSO) could be used e.g., as intermediates to regenerate the free base crystalline ansolvate of Compound 1 by several methods including subjecting the solvate to vacuum conditions; and/or regenerating the HCl salt and disproportionating HCl; and/or washing the solvate with a solvent less prone to solvate formation such as heptane, di-isopropyl ether (IPE), tert-methyl butyl ether (MTBE) and toluene.

TABLE 1

Data Related to Solvates of the Free Base of Compound 1

Figure 2:
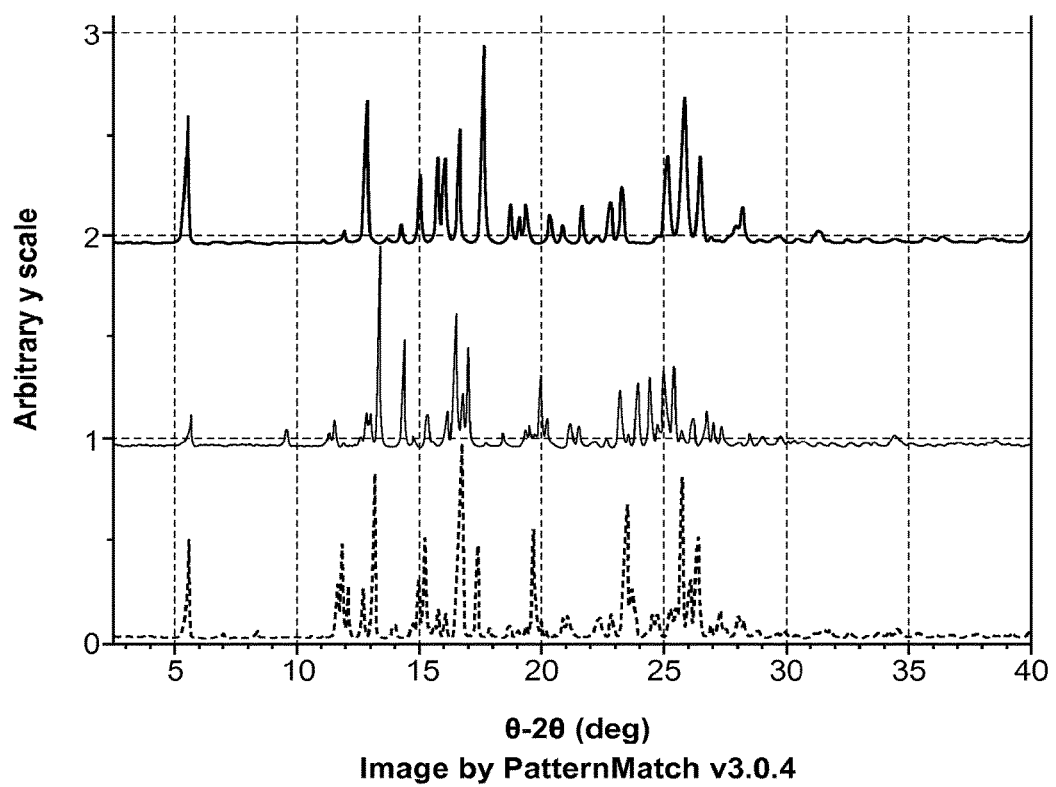
FIG. 2 is a XRPD profile of the free base Form I (top), Form II (middle), and Material N (bottom).
Figure 3:
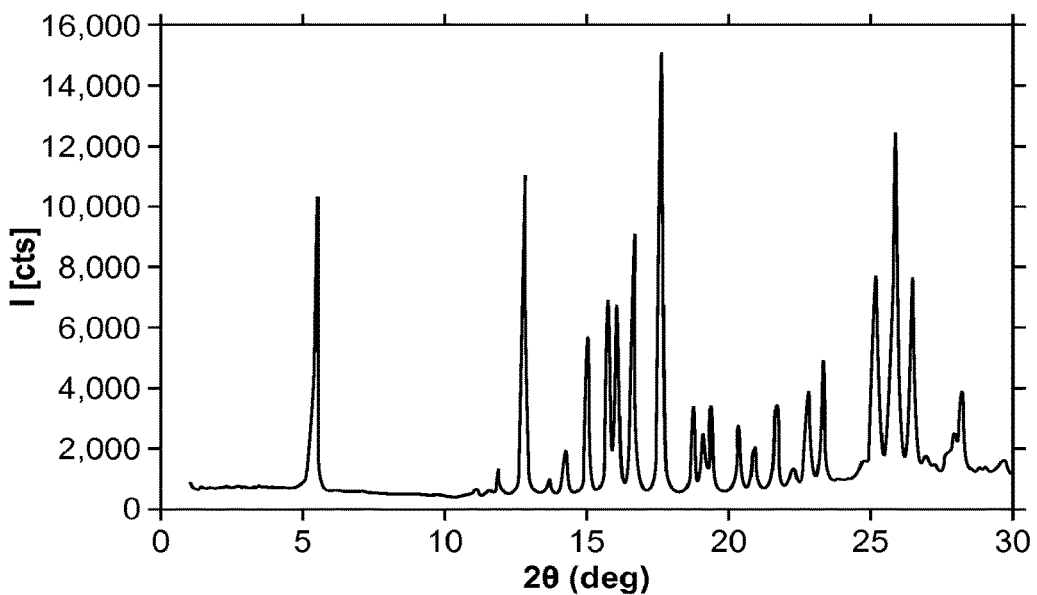
FIG. 3 is a XRPD profile and contemplated indexing for free base Form I.
Figure 4:
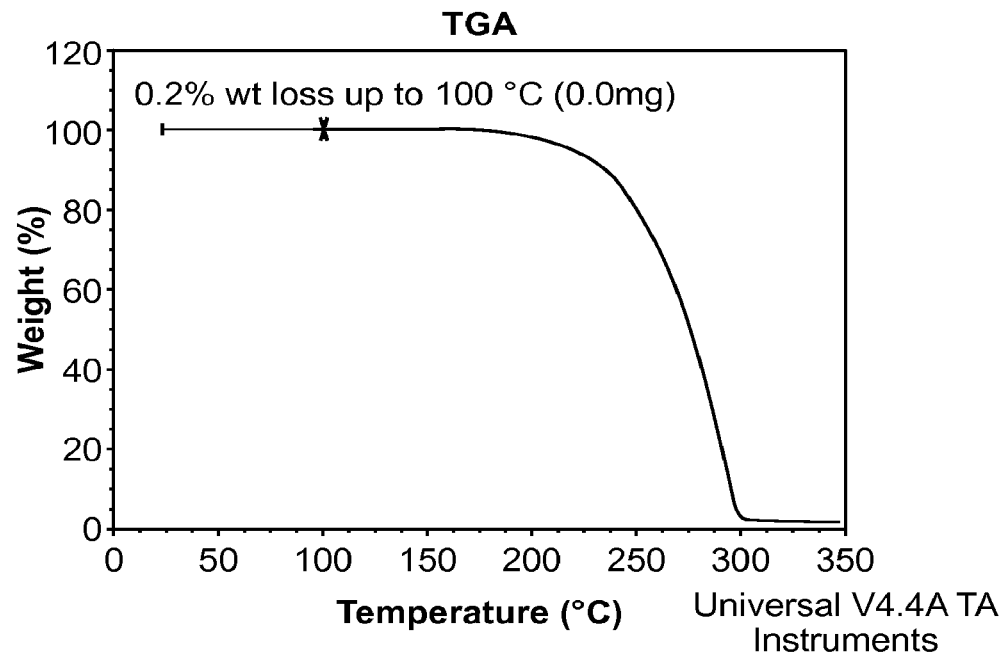
FIG. 4 is a thermal characterization for free base Form I.
Figure 4:
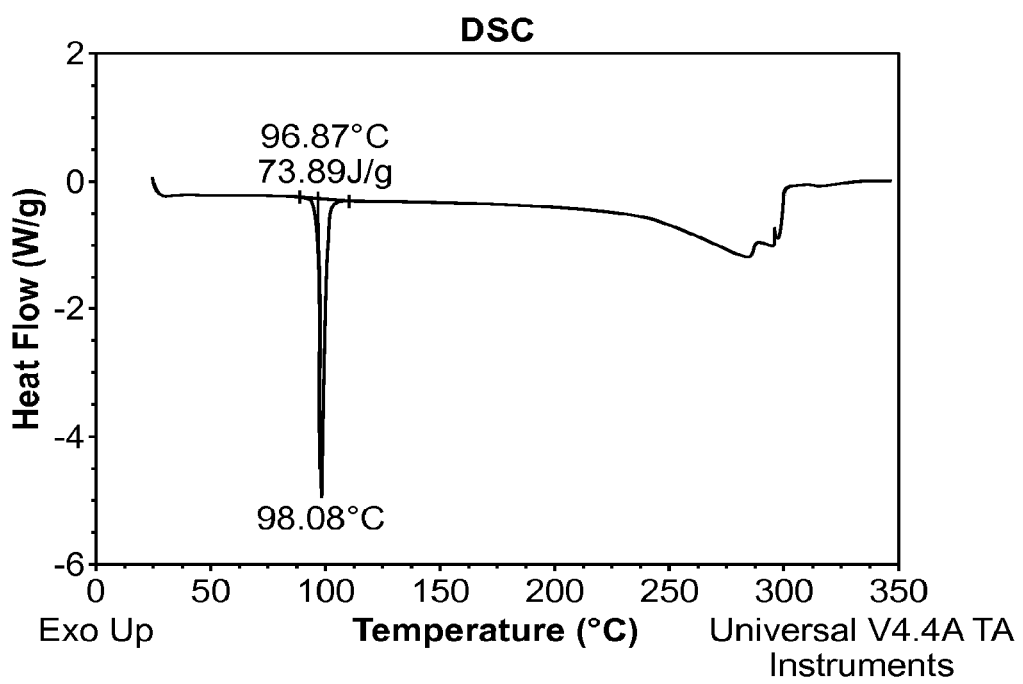
Figure 5:
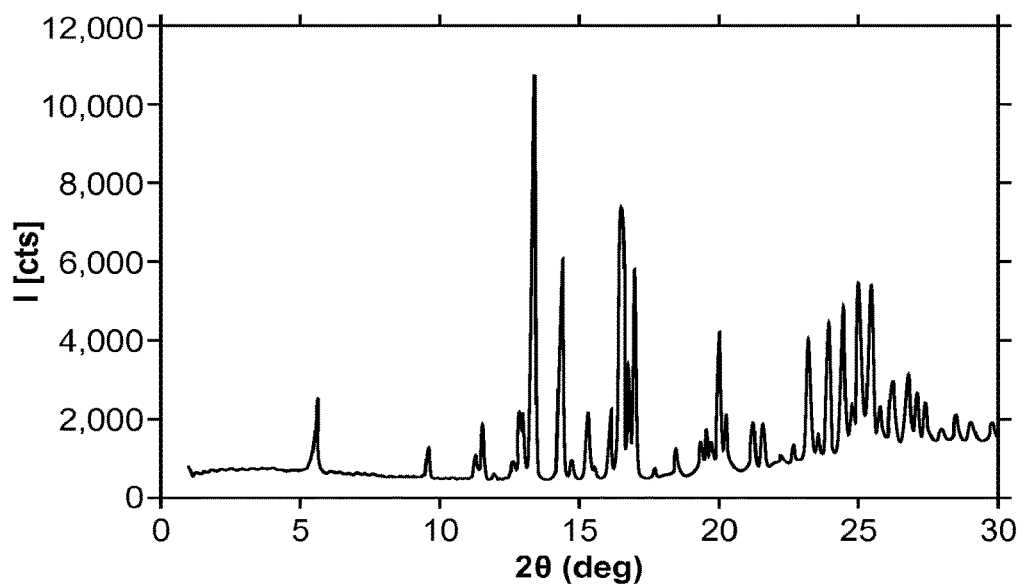
FIG. 5 is a XRPD profile and contemplated indexing for free base Form II.
Figure 6:
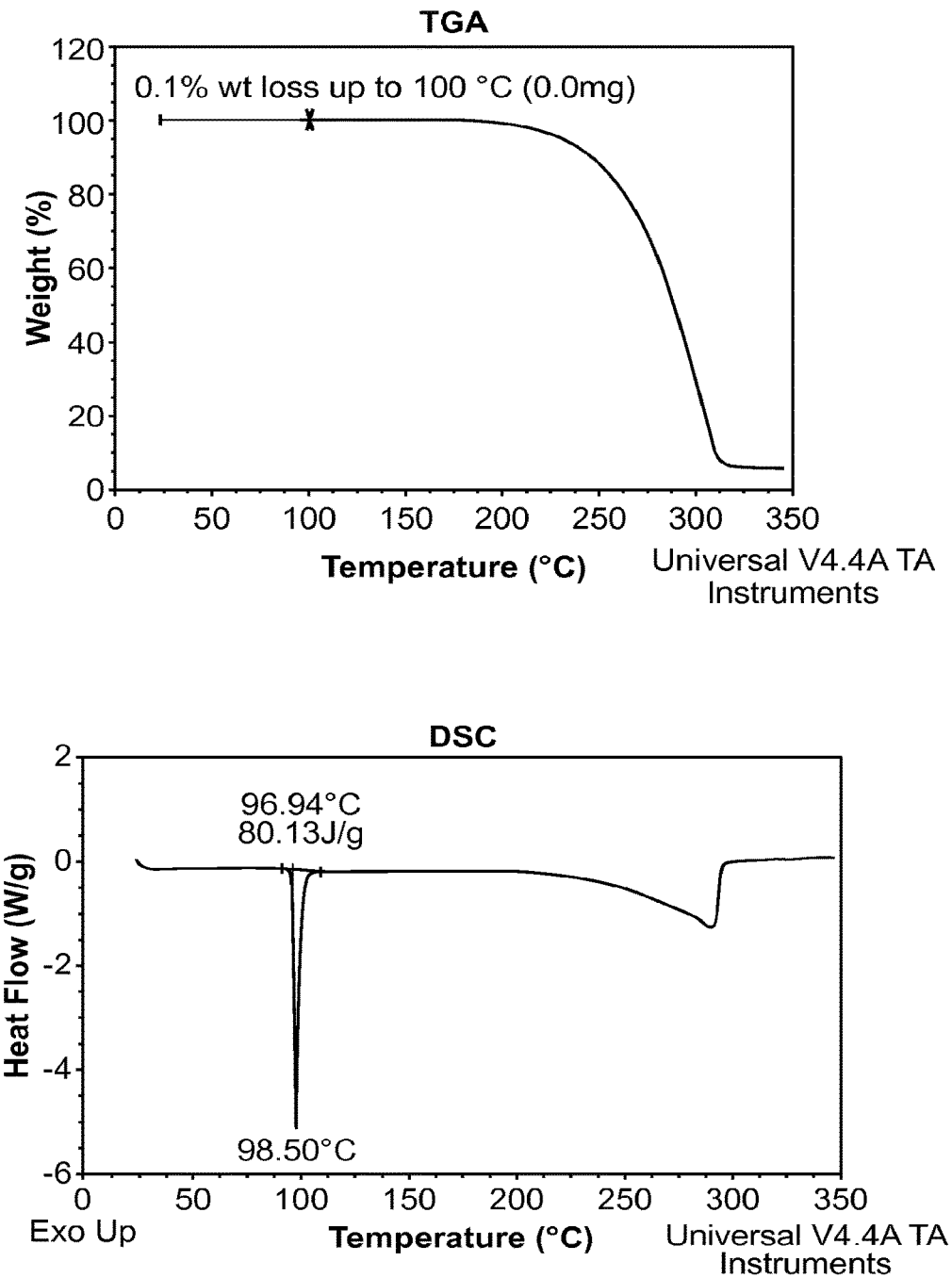
FIG. 6 is a thermal characterization for free base Form II.
Figure 7:
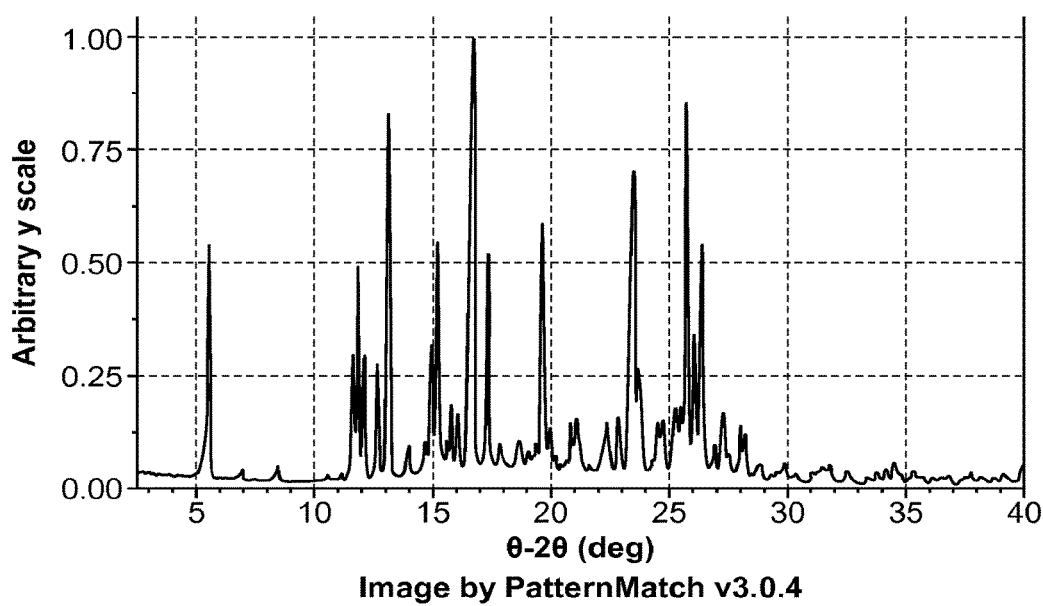
FIG. 7 is a XRPD profile for free base Material N.
Figure 8:
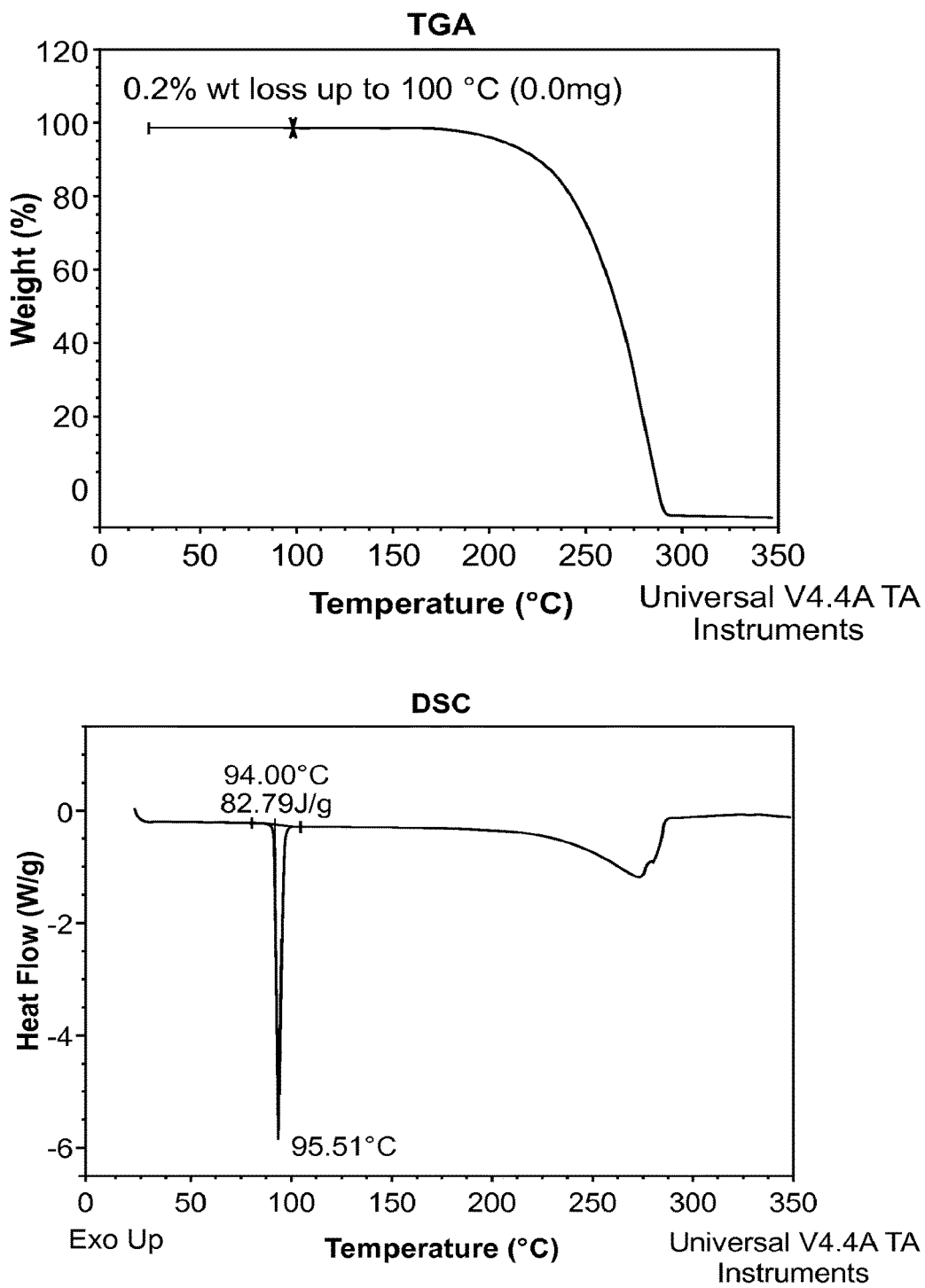
FIG. 8 is a thermal characterization for free base Material N.
Figure 9:
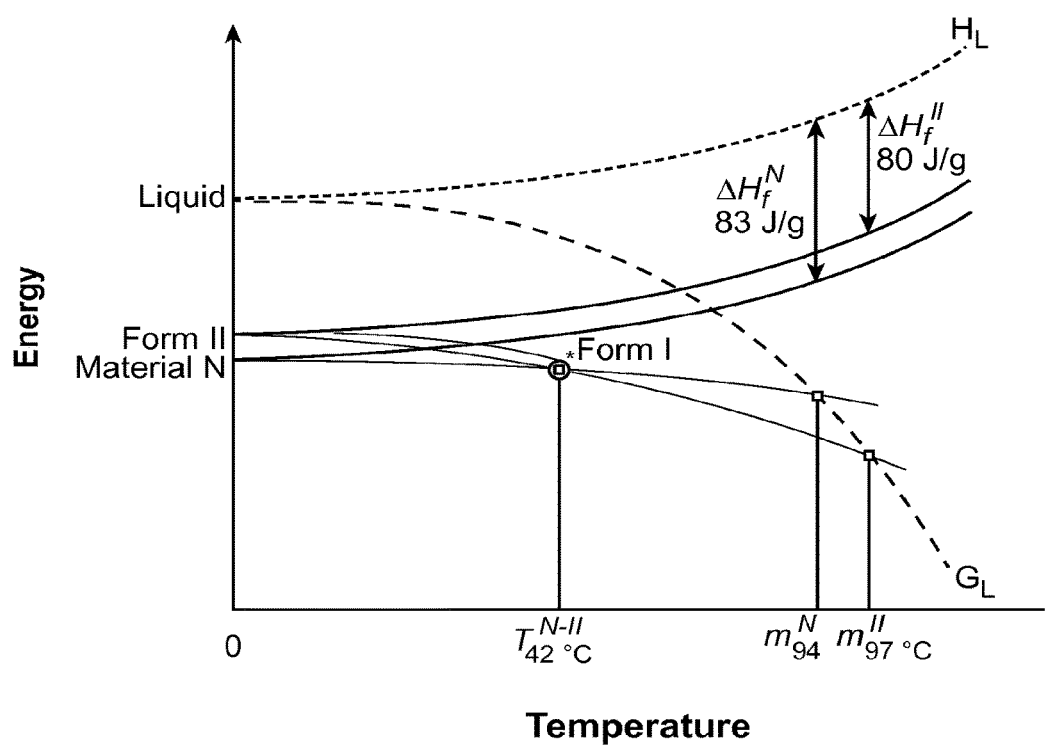
FIG. 9 depicts an Energy-Temperature Diagram between the Free Base Forms I, II, and Material N. The enthalpy (H) and free energy (G) isobars for each form are depicted as a function of temperature. $\Delta H_f$ is the heat of fusion; T is transition temperature; m is melt temperature; superscripts I, II, and N refer to the polymorphs. *Under the test conditions, not enough information was available to graphically represent the free energy isobar of Form I below 6° C. and above the estimated transition temperature $T^{N-II}$; the isobar likely intersects $G_L$ at a temperature below $m^{II}$, allowing the possibility that Form I may be enantiotropic with Form II (where $T^{I-II}$ occurs below 6° C.) and/or Material N (where either $T^{I-N}$ occurs below $T^{I-II}$ or $T^{N-I}$ occurs above $T^{N-II}$, but not both). Free energy isobars can only intersect each other once.

| Identifier | Crystallization Solvent | Volume (Å³/Cell) | Number of Formula Units per Cell | Estimated Volume per Formula Unit* (Å³) | Indexing Result |
|---|---|---|---|---|---|
| Material E | acetone | 968 | 2 | 484 | FIG. 1 |
| Material F | ACN | 947 | 2 | 473 | FIG. 2 |
| Material G | DCM | 959 | 2 | 480 | FIG. 3 |
| Material H | dioxane | 977 | 2 | 488 | FIG. 4 |
| Material J | EtOH | 943 | 2 | 472 | FIG. 5 |
| Material K | IPA | 963 | 2 | 481 | FIG. 6 |
| Material L | THF | 972 | 2 | 486 | FIG. 7 |
| Material M | MEK | 3956 | 8 | 494 | FIG. 8 |
| Material O | EtOAc | — | — | — | FIG. 9 |
| Material P** | DMSO | — | — | — | — |

*The value is obtained by dividing the volume of the cell, derived from the tentative indexing solution, by the number of formula units within the cell.
**Material P was observed as a mixture with a "sulfate form I".

Certain contemplated peaks of the various solvates provided herein are tabulated below. Certain peaks, which are preferably non-overlapping, low-angle peaks, with strong intensity, were not identified. The peaks were determined to the extent that the state of preferred orientation in the samples were unknown.

TABLE 2

Observed peaks for Material E.

| °2θ | d space (Å) | Intensity (%) |
|---|---|---|
| 8.41 ± 0.20 | 10.517 ± 0.256 | 13 |
| 8.69 ± 0.20 | 10.174 ± 0.239 | 100 |
| 11.73 ± 0.20 | 7.543 ± 0.130 | 17 |
| 12.10 ± 0.20 | 7.314 ± 0.122 | 20 |
| 13.00 ± 0.20 | 6.809 ± 0.106 | 15 |
| 14.02 ± 0.20 | 6.316 ± 0.091 | 5 |
| 14.77 ± 0.20 | 5.996 ± 0.082 | 16 |
| 15.26 ± 0.20 | 5.807 ± 0.077 | 34 |
| 15.81 ± 0.20 | 5.605 ± 0.071 | 7 |
| 16.11 ± 0.20 | 5.501 ± 0.069 | 20 |
| 16.48 ± 0.20 | 5.379 ± 0.066 | 11 |
| 16.65 ± 0.20 | 5.326 ± 0.064 | 11 |
| 16.88 ± 0.20 | 5.253 ± 0.063 | 3 |
| 17.26 ± 0.20 | 5.136 ± 0.060 | 9 |
| 17.45 ± 0.20 | 5.083 ± 0.058 | 32 |
| 20.02 ± 0.20 | 4.435 ± 0.044 | 2 |
| 20.92 ± 0.20 | 4.246 ± 0.041 | 13 |
| 21.91 ± 0.20 | 4.057 ± 0.037 | 20 |
| 22.39 ± 0.20 | 3.970 ± 0.035 | 49 |
| 22.55 ± 0.20 | 3.944 ± 0.035 | 37 |
| 22.81 ± 0.20 | 3.898 ± 0.034 | 16 |
| 23.36 ± 0.20 | 3.807 ± 0.032 | 12 |
| 23.70 ± 0.20 | 3.755 ± 0.032 | 61 |
| 24.37 ± 0.20 | 3.653 ± 0.030 | 12 |
| 24.85 ± 0.20 | 3.583 ± 0.029 | 5 |
| 25.42 ± 0.20 | 3.504 ± 0.027 | 2 |
| 25.89 ± 0.20 | 3.442 ± 0.026 | 8 |
| 26.19 ± 0.20 | 3.403 ± 0.026 | 40 |
| 26.97 ± 0.20 | 3.306 ± 0.024 | 3 |
| 27.61 ± 0.20 | 3.231 ± 0.023 | 16 |
| 28.24 ± 0.20 | 3.160 ± 0.022 | 2 |
| 28.48 ± 0.20 | 3.134 ± 0.022 | 5 |
| 28.69 ± 0.20 | 3.111 ± 0.021 | 7 |
| 29.83 ± 0.20 | 2.995 ± 0.020 | 4 |

TABLE 3

Observed peaks for Material F.

| °2θ | d space (Å) | Intensity (%) |
|---|---|---|
| 8.47 ± 0.20 | 10.434 ± 0.252 | 100 |
| 8.81 ± 0.20 | 10.039 ± 0.233 | 49 |
| 11.42 ± 0.20 | 7.752 ± 0.138 | 15 |
| 12.75 ± 0.20 | 6.942 ± 0.110 | 27 |
| 13.17 ± 0.20 | 6.723 ± 0.103 | 21 |
| 13.87 ± 0.20 | 6.384 ± 0.093 | 7 |
| 14.61 ± 0.20 | 6.064 ± 0.084 | 13 |
| 14.92 ± 0.20 | 5.936 ± 0.080 | 43 |
| 15.51 ± 0.20 | 5.713 ± 0.074 | 24 |
| 15.63 ± 0.20 | 5.671 ± 0.073 | 43 |
| 15.96 ± 0.20 | 5.553 ± 0.070 | 15 |
| 17.01 ± 0.20 | 5.212 ± 0.062 | 31 |
| 17.26 ± 0.20 | 5.136 ± 0.060 | 4 |
| 17.70 ± 0.20 | 5.011 ± 0.057 | 9 |
| 18.17 ± 0.20 | 4.883 ± 0.054 | 4 |
| 18.79 ± 0.20 | 4.724 ± 0.050 | 10 |
| 19.35 ± 0.20 | 4.587 ± 0.047 | 4 |
| 19.49 ± 0.20 | 4.555 ± 0.047 | 3 |
| 20.02 ± 0.20 | 4.435 ± 0.044 | 4 |
| 20.29 ± 0.20 | 4.377 ± 0.043 | 9 |

TABLE 3-continued

Observed peaks for Material F.

| °2θ | d space (Å) | Intensity (%) |
|---|---|---|
| 21.06 ± 0.20 | 4.219 ± 0.040 | 11 |
| 21.33 ± 0.20 | 4.167 ± 0.039 | 4 |
| 22.71 ± 0.20 | 3.915 ± 0.034 | 27 |
| 23.11 ± 0.20 | 3.848 ± 0.033 | 15 |
| 23.73 ± 0.20 | 3.749 ± 0.031 | 42 |
| 24.07 ± 0.20 | 3.698 ± 0.031 | 59 |
| 24.65 ± 0.20 | 3.612 ± 0.029 | 87 |
| 24.95 ± 0.20 | 3.569 ± 0.028 | 6 |
| 25.20 ± 0.20 | 3.534 ± 0.028 | 5 |
| 25.69 ± 0.20 | 3.468 ± 0.027 | 15 |
| 26.52 ± 0.20 | 3.361 ± 0.025 | 61 |
| 26.79 ± 0.20 | 3.328 ± 0.025 | 10 |
| 27.02 ± 0.20 | 3.300 ± 0.024 | 9 |

TABLE 4

Observed peaks for Material G.

| °2θ | d space (Å) | Intensity (%) |
|---|---|---|
| 8.47 ± 0.20 | 10.434 ± 0.252 | 45 |
| 8.76 ± 0.20 | 10.096 ± 0.235 | 12 |
| 11.45 ± 0.20 | 7.729 ± 0.137 | 76 |
| 12.62 ± 0.20 | 7.015 ± 0.113 | 36 |
| 13.09 ± 0.20 | 6.765 ± 0.105 | 10 |
| 13.87 ± 0.20 | 6.384 ± 0.093 | 5 |
| 14.66 ± 0.20 | 6.044 ± 0.083 | 39 |
| 14.92 ± 0.20 | 5.936 ± 0.080 | 26 |
| 15.33 ± 0.20 | 5.782 ± 0.076 | 7 |
| 15.69 ± 0.20 | 5.647 ± 0.072 | 88 |
| 16.01 ± 0.20 | 5.536 ± 0.070 | 8 |
| 16.76 ± 0.20 | 5.289 ± 0.063 | 15 |
| 17.01 ± 0.20 | 5.212 ± 0.062 | 29 |
| 17.50 ± 0.20 | 5.068 ± 0.058 | 5 |
| 17.60 ± 0.20 | 5.040 ± 0.057 | 4 |
| 18.13 ± 0.20 | 4.892 ± 0.054 | 5 |
| 18.47 ± 0.20 | 4.804 ± 0.052 | 21 |
| 19.55 ± 0.20 | 4.540 ± 0.046 | 4 |
| 20.01 ± 0.20 | 4.439 ± 0.044 | 5 |
| 20.32 ± 0.20 | 4.370 ± 0.043 | 20 |
| 21.11 ± 0.20 | 4.209 ± 0.040 | 15 |
| 22.61 ± 0.20 | 3.932 ± 0.035 | 42 |
| 22.88 ± 0.20 | 3.887 ± 0.034 | 9 |
| 23.08 ± 0.20 | 3.854 ± 0.033 | 28 |
| 23.43 ± 0.20 | 3.797 ± 0.032 | 56 |
| 23.70 ± 0.20 | 3.755 ± 0.032 | 48 |
| 24.12 ± 0.20 | 3.690 ± 0.030 | 13 |
| 24.42 ± 0.20 | 3.646 ± 0.030 | 100 |
| 25.05 ± 0.20 | 3.555 ± 0.028 | 7 |
| 25.40 ± 0.20 | 3.506 ± 0.027 | 26 |
| 26.36 ± 0.20 | 3.382 ± 0.025 | 50 |
| 26.57 ± 0.20 | 3.355 ± 0.025 | 7 |
| 26.82 ± 0.20 | 3.324 ± 0.025 | 27 |
| 27.07 ± 0.20 | 3.294 ± 0.024 | 10 |

TABLE 5

Observed peaks for Material H.

| °2θ | d space (Å) | Intensity (%) |
|---|---|---|
| 8.61 ± 0.20 | 10.273 ± 0.244 | 48 |
| 8.81 ± 0.20 | 10.039 ± 0.233 | 20 |
| 11.67 ± 0.20 | 7.586 ± 0.132 | 32 |
| 12.10 ± 0.20 | 7.314 ± 0.122 | 11 |
| 12.79 ± 0.20 | 6.924 ± 0.110 | 9 |
| 14.56 ± 0.20 | 6.085 ± 0.084 | 4 |
| 14.87 ± 0.20 | 5.956 ± 0.081 | 22 |
| 15.33 ± 0.20 | 5.782 ± 0.076 | 42 |
| 15.76 ± 0.20 | 5.623 ± 0.072 | 18 |
| 16.28 ± 0.20 | 5.445 ± 0.067 | 51 |

TABLE 5-continued

Observed peaks for Material H.

| °2θ | d space (Å) | Intensity (%) |
|---|---|---|
| 16.73 ± 0.20 | 5.299 ± 0.064 | 9 |
| 17.28 ± 0.20 | 5.132 ± 0.060 | 61 |
| 17.68 ± 0.20 | 5.016 ± 0.057 | 3 |
| 20.47 ± 0.20 | 4.338 ± 0.042 | 12 |
| 21.38 ± 0.20 | 4.157 ± 0.039 | 7 |
| 21.83 ± 0.20 | 4.072 ± 0.037 | 4 |
| 22.23 ± 0.20 | 3.999 ± 0.036 | 9 |
| 22.58 ± 0.20 | 3.938 ± 0.035 | 100 |
| 22.95 ± 0.20 | 3.876 ± 0.034 | 6 |
| 23.11 ± 0.20 | 3.848 ± 0.033 | 14 |
| 23.51 ±0.20 | 3.783 ± 0.032 | 88 |
| 24.37 ± 0.20 | 3.653 ± 0.030 | 13 |
| 24.65 ± 0.20 | 3.612 ± 0.029 | 10 |
| 25.77 ± 0.20 | 3.457 ± 0.027 | 41 |
| 26.67 ± 0.20 | 3.342 ± 0.025 | 7 |
| 26.97 ± 0.20 | 3.306 ± 0.024 | 5 |
| 27.66 ± 0.20 | 3.225 ± 0.023 | 3 |
| 28.11 ± 0.20 | 3.174 ± 0.022 | 4 |
| 28.61 ± 0.20 | 3.120 ± 0.022 | 6 |
| 28.96 ± 0.20 | 3.083 ± 0.021 | 4 |
| 29.23 ± 0.20 | 3.055 ± 0.021 | 3 |
| 29.63 ± 0.20 | 3.015 ± 0.020 | 3 |

TABLE 6

Observed peaks for Material J.

| °2θ | d space (Å) | Intensity (%) |
|---|---|---|
| 8.52 ± 0.20 | 10.373 ± 0.249 | 100 |
| 8.88 ± 0.20 | 9.964 ± 0.229 | 39 |
| 11.33 ± 0.20 | 7.809 ± 0.140 | 22 |
| 12.79 ± 0.20 | 6.924 ± 0.110 | 25 |
| 13.12 ± 0.20 | 6.748 ± 0.104 | 24 |
| 13.94 ± 0.20 | 6.354 ± 0.092 | 4 |
| 14.47 ± 0.20 | 6.120 ± 0.085 | 14 |
| 15.04 ± 0.20 | 5.890 ± 0.079 | 42 |
| 15.61 ± 0.20 | 5.677 ± 0.073 | 56 |
| 15.84 ± 0.20 | 5.594 ± 0.071 | 16 |
| 17.11 ± 0.20 | 5.181 ± 0.061 | 33 |
| 17.40 ± 0.20 | 5.097 ± 0.059 | 4 |
| 17.82 ± 0.20 | 4.979 ± 0.056 | 8 |
| 18.12 ± 0.20 | 4.897 ± 0.054 | 3 |
| 18.90 ± 0.20 | 4.695 ± 0.050 | 11 |
| 19.39 ± 0.20 | 4.579 ± 0.047 | 5 |
| 19.62 ± 0.20 | 4.525 ± 0.046 | 4 |
| 20.16 ± 0.20 | 4.406 ± 0.044 | 8 |
| 20.96 ± 0.20 | 4.239 ± 0.040 | 12 |
| 22.81 ± 0.20 | 3.898 ± 0.034 | 27 |
| 23.15 ± 0.20 | 3.843 ± 0.033 | 9 |
| 23.28 ± 0.20 | 3.821 ± 0.033 | 7 |
| 23.87 ± 0.20 | 3.729 ± 0.031 | 34 |
| 24.17 ± 0.20 | 3.683 ± 0.030 | 52 |
| 24.62 ± 0.20 | 3.616 ± 0.029 | 95 |
| 25.20 ± 0.20 | 3.534 ± 0.028 | 5 |
| 25.77 ± 0.20 | 3.457 ± 0.027 | 13 |
| 26.44 ± 0.20 | 3.371 ± 0.025 | 70 |
| 26.71 ± 0.20 | 3.338 ± 0.025 | 10 |
| 27.21 ± 0.20 | 3.278 ± 0.024 | 7 |

TABLE 7

Observed peaks for GBT000440, Material K.

| °2θ | d space (Å) | Intensity (%) |
|---|---|---|
| 8.52 ± 0.20 | 10.373 ± 0.249 | 75 |
| 8.83 ± 0.20 | 10.020 ± 0.232 | 33 |
| 11.35 ± 0.20 | 7.797 ± 0.139 | 29 |
| 12.52 ± 0.20 | 7.071 ± 0.114 | 21 |
| 12.90 ± 0.20 | 6.861 ± 0.108 | 24 |

TABLE 7-continued

Observed peaks for GBT000440, Material K.

| °2θ | d space (Å) | Intensity (%) |
|---|---|---|
| 13.92 ± 0.20 | 6.361 ± 0.092 | 4 |
| 14.49 ± 0.20 | 6.113 ± 0.085 | 18 |
| 15.04 ± 0.20 | 5.890 ± 0.079 | 41 |
| 15.34 ± 0.20 | 5.775 ± 0.076 | 17 |
| 15.74 ± 0.20 | 5.629 ± 0.072 | 57 |
| 15.93 ± 0.20 | 5.564 ± 0.070 | 13 |
| 16.61 ± 0.20 | 5.336 ± 0.065 | 7 |
| 17.11 ± 0.20 | 5.181 ± 0.061 | 33 |
| 17.70 ± 0.20 | 5.011 ± 0.057 | 7 |
| 18.00 ± 0.20 | 4.928 ± 0.055 | 4 |
| 18.38 ± 0.20 | 4.826 ± 0.053 | 13 |
| 19.04 ± 0.20 | 4.662 ± 0.049 | 4 |
| 19.74 ± 0.20 | 4.498 ± 0.046 | 5 |
| 20.21 ± 0.20 | 4.395 ± 0.043 | 11 |
| 20.99 ± 0.20 | 4.232 ± 0.040 | 12 |
| 22.70 ± 0.20 | 3.918 ± 0.034 | 22 |
| 22.90 ± 0.20 | 3.884 ± 0.034 | 17 |
| 23.46 ± 0.20 | 3.791 ± 0.032 | 45 |
| 23.58 ± 0.20 | 3.773 ± 0.032 | 70 |
| 24.08 ± 0.20 | 3.695 ± 0.030 | 100 |
| 24.75 ± 0.20 | 3.597 ± 0.029 | 6 |
| 25.19 ± 0.20 | 3.536 ± 0.028 | 21 |
| 25.99 ± 0.20 | 3.429 ± 0.026 | 71 |
| 26.71 ± 0.20 | 3.338 ± 0.025 | 11 |
| 27.36 ± 0.20 | 3.260 ± 0.024 | 9 |
| 28.11 ± 0.20 | 3.174 ± 0.022 | 4 |
| 28.69 ± 0.20 | 3.111 ± 0.021 | 9 |

TABLE 8

Observed peaks for Material L.

| °2θ | d space (Å) | Intensity (%) |
|---|---|---|
| 8.61 ± 0.20 | 10.273 ± 0.244 | 79 |
| 8.78 ± 0.20 | 10.077 ± 0.235 | 38 |
| 11.67 ± 0.20 | 7.586 ± 0.132 | 35 |
| 12.17 ± 0.20 | 7.274 ± 0.121 | 19 |
| 12.94 ± 0.20 | 6.844 ± 0.107 | 14 |
| 14.07 ± 0.20 | 6.293 ± 0.090 | 3 |
| 14.62 ± 0.20 | 6.057 ± 0.084 | 5 |
| 14.94 ± 0.20 | 5.929 ± 0.080 | 25 |
| 15.28 ± 0.20 | 5.800 ± 0.076 | 50 |
| 15.93 ± 0.20 | 5.564 ± 0.070 | 18 |
| 16.14 ± 0.20 | 5.490 ± 0.068 | 49 |
| 16.33 ± 0.20 | 5.429 ± 0.067 | 9 |
| 16.70 ± 0.20 | 5.310 ± 0.064 | 9 |
| 16.85 ± 0.20 | 5.263 ± 0.063 | 6 |
| 17.30 ± 0.20 | 5.127 ± 0.060 | 52 |
| 17.63 ± 0.20 | 5.030 ± 0.057 | 6 |
| 18.37 ± 0.20 | 4.830 ± 0.053 | 3 |
| 20.14 ± 0.20 | 4.409 ± 0.044 | 5 |
| 20.59 ± 0.20 | 4.314 ± 0.042 | 14 |
| 21.53 ± 0.20 | 4.128 ± 0.038 | 11 |
| 22.01 ± 0.20 | 4.038 ± 0.037 | 3 |
| 22.44 ± 0.20 | 3.961 ± 0.035 | 27 |
| 22.75 ± 0.20 | 3.910 ± 0.034 | 72 |
| 23.10 ± 0.20 | 3.851 ± 0.033 | 20 |
| 23.31 ± 0.20 | 3.816 ± 0.033 | 19 |
| 23.48 ± 0.20 | 3.789 ± 0.032 | 12 |
| 23.71 ± 0.20 | 3.752 ± 0.031 | 100 |
| 24.48 ± 0.20 | 3.636 ± 0.029 | 20 |
| 24.70 ± 0.20 | 3.604 ± 0.029 | 4 |
| 24.93 ± 0.20 | 3.571 ± 0.028 | 3 |
| 25.59 ± 0.20 | 3.482 ± 0.027 | 5 |
| 25.72 ± 0.20 | 3.464 ± 0.027 | 5 |
| 26.05 ± 0.20 | 3.420 ± 0.026 | 62 |
| 26.59 ± 0.20 | 3.352 ± 0.025 | 6 |
| 27.14 ± 0.20 | 3.286 ± 0.024 | 8 |
| 27.83 ± 0.20 | 3.206 ± 0.023 | 8 |
| 28.38 ± 0.20 | 3.145 ± 0.022 | 3 |
| 28.78 ± 0.20 | 3.102 ± 0.021 | 8 |

TABLE 8-continued

Observed peaks for Material L.

| °2θ | d space (Å) | Intensity (%) |
|---|---|---|
| 29.05 ± 0.20 | 3.074 ± 0.021 | 4 |
| 29.36 ± 0.20 | 3.042 ± 0.020 | 3 |

TABLE 9

Observed peaks for Material M.

| °2θ | d space (Å) | Intensity (%) |
|---|---|---|
| 7.74 ± 0.20 | 11.424 ± 0.303 | 100 |
| 8.34 ± 0.20 | 10.601 ± 0.260 | 4 |
| 10.05 ± 0.20 | 8.806 ± 0.178 | 17 |
| 12.82 ± 0.20 | 6.906 ± 0.109 | 46 |
| 13.05 ± 0.20 | 6.783 ± 0.105 | 4 |
| 14.17 ± 0.20 | 6.249 ± 0.089 | 2 |
| 14.54 ± 0.20 | 6.092 ± 0.085 | 6 |
| 14.99 ± 0.20 | 5.910 ± 0.079 | 16 |
| 15.33 ± 0.20 | 5.782 ± 0.076 | 47 |
| 15.53 ± 0.20 | 5.707 ± 0.074 | 21 |
| 16.80 ± 0.20 | 5.278 ± 0.063 | 27 |
| 18.33 ± 0.20 | 4.839 ± 0.053 | 3 |
| 19.17 ± 0.20 | 4.630 ± 0.048 | 22 |
| 20.19 ± 0.20 | 4.399 ± 0.044 | 23 |
| 20.82 ± 0.20 | 4.266 ± 0.041 | 32 |
| 21.14 ± 0.20 | 4.202 ± 0.040 | 27 |
| 21.29 ± 0.20 | 4.173 ± 0.039 | 14 |
| 22.01 ± 0.20 | 4.038 ± 0.037 | 13 |
| 22.28 ± 0.20 | 3.991 ± 0.036 | 23 |
| 22.93 ± 0.20 | 3.879 ± 0.034 | 6 |
| 23.35 ± 0.20 | 3.810 ± 0.032 | 11 |
| 24.00 ± 0.20 | 3.708 ± 0.031 | 14 |
| 24.25 ± 0.20 | 3.670 ± 0.030 | 3 |
| 24.88 ± 0.20 | 3.578 ± 0.029 | 11 |
| 25.54 ± 0.20 | 3.488 ± 0.027 | 9 |
| 25.80 ± 0.20 | 3.453 ± 0.027 | 94 |
| 26.97 ± 0.20 | 3.306 ± 0.024 | 27 |
| 27.63 ± 0.20 | 3.229 ± 0.023 | 2 |
| 28.41 ± 0.20 | 3.142 ± 0.022 | 7 |
| 28.54 ± 0.20 | 3.127 ± 0.022 | 8 |
| 29.03 ± 0.20 | 3.076 ± 0.021 | 3 |
| 29.30 ± 0.20 | 3.049 ± 0.020 | 7 |
| 29.63 ± 0.20 | 3.015 ± 0.020 | 15 |

Pharmaceutical Compositions

In another of its composition embodiments, this invention provides for a pharmaceutical composition comprising a pharmaceutically acceptable excipient and crystalline free base ansolvate of Compound 1, preferably including one or more of the Form I, Form II and/or Material N polymorphs.

Such compositions can be formulated for different routes of administration. Although compositions suitable for oral delivery will probably be used most frequently, other routes that may be used include intravenous, intraarterial, pulmonary, rectal, nasal, vaginal, lingual, intramuscular, intraperitoneal, intracutaneous, intracranial, subcutaneous and transdermal routes. Suitable dosage forms for administering any of the compounds described herein include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, 16th ed., A. Oslo editor, Easton Pa. 1980).

Pharmaceutically acceptable excipients are non-toxic, aid administration, and do not adversely affect the therapeutic benefit of the compound of this invention. Such excipients may be any solid, liquid, semi-solid or, in the case of an aerosol composition, gaseous excipient that is generally available to one of skill in the art. Pharmaceutical compositions in accordance with the invention are prepared by conventional means using methods known in the art.

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. In certain embodiments, the compositions provided herein comprises one or more of α-tocopherol, gum arabic, and/or hydroxypropyl cellulose.

In one embodiment, this invention provides sustained release formulations such as drug depots or patches comprising an effective amount of a compound provided herein. In another embodiment, the patch further comprises gum Arabic or hydroxypropyl cellulose separately or in combination, in the presence of alpha-tocopherol. Preferably, the hydroxypropyl cellulose has an average MW of from 10,000 to 100,000. In a more preferred embodiment, the hydroxypropyl cellulose has an average MW of from 5,000 to 50,000.

Compounds and pharmaceutical compositions of this invention maybe used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

Preparative and Treatment Methods
Ansolvate

In another aspect, the present invention provides a method of preparing the crystalline free base ansolvate of Compound 1. In one embodiment, provided herein is a method of preparing the crystalline free base of Compound 1 comprising slurrying or contacting the HCl salt of the Compound 1 with water and allowing dissociation of HCl to produce the free base of Compound 1. In one embodiment, the crystalline free base ansolavte of Compound 1 prepared comprises one or more of Form I, Form II and Material N.

In yet another of its method embodiments, there are provided methods for increasing oxygen affinity of hemoglobin S in a subject, the method comprising administering to a subject in need thereof a therapeutically effective amount of a crystalline free base of Compound 1. In some embodiments, the crystalline free base of Compound 1 is an ansolvate. In one embodiment, the crystalline free base of Compound 1 comprises one or more of Form I, Form II and Material N.

In yet another of its method embodiments, there are provided methods for treating oxygen deficiency associated with sickle cell anemia in a subject, the method comprising administering to a subject in need thereof a therapeutically effective amount of a crystalline free base of Compound 1. In some embodiments, the crystalline free base of Compound 1 is an ansolvate. In one embodiment, the crystalline free base of Compound 1 comprises one or more of Form I, Form II and Material N.

In further aspects of the invention, a method is provided for treating sickle cell disease, the method comprising administering to a subject in need thereof a therapeutically effective amount of a crystalline free base of Compound 1. In some embodiments, the crystalline free base of Compound 1 is an ansolvate. In one embodiment, the crystalline free base of Compound 1 comprises one or more of Form I, Form II and Material N. In still further aspects of the invention, a method is provided for treating cancer, a pulmonary disorder, stroke, high altitude sickness, an ulcer, a pressure sore, Alzheimer's disease, acute respiratory disease syndrome, and a wound, the method comprising administering to a subject in need thereof a therapeutically effective amount of a crystalline free base of Compound 1. In some embodiments, the crystalline free base of Compound 1 is an ansolvate. In one embodiment, the crystalline free base of Compound 1 comprises one or more of Form I, Form II and Material N.

In such treatments, the dosing of the crystalline free base of Compound 1 to the treated patient is already disclosed in the art.

Solvates

In another aspect, the present invention provides a method of preparing the crystalline free base solvates of Compound 1. In some embodiments, a free base ansolvate, as described herein (e.g, as obtained by slurrying an HCl salt of Compound 1 in water) of Compound 1 is contacted with a solvent as provided herein, including a mixture of solvents, to prepare the solvate. the solvent or the mixture of solvents. Thus, a solvent can be a single solvent or substantially a single solvent or a mixture of solvents. When a mixture of solvents is used, a solvate can be produced having one or more of the individual constituent solvents of the solvent mixture. In some embodiments, the solvent includes alcoholic solvents such as mono di or higher alcohols or alkanols. In some embodiments, the solvent includes chlorinated solvents such as dichloromethane chloroform, et cetera. In some embodiments, the solvent includes ketone solvents such as alkanones and cycloalkanones. Certain solvents include without limitation, methanol, ethanol, 2-propanol, 2-methyl-1-propanol, 1-butanol, acetonitrile, acetone, dichloromethane, dioxane, or tetrahydrofuran, or combinations thereof, optionally including water.

In another aspect, a method is provided for increasing oxygen affinity of hemoglobin S in a subject, the method comprising administering to a subject in need thereof a therapeutically effective amount of a crystalline solvate of Compound 1.

In another aspect, a method is provided for treating oxygen deficiency associated with sickle cell anemia, the method comprising administering to a subject in need thereof a therapeutically effective amount of a crystalline solvate of Compound 1.

EXAMPLES

The following examples describe the preparation, characterization, and properties of the free base of Compound 1 Form I ansolvate. Unless otherwise stated, all temperatures are in degrees Celcius (° C.) and the following abbreviations have the following definitions:
DSC Differential scanning calorimetry
DVS Dynamic vapor sorption
HPLC High performance liquid chromatography
NA Not applicable
ND Not determined
Q Percent dissolved per unit time
RH Relative humidity
RSD Residual standard deviation
RRT Relative retention time
SS-NMR Solid state nuclear magnetic resonance
TGA Thermogravimetric analysis
TG-IR Thermogravimetric infra red analysis
XRPD X-ray powder diffraction
VT-XRPD Variable temperature X-ray powder diffraction
Synthetic Routes for Preparing Compound 1

The compound of formula (I) was synthesized as schematically described below and elaborated thereafter.

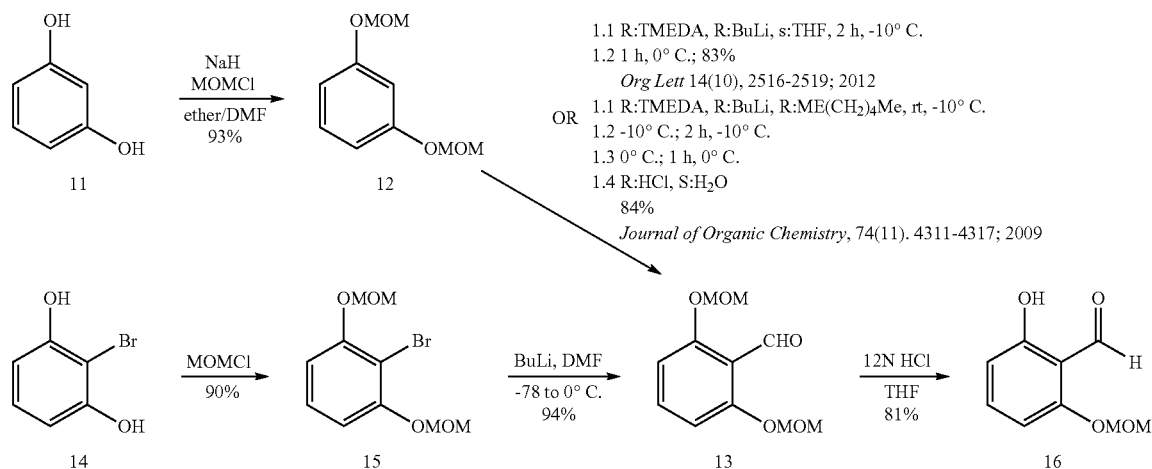

1.1 R:TMEDA, R:BuLi, s:THF, 2 h, -10° C.
1.2 1 h, 0° C.; 83%
  *Org Lett* 14(10), 2516-2519; 2012
OR
1.1 R:TMEDA, R:BuLi, R:ME(CH$_2$)$_4$Me, rt, -10° C.
1.2 -10° C.; 2 h, -10° C.
1.3 0° C.; 1 h, 0° C.
1.4 R:HCl, S:H$_2$O
84%
  *Journal of Organic Chemistry*, 74(11). 4311-4317; 2009

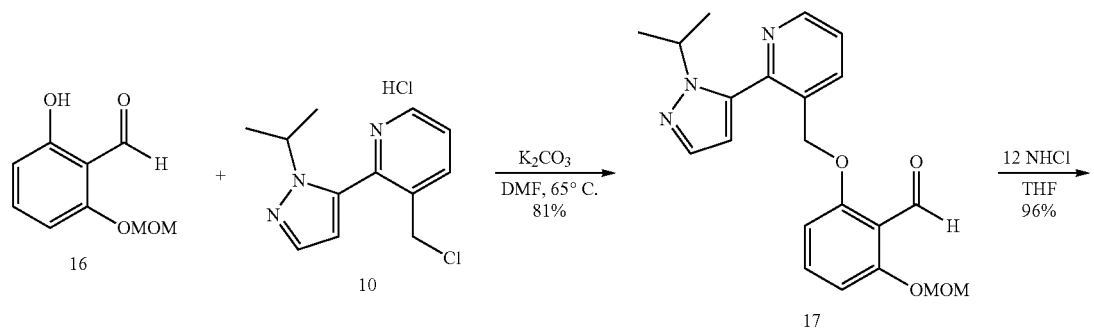

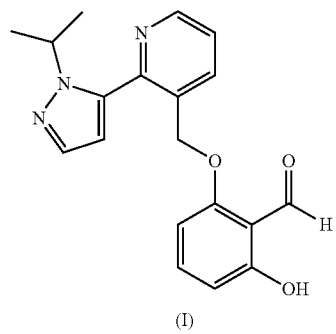

(I)

Example 1: Synthesis of Compound 15

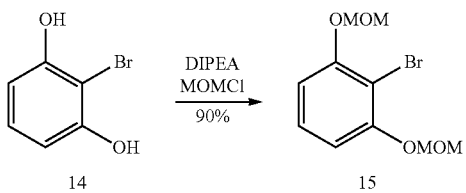

To a solution of 2-bromobenzene-1,3-diol (5 g, 26.45 mmol) in DCM (50 ml) at 0° C. was added DIPEA (11.54 mL, 66.13 mmol) and MOMCl (4.42 mL, 58.19 mmol). The mixture was stirred at 0° C. for 1.5 h, and then warmed to room temperature. The solution was diluted with DCM, washed with sat. NaHCO$_3$, brine, dried and concentrated to give crude product, which was purified by column (hexanes/EtOAc=4:1) to give desired product 15.58 g (90%).

Example 2: Synthesis of Compound 13 from 15

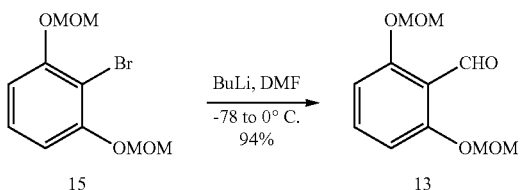

To a solution of 2-bromo-1,3-bis(methoxymethoxy)benzene (15) (19.9 g, 71.8 mmol) in THF (150 mL) at −78° C. was added BuLi (2.5 M, 31.6 mL, 79.0 mmol) dropwise. The solution was stirred at −78° C. for 25 min (resulting white cloudy mixture), then it was warmed to 0° C. and stirred for 25 min. The reaction mixture slowly turns homogenous. To the solution was added DMF at 0° C. After 25 min, HPLC showed reaction completed. The mixture was quenched with sat. NH4Cl (150 mL), diluted with ether (300 mL). The organic layer was separated, aq layer was further extracted with ether (2×200 mL), and organic layer was combined, washed with brine, dried and concentrated to give crude product, which was triturated to give 14.6 g desired product. The filtrate was then concentrated and purified by column to give additional 0.7 g, total mass is 15.3 g.

Example 3: Synthesis of Compound 13 from Resorcinol 11

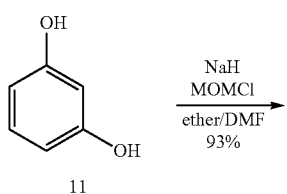

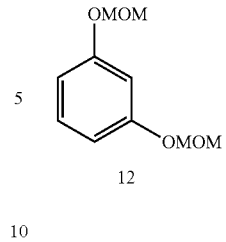

1.1 R:TMEDA, R:BuLi, S:THF, 2 h, -10° C.
1.2 1 h, 0° C.; 83%
  *OrgLett* 14(10), 2516-2519; 2012
OR:

1.1 R:TMEDA, R:BuLi,
  S:ME(CH2)4Me, rt, ? -10° C.
1.2 -10° C.; 2 h, -10° C.; -10° C. ? 0° C.
1.3 0° C.; 1 h, 0° C.
1.4 R:HCl, S:H2O
  84%
  *Journal of Organic Chemistry*,
  74(11). 4311-4317; 2009

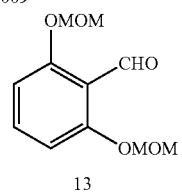

A three-necked round-bottom flask equipped with mechanical stirrer was charged with 0.22 mol of NaH (50% suspension in mineral oil) under nitrogen atmosphere. NaH was washed with 2 portions (100 mL) of n-hexane and then with 300 mL of dry diethyl ether; then 80 mL of anhydrous DMF was added. Then 0.09 mol of resorcinol 11, dissolved in 100 mL of diethyl ether was added dropwise and the mixture was left under stirring at rt for 30 min. Then 0.18 mol of MOMCl was slowly added. After 1 h under stirring at rt, 250 mL of water was added and the organic layer was extracted with diethyl ether. The extracts were washed with brine, dried (Na$_2$SO$_4$), then concentrated to give the crude product that was purified by silica gel chromatography to give compound 12 (93% yield).

A three-necked round-bottom flask was charged with 110 mL of n-hexane, 0.79 mol of BuLi and 9.4 mL of tetramethylethylendiamine (TMEDA) under nitrogen atmosphere. The mixture was cooled at −10° C. and 0.079 mol of bis-phenyl ether 12 was slowly added. The resulting mixture was left under magnetic stirring at −10° C. for 2 h. Then the temperature was raised to 0° C. and 0.067 mol of DMF was added dropwise. After 1 h, aqueous HCl was added until the pH was acidic; the mixture was then extracted with ethyl ether. The combined extracts were washed with brine, dried (Na$_2$SO$_4$), and concentrated to give aldehyde 13 (84%).

2,6-bis(methoxymethoxy)benzaldehyde (13): mp 58-59° C. (n-hexane); IR (KBr) n: 1685 (C=O) cm$^{-1}$; $^1$H-NMR (400 MHz, CDCl$_3$) δ 3.51 (s, 6H, 2 OCH$_3$), 5.28 (s, 4H, 2 OCH$_2$O), 6.84 (d, 2H, J=8.40 Hz, H-3, H-5), 7.41 (t, 1H, J=8.40 Hz, H-4), 10.55 (s, 1H, CHO); MS, m/e (relative intensity) 226 (M+, 3), 180 (4), 164 (14), 122 (2), 92 (2), 45 (100); Anal. Calc'd. for C$_{11}$H$_{14}$O$_5$: C, 58.40; H, 6.24. Found: C, 57.98; H, 6.20.

Example 4: The Synthesis of Compound 16

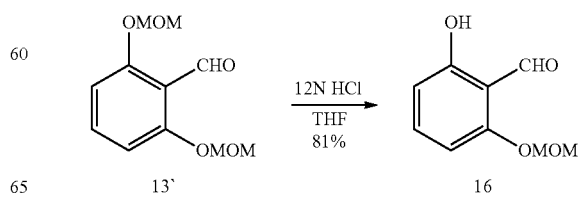

To a solution of 2,6-bis(methoxymethoxy)benzaldehyde (13) (15.3 g, 67.6 mmol) in THF (105 mL) (solvent was purged with $N_2$) was added conc. HCl (12N, 7 mL) under $N_2$, then it was further stirred under $N_2$ for 1.5 h. To the solution was added brine (100 mL) and ether (150 ml). The organic layer was separated and the aqueous layer was further extracted with ether (2×200 mL). The organic layer was combined, washed with brine, dried and concentrated to give crude product, which was purified by column (300 g, hexanes/EtOAc=85:15) to give desired product 16 (9.9 g) as yellow liquid.

Example 5: Synthesis of Compound 17

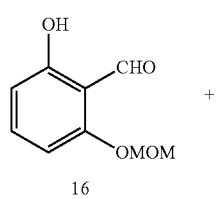

16

+

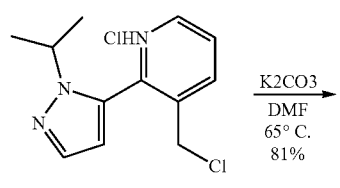

10

K2CO3
DMF
65° C.
81%

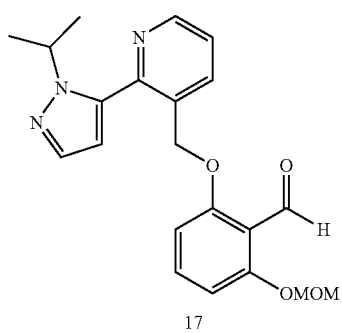

17

To a solution of 2-hydroxy-6-(methoxymethoxy)benzaldehyde (16) (10.88 g, 59.72 mmol) in DMF (120 mL) (DMF solution was purged with $N_2$ for 10 min) was added $K_2CO_3$ (32.05 g, 231.92 mmol) and 3-(chloromethyl)-2-(1-isopropyl-1H-pyrazol-5-yl)pyridine hydrochloride (10) (15.78 g, 57.98 mmol). The mixture was heated at 65° C. for 1.5 h, cooled to rt, poured into ice water (800 mL). The precipitated solids were isolated by filtration, dried and concentrated to give desired product (17, 18 g).

Example 6: Synthesis of Compound (I)

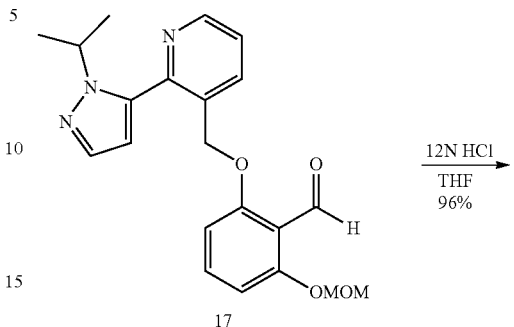

12N HCl
THF
96%

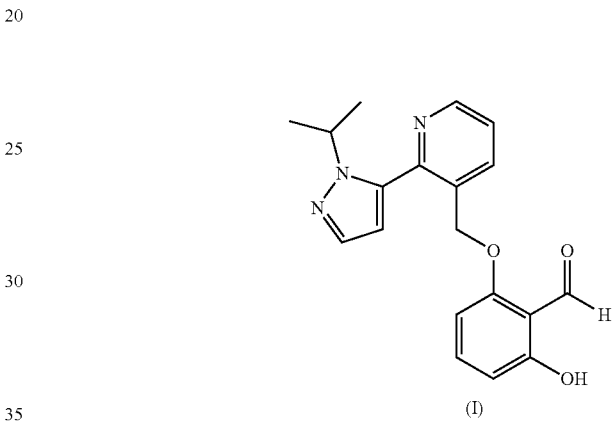

To a solution of 2-((2-(1-isopropyl-1H-pyrazol-5-yl)pyridin-3-yl)methoxy)-6-(methoxymethoxy)benzaldehyde (17) (18 g, 47.19 mmol) in THF (135 mL, solution was purged with $N_2$) was added conc. HCl (12N, 20 mL). The solution was stirred at rt for 3 h when HPLC showed the reaction complete. The mixture was added to a solution of $NaHCO_3$ (15 g) in water (1.2 L), and the resulting precipitate was collected by filtration, dried to give crude solid, which was further purified by column (DCM/EtOAc=60:40) to give pure product (15.3 g).

Example 7: Synthesis of Compound I (Free Base) and its HCl Salt Form

Compound (I) free base (40 g) was obtained from the coupling of the alcohol intermediate 7 and 2,6-dihydroxybenzaldedhye 9 under Mitsunobu conditions. A procedure is also provided below:

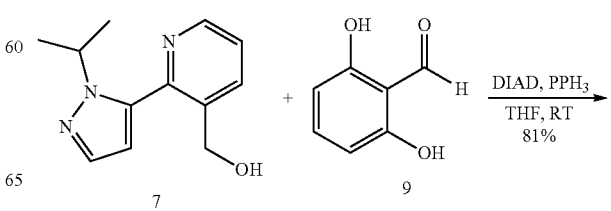

DIAD, PPH3
THF, RT
81%

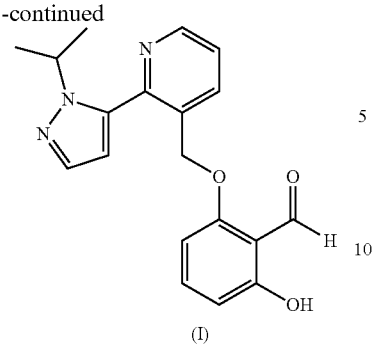

(I)

Example 8: Synthesis of Compound (I) by Mitsunobu Coupling

Into a 2000-mL three neck round-bottom flask, which was purged and maintained with an inert atmosphere of nitrogen, was placed a solution of [2-[1-(propan-2-yl)-1H-pyrazol-5-yl]pyridin-3-yl]methanol (7) (70 g, 322.18 mmol, 1.00 equiv) in tetrahydrofuran (1000 mL). 2,6-Dihydroxybenzaldehyde (9) (49.2 g, 356.21 mmol, 1.10 equiv) and PPh$_3$ (101 g, 385.07 mmol, 1.20 equiv) were added to the reaction mixture. This was followed by the addition of a solution of DIAD (78.1 g, 386.23 mmol, 1.20 equiv) in tetrahydrofuran (200 ml) dropwise with stirring. The resulting solution was stirred overnight at room temperature. The resulting solution was diluted with 500 ml of H$_2$O. The resulting solution was extracted with 3×500 ml of dichloromethane and the combined organic layers were dried over sodium sulfate and concentrated under vacuum. The residue was applied onto a silica gel column with EA:PE (1:50-1:3) as eluent to yield the crude product. The crude product was re-crystallized from i-propanol/H$_2$O in the ratio of 1/1.5. This resulted in 40 g (37%) of 2-hydroxy-6-([2-[1-(propan-2-yl)-1H-pyrazol-5-yl]pyridin-3-yl]methoxy)benzaldehyde as a light yellow solid. The compound exhibited a melting point of 80-82° C. MS (ES, m/z): 338.1 [M+1]. $^1$H NMR (300 MHz, DMSO-d6) δ 11.72 (s, 1H), 10.21 (s, 1H), 8.76 (d, J=3.6 Hz, 1H), 8.24 (d, J=2.7 Hz, 1H), 7.55 (m, 3H), 6.55 (m, 3H), 5.21 (s, 2H), 4.65 (m, 1H), 1.37 (d, J=5.1 Hz, 6H). $^1$H NMR (400 MHz, CDCl$_3$) δ 11.96 (s, 1H), 10.40 (s, 1H), 8.77 (dd, J=4.8, 1.5 Hz, 1H), 8.00 (d, J=7.8 Hz, 1H), 7.63 (d, J=1.8 Hz, 1H), 7.49-7.34 (m, 2H), 6.59 (d, J=8.5 Hz, 1H), 6.37 (d, J=1.8 Hz, 1H), 6.29 (d, J=8.2 Hz, 1H), 5.10 (s, 2H), 4.67 (sep, J=6.7 Hz, 1H), 1.50 (d, J=6.6 Hz, 6H).

In another approach, multiple batches of Compound (I) free base are prepared in multi gram quantities (20 g). The advantage of this route is the use of mono-protected 2,6-dihydroxybenzaldehyde (16), which effectively eliminates the possibility of bis-alkylation side product. The mono-MOM ether of 2,6-dihydroxybenzaldehyde (16) can be obtained from two starting points, bromoresorcinol (14) or resorcinol (11) [procedures described in the Journal of Organic Chemistry, 74(11), 4311-4317; 2009]. All steps and procedures are provided below. Due to the presence of phenolic aldehyde group, precautions (i.e., carry out all reactions under inert gas such as nitrogen) should be taken to avoid oxidation of the phenol and/or aldehyde group.

Preparation of compound I HCl salt: A solution of compound I (55.79 g, 165.55 mmol) in acetonitrile (275 mL) was flushed with nitrogen for 10 min, then to this solution was added 3N aqueous HCl (62 mL) at room temperature. The mixture was stirred for additional 10 min after the addition, most of the acetonitrile (about 200 mL) was then removed by evaporation on a rotary evaporator at around 32° C., the remaining solution was frozen by cooling in an acetone-dry ice bath and lyophilized to afford compound I HCl salt (59.4 g).

Example 9: Characterization of the HCl Salt of Compound 1

| Technique | Details | Result |
|---|---|---|
| XRPD | indexed | HCl salt of Compound 1 |
| Microscope | — | pale yellow solids, thin blades/tablets, birefringent |
| $^1$H NMR | DMSO-d6 | consistent with structure, <0.01 moles MEK |
| XRPD | — | HCl salt of Compound 1 |
| DVS | — | 0.03% gain upon equilibration at 5% RH |
| | | 0.10% gain from 5 to 95% RH |
| | | 0.09% loss from 95 to 5% RH |
| post XRPD | | HCl I + Free Base Form I |

Example 10: Physical Stability of the HCl Salt of Compound 1 Exposed to Water

| Condition | Time (all times are approximated) | Observation | XRPD Result |
|---|---|---|---|
| contacted w/ water | — | sheet formation after 5 min | — |
| water slurry | about 5 min | Floating yellow solids convert to white solids upon isolation | Free base (FB) I (indexed) |
| vacuum dried water slurry | about 1 day | Remain white, thin blades, birefringent (B) | FB I |
| | about 6 days | | FB I + FB II |

Example 11: Physical Stability of the HCl Salt of Compound 1 with Grinding

| Condition | Time | Observation | XRPD Result |
|---|---|---|---|
| grinding, dry | 30 min | off white/pale yellow | HCl I |
| grinding, wet | 30 min | off white/pale yellow paste | HCl I + FB I |

Example 12: Physical Stability of the HCl Salt of Compound 1 Exposed to Elevated Temperature and/or Vacuum

| Condition | Time | Observation | XRPD Result |
|---|---|---|---|
| RT vacuum | 6 days | pale yellow, blades/plates, B | HCl I + FB I |
| 30° C. | 6 hrs | pale yellow, blades/tablets, B | HCl I |
| | 12 hrs | pale yellow, blades/tablets, B | HCl I + FB I |
| | 24 hrs | pale yellow, blades/tablets, B | HCl I + FB I |
| 40° C. | 6 hrs | pale yellow, blades/tablets, B | HCl I + FB I |
| | 12 hrs | pale yellow, blades/tablets, B | HCl I + FB I |
| | 24 hrs | pale yellow, blades/tablets, B | HCl I + FB I |
| 40° C. vacuum | 6 hrs | pale yellow, blades/tablets, B | HCl I + FB I |
| | 12 hrs | pale yellow, blades/tablets, B | HCl I + FB I |
| | 24 hrs | pale yellow, blades/tablets, B | HCl I + FB I |

| Condition | Time | Observation | XRPD Result |
| --- | --- | --- | --- |
| 60° C. | 6 days | pale yellow blades, B | HCl I + FB I |
| 60° C. vacuum | 6 days | pale yellow, blades, B; irregular residue | HCl I + FB I + other free base form |
| 100 to 125° C. | 20 min | pH paper above sample indicate acidic volatiles | HCl I + FB I + other free base form |

Example 13: Generation of the Free Base of Compound 1 from the Disproportionation of the HCl Salt of Compound 1 in Water (the Starting Material is the HCl Salt of Compound 1)

| Method | Observation | XRPD Result |
| --- | --- | --- |
| 1. contacted with water<br>2. sonicated<br>3. filtered and rinsed with water<br>4. dried under N₂ for 10 minutes<br>5. vacuum RT, overnight | 1. pale yellow, wets poorly<br>2. white<br>3. —<br>4. —<br>5. — | FB I |
| 1. contacted with water<br>2. sonicated for 5 minutes<br>3. slurried for 10 minutes<br>4. filtered, rinsed with water<br>5. dried under N₂ for 10 minutes<br>6. vacuum RT, overnight<br>7. stored in freezer | 1. —<br>2. pale yellow, turned white<br>3. —<br>4. —<br>5. white<br>6. —<br>7. — | FB I + other free base form |
| 1. slurry in water, RT, 8 days; seeded with FB II<br>2. filtered, rinsed with water<br>3. vacuum RT, overnight | 1. thick white slurry<br>2. —<br>3. — | FB II |
| 2. sub sample of slurry<br>3. rinsed with water | 2. —<br>3. — | FB II (indexed) |

Example 14: Characterization Form I of the Free Base of Compound 1

| Technique | Details | Result |
| --- | --- | --- |
| XRPD | indexed | Free Base Form I |
| XRPD | — | Free Base Form I |
| TGA | 25 to 350° C. | 0.2% weight loss up to 100° C. |
| DSC | 25 to 350° C. | endothermic event with onset near 97° C. |
| Hot Stage Microscopy | 22.7° C. | initial, fines, birefringent |
| | 91.2° C. | increase in particle size and birefringence |
| | 94.2° C. | increase in particle size and birefringence |
| | 95.7° C. | melt onset, larger particles from initial heating |
| | 96.1° C. | melt continuation |
| | 96.3° C. | melt complete, no crystallization upon melting |
| | 68.7° C. | fresh preparation, larger magnification |
| | 91.1° C. | increase in birefringence |
| | 94.8° C. | melt onset, larger particles, birefringent |
| | 95.4° C. | melt continuation |
| | 95.9° C. | only few crystals remain, cooled to 92.6° C. |
| | 92.6° C. | held for 2 to 3 minutes crystal growth to larger blades, - began heating |
| | 96.3° C. | complete melt |
| ¹H NMR | DMSO-d6 | consistent with structure |
| DVS | — | 0.02% loss upon equilibration at 5% RH<br>0.22% gain from 5 to 95% RH |

| Technique | Details | Result |
| --- | --- | --- |
| post XRPD | | 0.22% loss from 95 to 5% RH<br>Free Base Form I + other Free Base Material |

Example 15: Characterization of Form II of the Free Base of Compound 1

| Technique | Details | Result |
| --- | --- | --- |
| XRPD | indexed | Free Base Form II |
| XRPD | initial after 7 days | Free Base Form II |
| TGA | 25 to 350° C. | 0.1% weight loss up to 100° C. |
| DSC | 25 to 350° C. | endothermic event with onset near 97° C. |
| ¹H NMR | DMSO-d6 | consistent with structure |

Example 16: Characterization of Material N of the Free Base of Compound 1

| Technique | Details | Result |
| --- | --- | --- |
| XRPD | — | Free Base Material N |
| TGA | 25 to 350° C. | 0.2% weight loss up to 100° C. |
| DSC | 25 to 350° C. | endothermic event with onset near 94° C. |
| ¹H NMR | DMSO-d6 | consistent with structure, no residual reaction solvent observed |

Example 17: Competitive Interconversion Slurries Between Free Base Forms I and II

| Conditions | Solvent | Observation | XRPD Result |
| --- | --- | --- | --- |
| 6° C., 6 days | water | white | FB II |
| 6° C., 6 days | heptane | white | FB II |
| 6° C., 6 days | IPE | faint pale yellow | FB N |
| RT, 6 days | water | white | FB II |
| RT, 6 days | heptane | off white | FB II |
| RT, 6 days | IPE | pale yellow | FB N[Error! Bookmark not defined.] |
| RT, 6 days | toluene | pale yellow | FB N |
| 57° C., 2 days | water | fines, off white, B | FB II + FB I |
| 57° C., overnight | heptane | blades and tablets, B | FB II |
| 57° C., overnight | IPE | blades, laminated, pale yellow, B | FB II |

Example 18: Competitive Interconversion Slurries Between Free Base Form II and Material N

| Conditions | | | |
| --- | --- | --- | --- |
| 35° C., 3 days | heptane | pale yellow fines, B | FB N |
| 57° C., 3 days | heptane | larger blades, and rosettes of blades, B | FB II |

Example 19: Selected Experimental Methods

Indexing: XRPD patterns are indexed by using proprietary SSCI software. Agreement between the allowed peak positions, marked with red bars within the figures, and the observed peaks indicates a consistent unit cell determination. Indexing and structure refinement are computational studies which are performed under the "Procedures for SSCI Non-cGMP Activities." To confirm the tentative indexing solution, the molecular packing motifs within the crystallographic unit cells must be determined. No attempts at molecular packing were performed.

Differential Scanning Calorimetry (DSC):

DSC was performed using a TA Instruments Q2000 differential scanning calorimeter. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. The data acquisition parameters and pan configuration for each thermogram are displayed in the image in the Data section of this report. The method code on the thermogram is an abbreviation for the start and end temperature as well as the heating rate; e.g., −30-250-10 means "from −30° C. to 250° C., at 10° C./min". The following summarizes the abbreviations used in each image for pan configurations: Tzero crimped pan (T0C); and Lid not crimped (NC).

Dynamic Vapor Sorption (DVS):

Dynamic vapor sorption (DVS) data were collected on a VTI SGA-100 Vapor Sorption Analyzer. NaCl and PVP were used as calibration standards. Samples were not dried prior to analysis. Adsorption and desorption data were collected over a range from 5 to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Microscopy

Hot Stage Microscopy:

Hot stage microscopy was performed using a Linkam hot stage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20×0.40 N.A. long working distance objective with crossed polarizers and a first order red compensator. Images were captured using SPOT software (v. 4.5.9).

Polarized Light Microscopy:

During the course of experimentation generated samples were viewed utilizing a microscope with cross polarized light to observe morphology and birefringence. Samples were visually observed at 40× magnification.

$^1$H Solution Nuclear Magnetic Resonance ($^1$H NMR)

SSCI:

Samples were prepared for NMR spectroscopy as ~5-50 mg solutions in the appropriate deuterated solvent. The specific acquisition parameters are listed on the plot of the first full spectrum of each sample in the data section for samples run at SSCI.

Spectral Data Solutions:

For samples run using Spectral Data Solutions (subcontractor), the solution $^1$H NMR spectra were acquired at ambient temperature on a Varian $^{UNITY}$INOVA-400 spectrometer ($^1$H Larmor Frequency=399.8 MHz). The specific acquisition parameters are listed on the spectral data sheet and on each data plot of the spectrum of the sample.

Thermogravimetric Analysis (TGA)

TG analyses were performed using a TA Instruments 2950 thermogravimetric analyzer. Temperature calibration was performed using nickel and Alumel™. Each sample was placed in an aluminum pan and inserted into the TG furnace. The furnace was heated under a nitrogen purge. The data acquisition parameters are displayed above each thermogram in the Data section of this report. The method code on the thermogram is an abbreviation for the start and end temperature as well as the heating rate; e.g., 25-350-10 means "from 25° C. to 350° C., at 10° C./min". The use of 0 as the initial temperature indicates sample run initiated from ambient.

XRPD Analysis

INEL:

XRPD patterns were collected with an Inel XRG-3000 diffractometer. An incident beam of Cu Kα radiation was produced using a fine-focus tube and a parabolically graded multilayer mirror. Prior to the analysis, a silicon standard (NIST SRM 640d) was analyzed to verify the Si 111 peak position. A specimen of the sample was packed into a thin-walled glass capillary, and a beam-stop was used to minimize the background from air. Diffraction patterns were collected in transmission geometry using Windif v. 6.6 software and a curved position-sensitive Equinox detector with a 2θ range of 120°. The data-acquisition parameters for each pattern are displayed above the image in the Data section of this report.

PANalytical Transmission:

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the Si 111 peak position. A specimen of the sample was sandwiched between 3 μm thick films and analyzed in transmission geometry. A beam-stop, short antiscatter extension, and an antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data-acquisition parameters for each pattern are displayed above the image in the Data section of this report including the divergence slit (DS) before the mirror and the incident-beam antiscatter slit (SS).

PANalytical Reflection:

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640d) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b. The data acquisition parameters for each pattern are displayed above the image in the Data section of this report including the divergence slit (DS) and the incident-beam SS.

Approximate Solubility:

A weighed sample was treated with aliquots of the test solvent at room temperature. The mixture was sonicated between additions to facilitate dissolution. Complete dissolution of the test material was determined by visual inspection. Solubility was estimated based on the total solvent used to provide complete dissolution. Some samples were then heated and observed visually for complete dissolution. The actual solubility may be greater than the value calculated because of the use of solvent aliquots that were too large or due to a slow rate of dissolution. The solubility is expressed as "less than" if dissolution did not occur during the experiment. If complete dissolution was achieved as a result of only one aliquot addition, the solubility is expressed as "greater than".

Anti-Solvent Additions:

Compound 1/organic solvent solutions were contacted with solvents that Compound 1 was determined to be poorly soluble or insoluble in. These anti solvent additions were added to help lower the solubility of the solvent system and induce crystallization.

Cooling and Slow Cools:

Solutions were prepared in the selected solvent or solvent/anti-solvent system. These solutions were chilled below room temperature within a refrigerator for varying lengths of time in an attempt to induce nucleation. The presence or absence of solids was noted. Upon observation of solids, in quantities sufficient for analysis, isolation of material was conduction. If insufficient quantities were present further cooling was performed in a freezer. Samples were either isolated for analysis wet or as dry powders.

Compression:

Selected samples were compressed utilizing a KBr die and a Carver hydraulic press. An applied load of 10000 lbs was applied to the die shaft for approximately 20 minutes.

Crystallization from Solution:

Saturated solutions were generated at ambient and then capped. Nucleation was observed to occur from these systems during evaluation of the Free Base of Compound 1.

Fast Evaporation:

Solutions were prepared in selected solvents and agitated between aliquot additions to assist in dissolution. Once a mixture reached complete dissolution, as judged by visual observation, the solution was allowed to evaporate at ambient temperature in an uncapped vial or at ambient under nitrogen. The solids that formed were isolated for evaluation.

Milling:

Selected material was milled utilizing a Reitch Mill. The material was loaded into an agate lined milling vessel followed by the addition of an agate ball. The vessel was then placed on to the mill and milled for approximately 30 minutes at frequency of 1/30 seconds. The milling was stopped approximately every 10 minutes and material scraped from the wall before further milling.

Slurry:

Solutions were prepared by adding enough solids to a given solvent so that excess solids were present. The mixture was then agitated in a sealed vial at either ambient or an elevated temperature. After a given amount of time, the solids were isolated for analysis.

Temperature and Relative Humidity Stress:

Selected materials were stressed at elevated related humidity and/or temperature. Relative humidity jars (saturated salt solutions used to generate desired relative humidity) were utilized to store selected samples. The following relative humidity jars were utilized during evaluation: 75% RH (NaCl) and 60% (NaBr), to investigate the effects of humidity. Temperatures utilized were ambient, 30, 40, 60, and 100-125° C.

Vacuum:

Selected materials were stressed under reduced pressure for a set time period. Initial stressing was conducted with the in-house vacuum system with absolute pressure readings <500 mTorr, typically 30 to 50 mTorr (0.030 to 0.05 mm Hg). Additional vacuum stressing was conducted at 48 mmHg utilizing a portable lab vacuum and bleed to simulate conditions similar to those expected during process.

Example 20: Disproportionation of the HCl Salt

The disproportionation of the HCl salt in water was utilized to generate free base. The nucleation of Free Base Form I occurs first. Extending the slurry time induces the transformation to a more thermodynamically stable phase relative to Form I, Free Base Form II.

Three anhydrous materials of the free base were identified; Free Base Forms I, II, and Material N. Free Base Material N appears to be most stable form, relative to Forms I and II, at room temperature. Free Base Material N is enantiotropic relative to Form II, and will transform reversibly at a specific transition temperature (estimated near 42° C.). Above the transition temperature, Free Base Form II appears to be the most stable form, relative to Form I and Material N.

The HCl salt (termed "HCl Form I") was subjected to various stress conditions and monitored by XRPD to evaluate physical stability. As discussed, disproportionation occurred during the DVS experiment of the HCl salt, indicating instability upon exposure to elevated humidity. Disproportionation is further evident with wet milling or in direct contact with water (e.g. slurry) as shown by the presence of Free Base Forms I or II, identified by XRPD. The volatilization and loss of HCl upon heating and/or vacuum is shown by the presence of Free Base Form I, identified by XRPD, and also indicates instability at these conditions.

Contact with water resulted in a visual color change of the material from pale yellow to white; physical changes were also observed microscopically. Immediate disproportionation occurs. XRPD analysis identified the resulting material from a water slurry (~5 minutes) as Free Base Form I. Free Base Form II also becomes evident if the amount of time in the slurry is extended.

The volatilization of HCl was evident within hours of exposure to drying conditions. Conversion to Free Base Form I was observed by XRPD at 30° C. (after 12 hrs), 40° C. (after 6 hrs), and at 40° C./48 mmHg (after 6 hrs).

Free Base Material C becomes evident at more extreme conditions involving elevated temperatures. Heating HCl Form I up to 125° C. induces the loss of acidic volatiles (judged visually by use of pH paper held above sample). XRPD analysis identifies the resulting sample as a mixture of HCl Form I, Free Base Form I, and Free Base Material C. Exposing the HCl salt to 60° C. under vacuum for 6 days provides the same result. The nature of Material C is not established The HCl salt was shown to disproportionate immediately in water. This phenomenon was utilized to generate free base. The nucleation of Free Base Form I occurs first.

Extending the slurry time induces the transformation to a more thermodynamically stable phase relative to Form I, Free Base Form II.

A 20 ml vial was charged with 266.4 mg of HCl Form I and contacted with 10 ml of water. The sample was sonicated until the pale yellow material changed color to white. The resulting solids were collected by filtration (water aspirated) and rinsed with 10 ml of water. A nitrogen purge was blown over the sample for approximately 10 minutes prior to exposure to vacuum at ambient temperature to dry overnight. The resulting material was analyzed by XRPD and determined to be Free Base Form I.

A 250 ml Erlenmeyer flask was charged with 6.0250 grams of HCl Form I and contacted with 220 mL of water. The sample was sonicated for approximately 5 minutes to disperse the material. The yellow material changed color to white during sonication. A stir bar was added and the sample was stirred at 700 RPM for approximately 10 minutes. The solids were collected by filtration and rinsed with 220 ml of water followed by a nitrogen purge over the sample for approximately 10 minutes prior to exposure to vacuum at ambient temperature. The sample was dried at this condition for approximately 24 hours yielding 5.1834 grams of material. The resulting material was analyzed by XRPD and determined to be a mixture of Free Base Form I and Free Base Material D. (The nature of Material D is not established.)

The procedure used to generate Free Base Form II is described below.

A 20 ml vial was charged with 477.5 mg of HCl Form I lot 20 and contacted with 20 ml of water. The sample was sonicated until the pale yellow material changed color to white. A small amount of sample (mixture of Free Base Forms I and II) was added as seeds. A stir bar was added and the sample was stirred at 200 RPM for 8 days. The resulting solids were collected by filtration (water aspirated) and rinsed with 15 ml of water. The sample was exposed to vacuum at ambient temperature to dry overnight. The resulting material was analyzed by XRPD and determined to be Free Base Form II.

Example 21: Additional Procedures for the Preparation of the Free Base of Form I, Form II, and from N Conversion of the Free Base of Compound 1 to the HCl Salt
General Procedure:
Slowly treat a solution of the free base of Compound 1 in MEK (5 vol) with conc HCl (1.5 eq). Cool the resulting slurry to 0-5° C. for 1 h and filter. Wash solids with MEK (1 vol). Dry under vacuum at 30-35° C.

Preparation A:
Following the general procedure above, 35 g of crude Compound 1 was processed to provide the HCl salt as a pale yellow solid (32.4 g, 82% yield, 99.8% purity by HPLC).

Preparation of the Free Base Form I from the HCl Salt of Compound 1
General Procedure: Vigorously stir a slurry of the HCl salt of Compound 1 in DIW (10 vol) for 5 min to 2 h. Filter the slurry, wash with DIW (2×1 vol), dry on funnel, then further dry under vacuum at 30-35° C.

Preparation A:
Following the general procedure above, after stirring for 1 h, 32 g of the HCl salt of Compound 1 was processed to provide the free base as a pale yellow solid (27.3 g, 95% yield, 99.8% purity by HPLC; DSC indicates Form I).

Preparation B:
Following the general procedure above, after stirring for 1 h, 39 g of the HCl salt of Compound 1 was processed to provide the free base as a pale yellow solid (31.8 g, 90% yield, >99.9% purity by HPLC)).

Preparation C:
Thus, the HCl salt of Compound 1 (134 g) was vigorously stirred in water (10 vol) until the material appeared as a finely dispersed white slurry. After filtration and drying, a white crystalline solid (116 g, 96% recovery, >99.9% purity by HPLC) was isolated.

Preparation D:
The purpose of this experiment was to prepare the free base from Compound 1, HCl. Thus, the HCl salt of Compound 1 (65.3 g) was vigorously stirred in water (10 vol) until the material appeared as a finely dispersed white slurry. After filtration and drying, a white crystalline solid (57.5 g, 97.6% recovery, >99.9% purity by HPLC) was isolated.

Preparation of GBT000440 Free Base Form II from GBT000440 Free Base Form I
General Procedure:
Stir a slurry of the free base of Compound 1 Form I in an appreciate solvent (e.g. heptane or water) (10 vol) for 1-7 days. Filter the slurry, wash with DIW (2×1 vol), dry on funnel, then further dry under vacuum at 30-35° C.

Preparation A:
Thus, the free base of Compound 1, Form I (114 g) was stirred in n-heptane (10 vol) at 35° C. After 4 days, XRPD indicated the material was Form II. The slurry was filtered and dried to provide 110 g off white solid.

Preparation B:
the free base of Compound 1 (5 g) was slurried in heptanes (10 vol 50 mlL) at room temperature. After 4 days, the slurry was filtered to provide an off-white solid.

Preparation C:
the free base of Compound 1 (5.8 kg) was slurried in heptanes (10 vol) at room temperature. After 2 days, the slurry was filtered and washed with 2×2 vol n-heptane to provide 4.745 kg of Form II as an off-white solid.

Preparation D:
the free base of Compound 1 (5 g) was slurried in water. After 4 days, the slurry was filtered to provide an off-white solid.

Preparation of GBT000440 Free Base Form N from GBT000440 Free Base Form I or Form II
General Procedure:
Stir a slurry of the free base of Compound 1, Form I in MTBE (4 vol) at room temperature for at least 4 days. After 4 days, filter the slurry to provide an off-white solid. Obtain XRPD to confirm polymorph as Material N.

Preparation A:
Following the general procedure above, 27 g of the free base of Compound 1, Form I (48TRS079) was stirred in MTBE at 18-23° C. for 4 days. DSC indicated it should be Material N. Isolated 22.2 g cream colored solid (82% recovery, 99.9 purity by HPLC). XRPD analysis planned.

Preparation B:
Following the general procedure above, 31 g of the free base of Compound 1, Form I was stirred in 3 vol MTBE at 18-23° C. for 4 days.

Preparation C: the free base of Compound 1, Form I (13KWB023, 1 g) was slurried in MTBE (5 vol) at room temperature. Slurry was seeded with Material N (50 mg).

After 4 days, the slurry was filtered to provide a off-white solid. DSC indicated the melting point was the same as Material N.

Preparation D:

The purpose of this experiment was to convert the free base of Compound 1, Form II to Material N. Thus, the free base of Compound 1 (0.5 g) was stirred in 5 vol of di-n-propyl ether at 18-23° C. After 2 days, DSC corresponded to the pattern observed for Material N. XRPD analysis confirmed Material N had been formed.

Preparation E:

To the free base of Compound 1, Form II (5 g) was added diisopropyl ether (5 vol, 25 mL) at room temperature. After 4 days, the slurry was filtered to provide a off-white solid. DSC indicates Material N.

Example 22: Preliminary Solvent-Based Screens

Rapid, solvent-based screens were conducted in an attempt to determine the most stable form of the free base of Compound 1. The study also provides a preliminary assessment of the propensity of these materials to exist in various crystal forms. Generated solids were observed by polarized light microscopy (PLM) and/or analyzed by X-ray powder diffraction (XRPD), comparing the resulting XRPD patterns to known patterns of Compound 1.

If possible, XRPD patterns were indexed. Indexing is the process of determining the size and shape of the crystallographic unit cell given the peak positions in a diffraction pattern. The term gets its name from the assignment of Miller index labels to individual peaks. XRPD indexing serves several purposes. If all of the peaks in a pattern are indexed by a single unit cell, this is strong evidence that the sample contains a single crystalline phase. Given the indexing solution, the unit cell volume may be calculated directly and can be useful to determine their solvation states. Indexing is also a robust description of a crystalline form and provides a concise summary of all available peak positions for that phase at a particular thermodynamic state point.

Materials exhibiting unique crystalline XRPD patterns, based on visual inspection of peaks associated with these materials, were given letter designations. The letter designation is tentatively associated with the word 'Material' if insufficient characterization data is available. The nomenclature is used only to aid in the identification of unique XRPD patterns and does not imply that the stoichiometry, crystalline phase purity, or chemical purity of the material is known. Materials are further designated as forms with Roman numeral designations (i.e., Free Base Material A=Free Base Form I), when phase purity (obtained through indexing of the XRPD pattern or single crystal structure elucidation) and chemical identity/purity (obtained through proton NMR spectroscopy) of the material is determined.

Three anhydrous materials were identified: Forms I, II, and Material N. Material N appears to be most stable form, relative to Forms I and II, at room temperature. Material N is enantiotropic relative to Form II, and will transform reversibly at a specific transition temperature (estimated near 42° C.). Above the transition temperature, Form II appears to be the most stable form, relative to Form I and Material N.

Materials C and D are used to identify a few additional, low intensity peaks observed in XRPD patterns which were predominantly composed of the Free Base Form I of Compound 1 or mixtures of the HCl Form I and Free Base Form I of Compound 1.

Example 23: Anhydrous Ansolvate Forms

Form I

Free Base Form I is a metastable, anhydrous phase of the free base that is formed immediately from the disproportionation of the HCl salt in water. A representative XRPD pattern of Form I was successfully indexed and the unit cell volume is consistent with anhydrous free base. Visual comparison of the XRPD pattern to the historical pattern of the free base provided indicates the material may be similar; however, the historical pattern appears to exhibit additional peaks from a potential mixture.

The $^1$H NMR spectrum is consistent with the chemical structure of Compound 1. The chemical shift at approximately 2.5 ppm is assigned to DMSO (due to residual protons in the NMR solvent). Peaks that could be associated with residual solvents were not visible, consistent with the anhydrous unit cell volume determined from the indexing solution above and the negligible wt % loss observed by TGA discussed below.

Thermograms (TG) data shows negligible weight loss, 0.2%, up to 100° C., consistent with an anhydrous form. The DSC exhibits a single endotherm with an onset near 97° C. (similar to what is observed for Form II). The endotherm is consistent with a melt by hot stage microscopy. However, changes in particle size and birefringence were evident prior to the melt; a possible phase change occurred. Consequently, if a phase change occurred and an endotherm similar to that of Free Base Form II was observed, it can be inferred that the observed melt is truly not of Form I but of the resulting phase, most likely Form II.

The DVS isotherm indicates Form I is not hygroscopic. Negligible weight gain and loss, 0.2%, was observed through sorption/desorption. By XRPD, the material recovered from the DVS experiment was predominately Free Base Form I with a few additional peaks. The additional peaks were termed Free Base Material D. The nature of Material D is unknown; however, the appearance of another phase(s) indicates that Form I is not likely physically stable at elevated humidity conditions (at ambient temperature).

Form II

Free Base Form II is an anhydrous phase of the free base. Form II is enantiotropically related to Material N, where it is the thermodynamically stable form above an estimated transition temperature of 42° C. Form II can be generated in solvents that do not form known solvates; such as heptane, IPE, MTBE, or toluene; through short-term slurry conversions of Form I (where the crystallization kinetics delay the nucleation of the more stable form) or elevated temperature slurries (above 42° C.). A representative XRPD pattern of Form II was successfully indexed and the unit cell volume is consistent with anhydrous free base of Compound 1.

The $^1$H NMR spectrum is consistent with the chemical structure of Compound 1. The chemical shift at approximately 2.5 ppm is assigned to DMSO (due to residual protons in the NMR solvent). Peaks that could be associated with residual solvents were not visible, consistent with the anhydrous unit cell volume determined from the indexing solution above and the negligible wt % loss observed by TGA discussed below.

Thermograms (TG) data show negligible weight loss, 0.1%, up to 100° C., consistent with an anhydrous form. The DSC exhibits a single endotherm (80.1 J/g) with an onset near 97° C.

Form II remained unchanged after 7 days at ambient storage, through reanalysis by XRPD. The form is known to be thermodynamically metastable, relative to Material N, at this condition; however, the kinetics of polymorph conversion may be slow at ambient conditions in the solid state.

Material N

Free Base Material N is an anhydrous phase of the free base. Material N is enantiotropically related to Form II, where it is the thermodynamically stable form below an estimated transition temperature of 42° C. Given the opportunity, Material N can be generated through slurries in solvents that do not form known solvates; such as heptane, IPE, MTBE, or toluene; at temperatures below 42° C. The following is an example of a laboratory scale procedure used to generate Free Base Material N.

53.0 mg of Free Base Form I was contacted with 2 ml of an IPE/free base solution (concentration 13 mg/ml). A stir bar was added and the sample was slurried for 7 days at ambient. The solution was decanted from the sample and the remaining solids briefly dried under nitrogen. Characterization Data indicates Material N is a unique crystalline phase.

The $^1$H NMR spectrum is consistent with the chemical structure of Compound 1. The chemical shift at approximately 2.5 ppm is assigned to DMSO (due to residual protons in the NMR solvent). Peaks that could be associated with residual solvents were not visible, consistent with the negligible wt % loss observed by TGA discussed below.

Thermograms (TG) data show negligible weight loss, 0.2%, up to 100° C., consistent with an anhydrous form. The DSC exhibits a single endotherm (82.8 J/g) with an onset at 94° C.

Tentative Determination of the Thermodynamic Relationship between Free Base Forms I, II, and Material N Characterization data indicates that Forms I, II, and Material N are unique crystalline phases; however, only the XRPD patterns of Forms I and II were successfully indexed to confirm phase purity. Therefore, any proposed thermodynamic relationship between these materials is a working hypothesis, where the phase purity of Material N is assumed.

Phase transitions of solids can be thermodynamically reversible or irreversible. Crystalline forms which transform reversibly at a specific transition temperature ($T_p$) are called enantiotropic polymorphs. If the crystalline forms are not interconvertable under these conditions, the system is monotropic (one thermodynamically stable form). Several rules have been developed to predict the relative thermodynamic stability of polymorphs and whether the relationship between the polymorphs is enantiotropic or monotropic. The heat of fusion rule is applied within this study. The heat of fusion rule states that if the higher melting form has the lower heat of fusion then the two forms are enantiotropic, otherwise they are monotropic.

Material N appears to be most stable form, relative to Forms I and II, at room temperature. Based on the heats of fusion and melts determined by DSC, Material N is enantiotropic relative to Form II, and will transform reversibly at a specific transition temperature ($T^{N-II}$). Due to a possible phase change of Form I to Form II that occurred prior to the observed endotherm in the DSC, the relationship of Form I with either Material N or Form II cannot be conclusively determined through the heat of fusion rule. However, through various interconversion slurries, it was shown that Form I is the least thermodynamically stable form between 6° C. and $T^{N-II}$. In addition, assuming that Form I spontaneously converted to Form II in the DSC at elevated temperatures (prior to the observed melt), it must follow that Form II is also more stable than Form I above $T^{N-II}$.

Example 24: Estimated Transition Temperature

The estimated transition temperature between two enantiotropically related forms can be calculated from their melt onsets and heats of fusion based on the equation shown below.

$$T_p = \frac{\Delta H_{f,2} - \Delta H_{f,1} + (C_{p,liq} - C_{p,1}) \cdot (T_{f,1} - T_{f,2})}{\frac{\Delta H_{f,2}}{T_{f,2}} - \frac{\Delta H_{f,1}}{T_{f,1}} + (C_{p,liq} - C_{p,1}) \cdot \ln\left(\frac{T_{f,1}}{T_{f,2}}\right)}$$

Where, $(C_{p,liq} - C_{p,1}) = k \cdot \Delta H_{f,1}$ and $k=0.005$

Between Material N and Form II, the equation estimates a transition temperature of 42° C. To summarize, the relative stability of the forms from most to least stable is shown below.

| Temperature Range* | Relative Stability | Comments |
|---|---|---|
| Below 6° C. | N > II | Relationships to Form I are not established below this temp |
| Between 6° C. and $T^{N-II}$ | N > II > I | — |
| Above $T^{N-II}$ | (II > N) and (II > I) | Relationship between Form I and Material N is not established above this temp |

*$T^{N-II}$ is estimated to be near 42° C.

Example 25: Energy-Temperature Diagram

Figure 17:
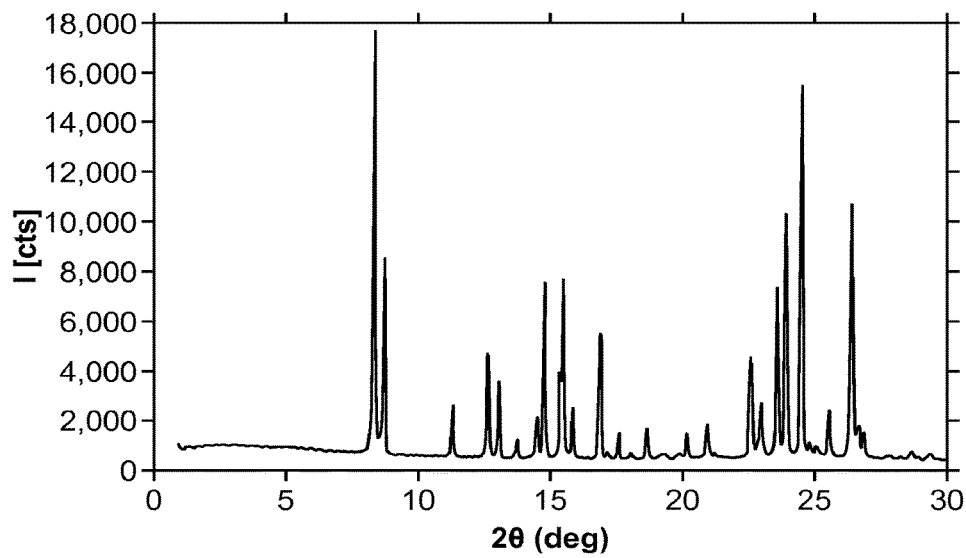
FIG. 17 depicts a contemplated XRPD profile for solvated Material F.
Figure 18:
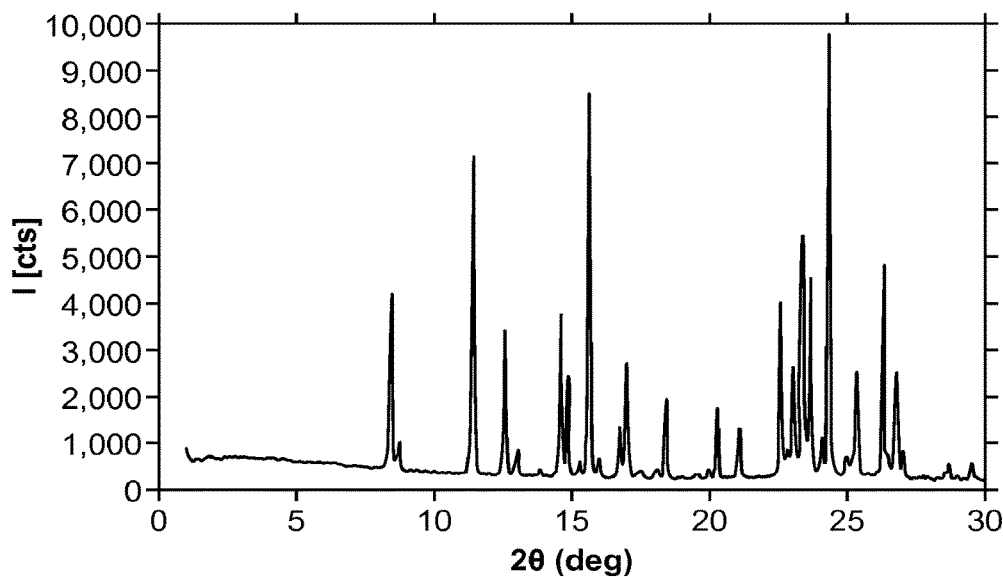
FIG. 18 depicts a contemplated XRPD profile for solvated Material G.
Figure 19:
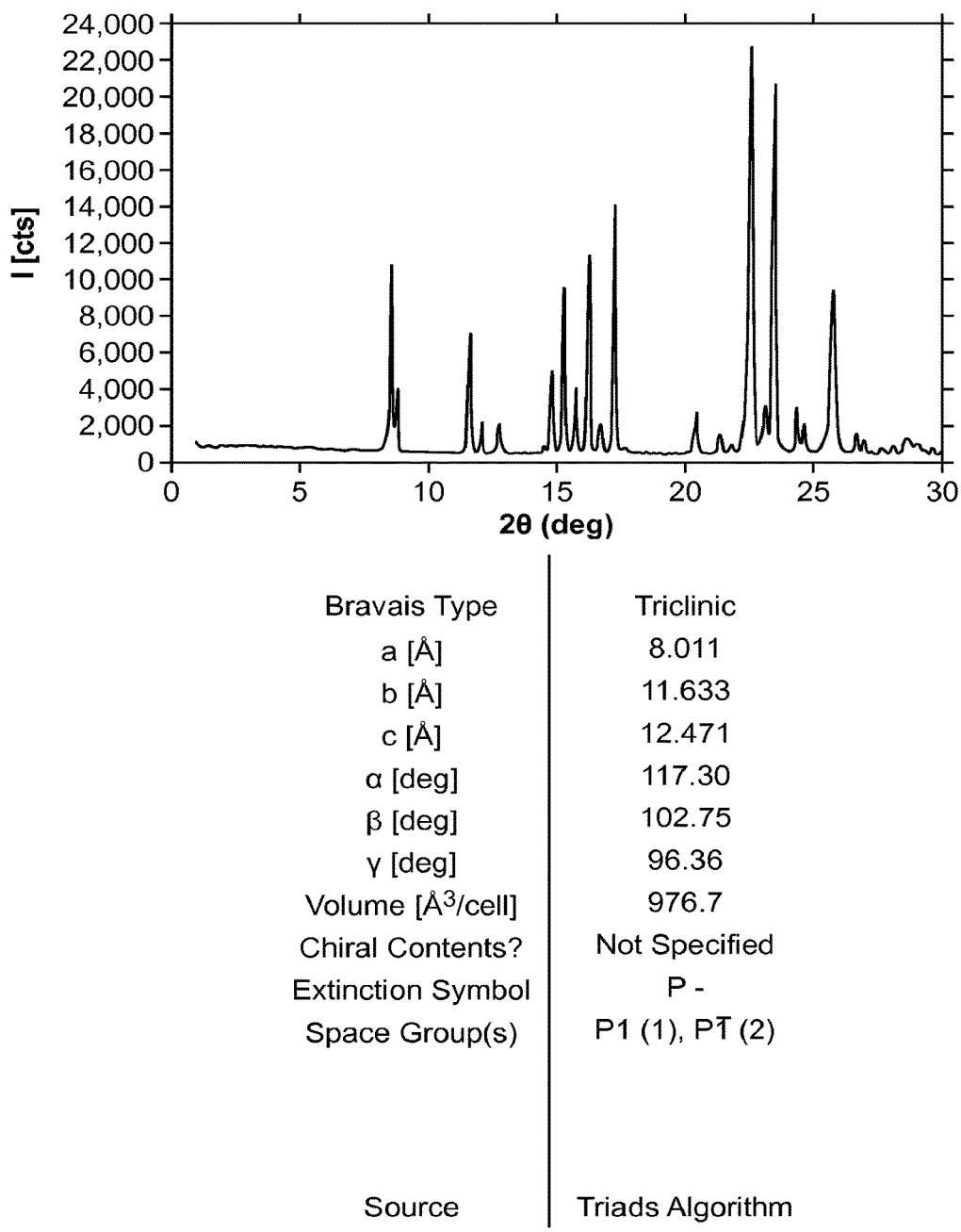
FIG. 19 depicts a contemplated XRPD profile for solvated Material H.
Figure 20:
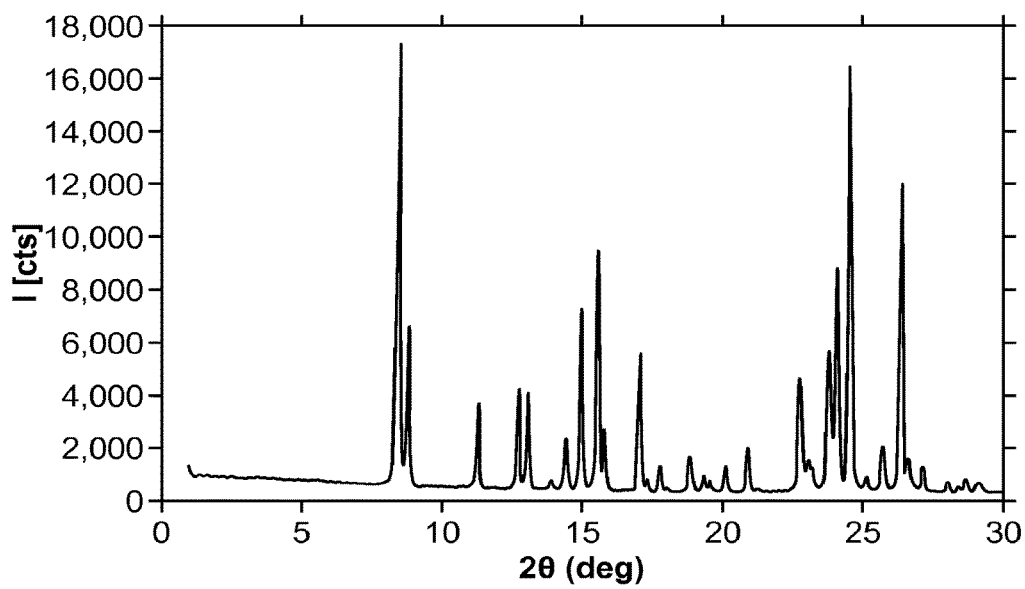
FIG. 20 depicts a contemplated XRPD profile for solvated Material J.
Figure 21:
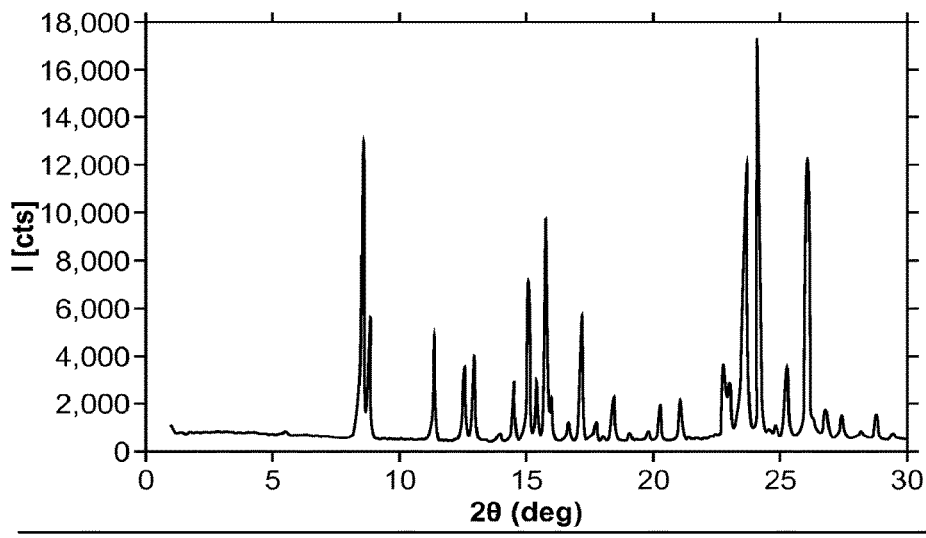
FIG. 21 depicts a contemplated XRPD profile for solvated Material K.
Figure 22:
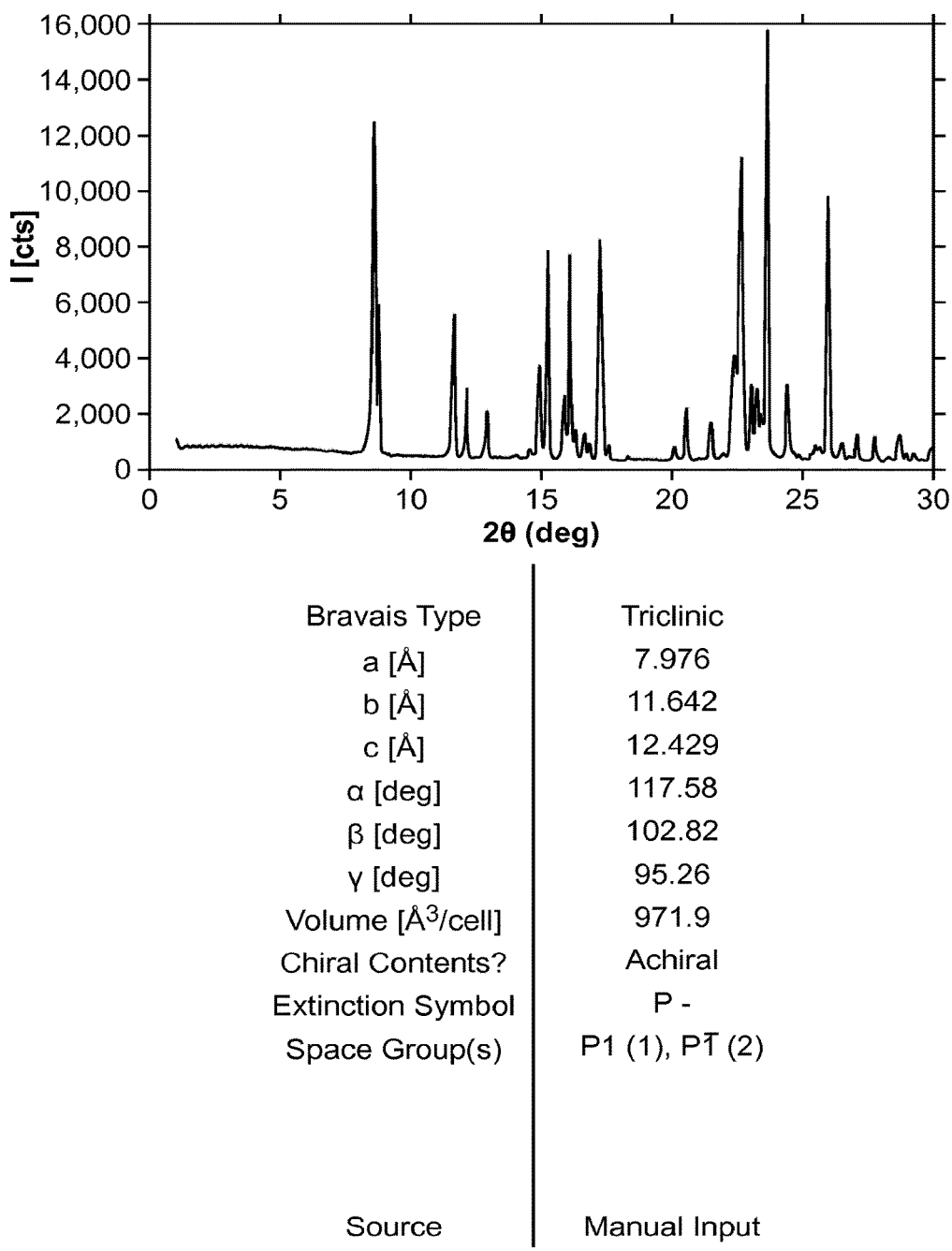
FIG. 22 depicts a contemplated XRPD profile for solvated Material L.
Figure 23:
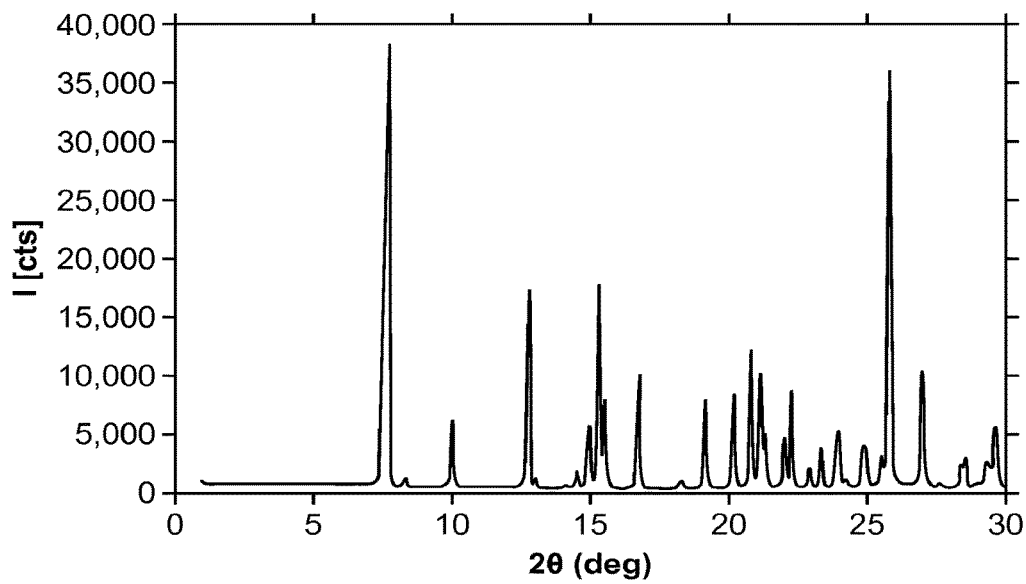
FIG. 23 depicts a contemplated XRPD profile for solvated Material M.
Figure 24:
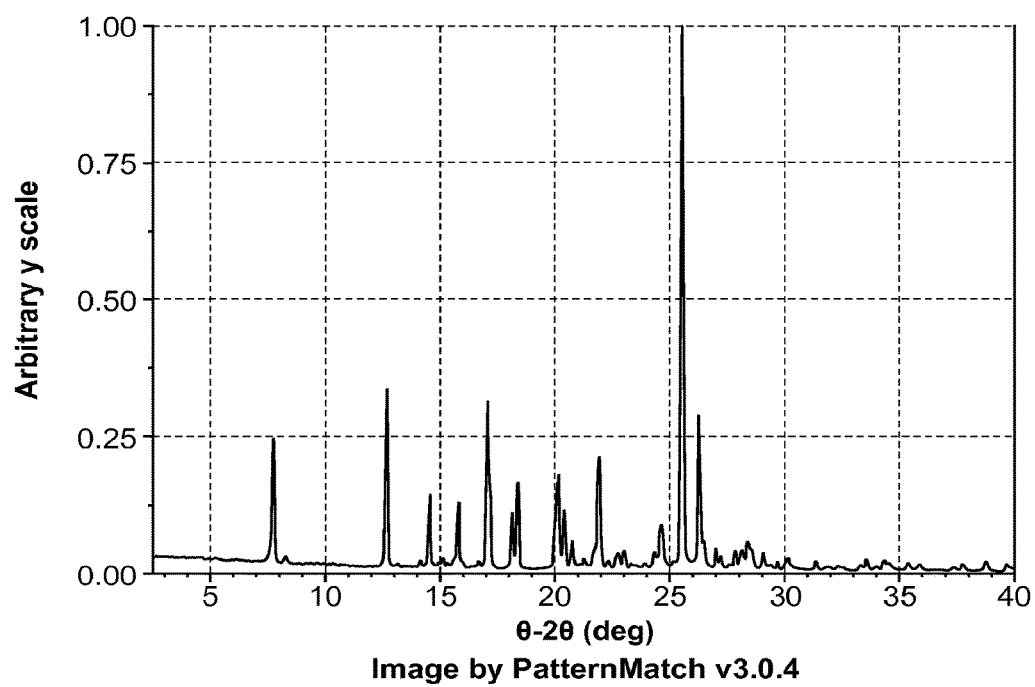
FIG. 24 depicts a contemplated XRPD profile for solvated Material O.
Figure 25:
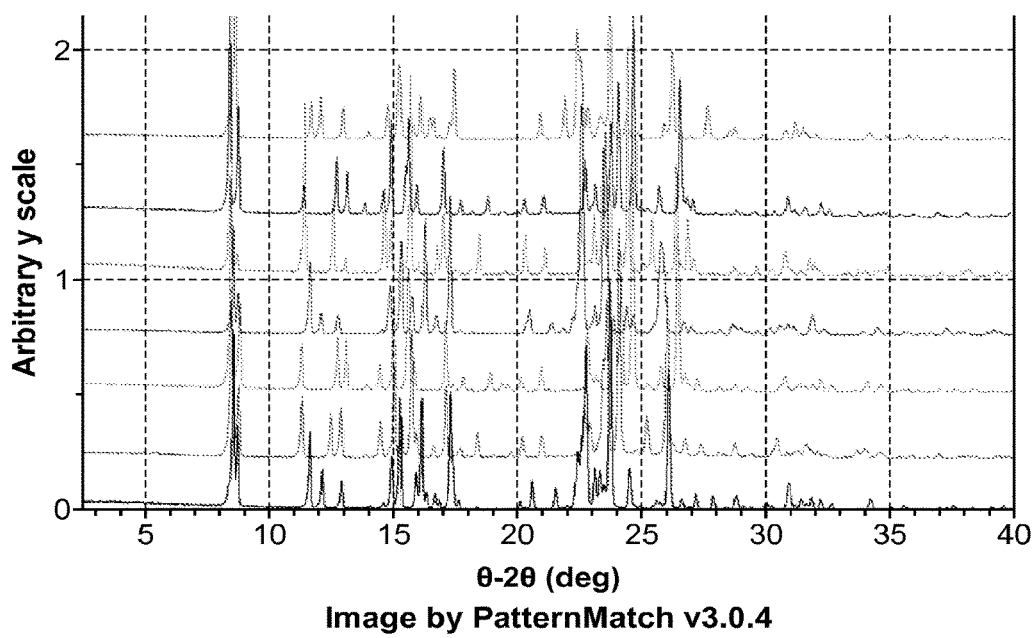
FIG. 25 depicts an XRPD profile comparison of contemplated isostructural solvates of the free base of Compound 1. From top to bottom: Material E from acetone; Material F from ACN; Material G from DCM; Material H from dioxane; Material J from EtOH; Material K from IPA/water (also obtained from IPA); and Material L from THF, Material M from MEK.

The Energy-Temperature Diagram of FIG. 17 is a semi-quantitative graphical solution of the Gibbs-Helmholtz equation, where the enthalpy (H) and free energy (G) isobars for each form are depicted as a function of temperature.

Example 26: Competitive Interconversion Slurry Experiments

Interconversion experiments were performed to support the thermodynamic relationship between polymorphs illustrated by the Energy-Temperature Diagram above. Interconversion or competitive slurry experiments are a solution-mediated process that provides a pathway for the less soluble (more stable) crystal to grow at the expense of the more soluble crystal form. Outside the formation of a solvate or degradation, the resulting more stable polymorph from an interconversion experiment is contemplated to be independent of the solvent used because the more thermodynamically stable polymorph has a lower energy and therefore lower solubility. The choice of solvent affects the kinetics of polymorph conversion and not the thermodynamic relationship between polymorphic forms.

The results of the interconversion studies are consistent with the tentative Energy-Temperature Diagram shown herein. Binary slurries were prepared at ambient, 6, and 57° C. using Forms I and II. Form II resulted from the majority of these experiments, confirming that Form II is more stable relative to Form I within this temperature range.

A few of the experiments conducted at ambient and 6° C. resulted in Material N. Although this does not provide specific clarification between Forms I and II, it does provide evidence that Material N is the most stable form relative to both Forms I and II at these temperatures (which were conducted below the estimated transition temperature of 42° C.). Additional interconversion slurries between Form II and Material N were conducted at temperatures which bracket this estimated transition temperature and confirm that Form II and Material N are enantiotropically related.

Example 27: Solid-State Nuclear Magnetic Resonance $^{13}C$ and $^{15}N$ spectra acquired for the three polymorphic forms I, II and Material N. See FIGS. 10 and 11. Spectra were acquired at 253K to prevent any low temperature transitions occurring during measurement and acquisition parameters optimised for each polymorphic form.

Based on solid-state nuclear magnetic resonance, all three forms are crystalline and are distinct polymorphic forms. Form I contains one molecule per asymmetric unit, Form II contains two molecules per asymmetric unit and Form N contains four molecules per asymmetric unit. See the $^{15}N$ spectra in FIG. 11.

Example 28: Chemical and Physical Stability Evaluation of the Free Base Form I of Compound 1

A mixture predominately composed of Free Base Form I (with Free Base Material D) were exposed to stability conditions to assess physical and chemical stability. Three conditions were used; open to 25° C./60% RH, open to 40° C./75% RH, and closed to 60° C. Physical stability was evaluated by XRPD. Chemical stability was determined through UPLC and $^1H$ NMR, when applicable. Materials were tested after 1, 7, and 14 days of exposure.

Chemical Stability of Free Base Form I

For the free base stability sample, UPLC showed very low levels of impurities present. The level of impurities did not rise significantly after 14 days of age. This would seem to indicate good chemical stability against the conditions used for stability assessment. The $^1H$ NMR spectra of samples exposed to 60° C. (14 days) were also consistent with this conclusion.

Physical Stability of Free Base Form I

The free base of Compound 1 remained unchanged, by XRPD, at 25° C./60% RH. However, differences were observed at the other two conditions. The few, minor peaks attributed to Free Base Material D were no longer observed, indicating that Material D is metastable and is not sustained at elevated temperatures. In addition, Free Base Form II was observed after 7 days of age. This is consistent with the conclusions discussed herein, where Free Base Form II is more stable relative to Free Base Form I at these temperatures.

Example 29: Physical Stability Evaluation of the Free Base Form II and Material N (Form N) of Compound 1

DSC was modulated at low underlying heating rate, followed by X-ray powder diffraction. A low underlying heating rate was used of 0.02° C. mid'. The temperature was 80° C. for form N and 90° C. for form II. Exposure was essentially isothermal, covering a temperature range with sensitivity to detect changes in physical form. The resultant materials were examined by X-ray powder diffraction. No changes in physical form were observed for either polymorphic form II or polymorphic form N (i.e., material N).

Forms II and N were exposed to 40° C./75% relative humidity (RH), 80° C., 80° C./80% RH for 9 days followed by X-ray powder diffraction. No changes in physical form were observed for either polymorphic form II or polymorphic form N.

The thermodynamic barrier for inter-conversion between polymorphic form II and form N is high, and physical stability is good for both forms. Thermally induced inter-conversion between form II and form N is unlikely to occur.

Example 30: The Relative Thermodynamic Stability of Polymorphic Forms II and N

Extended solvent mediated maturation studies were conducted with 1:1 w/w mixtures of polymorphic form II and form N. Hexane provided a good medium for solvent assessments. The temperatures used include −20° C., −10° C., 0° C., 10° C., 20° C., 30° C., 40° C. and 50° C. Significantly increased solubility was observed at 30° C., 40° C. and 50° C. Solids derived from maturation at −20° C., −10° C., 0° C., 10° C., 20° C. were analyzed by X-ray powder diffraction. In each case, significant conversion to Form N was observed.

Form N is thermodynamically more stable than form II at temperatures of 20° C. and lower. An enantiotropic relationship between the two forms is likely to exhibit equivalence in thermodynamic stability at ca. 30-40° C.

Example 31: Morphology of Form N

Initial examination of a batch of polymorphic form N indicates an acicular morphology.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

The invention claimed is:

1. A crystalline ansolvate of Compound 1:

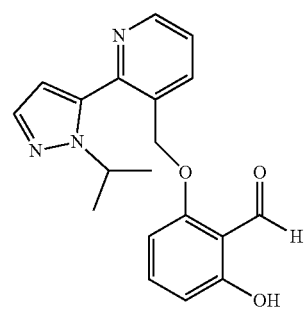

Compound 1 characterized by at least three X-ray powder diffraction peaks (Cu Kα radiation) selected from 11.65°, 11.85°, 12.08°, 16.70°, 19.65° and 23.48 °2θ (each ±0.2 °2θ).

2. The crystalline ansolvate of claim 1, characterized by an X-ray powder diffraction pattern (Cu Kα radiation) substantially similar to FIG. 7.

3. The crystalline ansolvate of claim 1, characterized by an endothermic peak at 95° C.±2° C. as measured by differential scanning calorimetry.

4. A pharmaceutical composition comprising a pharmaceutically acceptable excipient and a crystalline ansolvate of Compound 1:

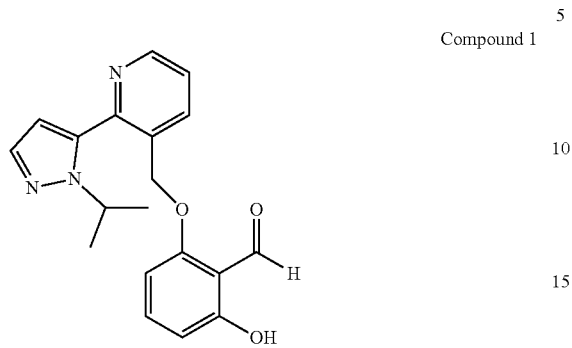

Compound 1 characterized by at least three X-ray powder diffraction peaks (Cu Kα radiation) selected from 11.65°, 11.85°, 12.08°, 16.70°, 19.65° and 23.48 °2θ (each ±0.2 °2θ). selected from 11.65°, 11.85°, 12.08°, 16.70°, 19.65° and 23.48 °2θ (each ±0.2 °2θ).

5. The pharmaceutical composition of claim 4, wherein the crystalline ansolvate of Compound 1 is characterized by an X-ray powder diffraction pattern (Cu Kα radiation) substantially similar to FIG. 7.

6. The pharmaceutical composition of claim 4, wherein the crystalline ansolvate of Compound 1 is characterized by an endothermic peak at 95° C.±2° C. as measured by differential scanning calorimetry.

* * * * *

UNITED STATES PATENT AND TRADEMARK OFFICE
CERTIFICATE OF CORRECTION

PATENT NO. : 10,137,118 B2  
APPLICATION NO. : 15/801152  
DATED : November 27, 2018  
INVENTOR(S) : Zhe Li et al.

Page 1 of 1

It is certified that error appears in the above-identified patent and that said Letters Patent is hereby corrected as shown below:

In the Claims

In Claim 4, Column 43, Lines 20-24, please replace the following text:
"...selected from 11.65°, 11.85°, 12.08°, 16.70°, 19.65° and 23.48 °2θ (each ±0.2 °2θ). selected from 11.65°, 11.85°, 12.08°, 16.70°, 19.65° and 23.48 °2θ (each ±0.2 °2θ)."

With the following text:
--...selected from 11.65°, 11.85°, 12.08°, 16.70°, 19.65° and 23.48 °2θ (each ±0.2 °2θ).--

Signed and Sealed this  
Twenty-fourth Day of December, 2019

Andrei Iancu  
*Director of the United States Patent and Trademark Office*